US011369633B2

(12) United States Patent
Towler

(10) Patent No.: US 11,369,633 B2
(45) Date of Patent: Jun. 28, 2022

(54) MESOPOROUS BIOACTIVE GLASSES AND USES THEREOF

(71) Applicant: Mark Towler, Toronto (CA)

(72) Inventor: Mark Towler, Toronto (CA)

( * ) Notice: Subject to any disclaimer, the term of this patent is extended or adjusted under 35 U.S.C. 154(b) by 0 days.

(21) Appl. No.: 15/354,289

(22) Filed: Nov. 17, 2016

(65) Prior Publication Data

US 2018/0133251 A1   May 17, 2018

(51) Int. Cl.
| | |
|---|---|
| *A61K 33/42* | (2006.01) |
| *C03C 3/097* | (2006.01) |
| *C03C 4/00* | (2006.01) |
| *A61L 26/00* | (2006.01) |
| *A61K 33/30* | (2006.01) |
| *A61K 33/24* | (2019.01) |
| *A61K 33/08* | (2006.01) |
| *A61K 33/00* | (2006.01) |
| *C03C 11/00* | (2006.01) |
| *A61L 15/18* | (2006.01) |
| *A61L 15/46* | (2006.01) |
| *A61L 15/28* | (2006.01) |

(52) U.S. Cl.
CPC .............. *A61K 33/42* (2013.01); *A61K 33/00* (2013.01); *A61K 33/08* (2013.01); *A61K 33/24* (2013.01); *A61K 33/30* (2013.01); *A61L 15/18* (2013.01); *A61L 15/28* (2013.01); *A61L 15/46* (2013.01); *A61L 26/0085* (2013.01); *C03C 3/097* (2013.01); *C03C 4/0007* (2013.01); *C03C 11/00* (2013.01); *A61L 2300/10* (2013.01); *A61L 2300/102* (2013.01); *A61L 2300/404* (2013.01); *A61L 2400/04* (2013.01)

(58) Field of Classification Search
None
See application file for complete search history.

(56) References Cited

U.S. PATENT DOCUMENTS

| | | | | | |
|---|---|---|---|---|---|
| 2,491,416 | A | * | 12/1949 | Olson .................... | C01G 35/00 424/617 |
| 2009/0208428 | A1 | * | 8/2009 | Hill ......................... | A61L 27/10 424/52 |
| 2014/0271912 | A1 | * | 9/2014 | Pomrink ................. | A61K 31/65 424/602 |

OTHER PUBLICATIONS

Marietta et al. (Transplantation Proceedings, 38, 812-814, 2006).*
Salinas et al. (Acta Biomaterialia, 7, 3452-3458, 2011). Substitutions of Cerium, gallium . . . .*
Pourshahrestani et al. (J. Mater. Chem. B., 4, 71-86, 2016, published on Nov. 18, 2015). Gallium-containing. . . .*
Shruti et al. (Acta Biomaterialia, 9, 4836-4844, 2013) Mesoporous bioactive . . . .*
Samuels et al. (Ann Surg.,163:427-431, 1966). A new hemostatic clip . . . .*
Ahuja, N.; Ostomel, T. A.; Rhee, P.; Stucky, G. D.; Conran, R.; Chen, Z.; Al-Mubarak, G. A.; Velmahos, G.; Alam, H. B., Testing of modified zeolite hemostatic dressings in a large animal model of lethal groin injury. Journal of Trauma and Acute Care Surgery 2006, 61 (6), 1312-1320.
Schneider, P., Adsorption isotherms of microporous-mesoporous solids revisited. Applied Catalysis A: General 1995, 129 (2), 157-165.
Kheirabadi, B., Evaluation of topical hemostatic agents for combat wound treatment. US Army Med Dep J 2011, 2 (1), 25-37.
Rao, S. B.; Sharma, C. P., Use of chitosan as a biomaterial: studies on its safety and hemostatic potential. Journal of biomedical materials research 1997, 34 (1), 21-28.
Coughlin, S. R., Thrombin signalling and protease-activated receptors. Nature 2000, 407 (6801), 258-264.
Sperling, C.; Fischer, M.; Maitz, M. F.; Werner, C., Blood coagulation on biomaterials requires the combination of distinct activation processes. Biomaterials 2009, 30 (27), 4447-4456.
Colman, R. W.; Schmaier, A. H., Contact system: a vascular biology modulator with anticoagulant, profibrinolytic, antiadhesive, and proinflammatory attributes. Blood 1997, 90 (10), 3819-3843.
Baker, S. E.; Sawvel, A. M.; Fan, J.; Shi, Q.; Strandwitz, N.; Stucky, G. D., Blood clot initiation by mesocellular foams: dependence on nanopore size and enzyme immobilization. Langmuir 2008, 24 (24), 14254-14260.
He, Q.; Gong, K.; Ao, Q.; Ma, T.; Yan, Y.; Gong, Y.; Zhang, X., Positive charge of chitosan retards blood coagulation on chitosan films. Journal of biomaterials applications 2013, 27 (8), 1032-1045.
Monroe, D. M.; Hoffman, M.; Roberts, H. R., Platelets and thrombin generation. Arteriosclerosis, thrombosis, and vascular biology 2002, 22 (9), 1381-1389.
Bowman, P. D.; Wang, X.; Meledeo, M. A.; Dubick, M. A.; Kheirabadi, B. S., Toxicity of aluminum silicates used in hemostatic dressings toward human umbilical veins endothelial cells, HeLa cells, and RAW267. 4 mouse macrophages. Journal of Trauma and Acute Care Surgery 2011, 71 (3), 727-732.
Shelby JE. Introduction to glass science and technology: Royal Society of Chemistry; 2005.
Wang Y, et al. The Journal of clinical investigation 2014;124:4281-93.
Novotna K, et al. Cellulose 2013;20:2263-78.
Lewis K, et al. European Surgery 2013;45:213-20.
Slutzky-Goldberg I, et al. Journal of endodontics 2008;34:735-8.
Ni H, et al. The Journal of clinical investigation 2000;106:385-92.
Kauvar, D. S.; Lefering, R.; Wade, C. E., Impact of hemorrhage on trauma outcome: an overview of epidemiology, clinical presentations, and therapeutic considerations. Journal of Trauma and Acute Care Surgery 2006, 60 (6), S3-S11.
Sauaia, A.; Moore, F. A.; Moore, E. E.; Moser, K. S.; Brennan, R.; Read, R. A.; Pons, P. T., Epidemiology of trauma deaths: a reassessment. The Journal of trauma 1995, 38 (2), 185-193.
B. J. Eastridge, R. L. Mabry, P. Seguin, J. Cantrell, T. Tops, P. Uribe, O. Mallett, T. Zubko, L. Oetjen-Gerdes and T. E. Rasmussen, J. Trauma Acute Care Surg., 2012, 73, S431-S437.

(Continued)

*Primary Examiner* — Tigabu Kassa
(74) *Attorney, Agent, or Firm* — Bereskin & Parr LLP/S.E.N.C.R.L., s.r.l.; Michael Fenwick

(57) ABSTRACT

The present disclosure relates to mesoporous glasses as well as uses of such glasses, for example, as hemostats.

10 Claims, 40 Drawing Sheets

(56) References Cited

OTHER PUBLICATIONS

S. Pourshahrestani, E. Zeimaran, I. Djordjevic, N. A. Kadri and M. R. Towler, Mater. Sci. Eng., C, 2016, 58, 1255-1268.
Alam, H. B.; Burris, D.; DaCorta, J. A.; Rhee, P., Hemorrhage control in the battlefield: role of new hemostatic agents. Military medicine 2005, 170 (1), 63-69.
Wedmore, I.; McManus, J. G.; Pusateri, A. E.; Holcomb, J. B., The chitosan-based hemostatic dressing: Experience in current combat operations. US Army Medical Department Journal 2005, 58-62.
F. L. Wright, H. T. Hua, G. Velmahos, D. Thoman, D. Demitriades and P. M. Rhee, J. Trauma Acute Care Surg., 2004, 56, 205-208.
V. Shanmugam and M. Robinson, Colorectal Dis., 2009, 11, 221-222.
P. Rhee, C. Brown, M. Martin, A. Salim, D. Plurad, D. Green, L. Chambers, D. Demetriades, G. Velmahos and H. Alam, J. Trauma Acute Care Surg., 2008, 64, 1093-1099.
Y. Ran, E. Hadad, S. Daher, O. Ganor, J. Kohn, Y. Yegorov, C. Bartal, N. Ash and G. Hirschhorn, Prehosp. Disaster Med., 2010, 25, 584-588.
M. E. Chavez-Delgado, C. V. Kishi-Sutto, X. N. A. de la-Riva, M. Rosales-Cortes and P. Gamboa-Sánchez, J. Surg. Res., 2014, 192, 678-685.
Cox, E. D.; Schreiber, M. A.; McManus, J.; Wade, C. E.; Holcomb, J. B., New hemostatic agents in the combat setting. Transfusion 2009, 49 (s5), 248S-255S.
Rhee, P.; Brown, C.; Martin, M.; Salim, A.; Plurad, D.; Green, D.; Chambers, L.; Demetriades, D.; Velmahos, G.; Alam, H., QuikClot use in trauma for hemorrhage control: case series of 103 documented uses. Journal of Trauma and Acute Care Surgery 2008, 64 (4), 1093-1099.
Acheson, E. M.; Kheirabadi, B. S.; Deguzman, R.; Dick Jr, E. J.; Holcomb, J. B., Comparison of hemorrhage control agents applied to lethal extremity arterial hemorrhages in swine. Journal of Trauma and Acute Care Surgery 2005, 59 (4), 865-875.
D. S. Kauvar, R. Lefering and C. E. Wade, J. Trauma Acute Care Surg., 2006, 60, S3-S11.
J. K. Wright, J. Kains, E. A. Wolf, F. Traweek, S. Schwarz, C. K. Loeffler, W. Snyder, L. D. Yantis Jr and J. Eggers, J. Trauma Acute Care Surg., 2004, 57, 224-230.
Kheirabadi, B. S.; Edens, J. W.; Terrazas, I. B.; Estep, J. S.; Klemcke, H. G.; Dubick, M. A.; Holcomb, J. B., Comparison of new hemostatic granules/powders with currently deployed hemostatic products in a lethal model of extremity arterial hemorrhage in swine. J Trauma Acute Care 2009, 66 (2), 316-328.
Bennett, B. L.; Littlejohn, L. F.; Kheirabadi, B. S.; Butler, F. K.; Kotwal, R. S.; Dubick, M. A.; Bailey, J. A. Management of External Hemorrhage in Tactical Combat Casualty Care: Chitosan-Based Hemostatic Gauze Dressings. TCCC Guidelines Change 13-05; DTIC Document: 2014.
B. Kheirabadi, US Army Med. Dep. J., 2011, 2, 25-37.
D. R. King, J. Trauma Acute Care Surg., 2011, 71, 1775-1778.
Floyd, C. T.; Rothwell, S. W.; Risdahl, J.; Martin, R.; Olson, C.; Rose, N., Salmon thrombin-fibrinogen dressing allows greater survival and preserves distal blood flow compared to standard kaolin gauze in coagulopathic swine with a standardized lethal femoral artery injury. J Spec Oper Med 2012, 12 (2), 16-26.
Kheirabadi, B. S.; Mace, J. E.; Terrazas, I. B.; Fedyk, C. G.; Estep, J. S.; Dubick, M. A.; Blackbourne, L. H., Safety evaluation of new hemostatic agents, smectite granules, and kaolin-coated gauze in a vascular injury wound model in swine. Journal of Trauma and Acute Care Surgery 2010, 68 (2), 269-278.
Kheirabadi, B. S.; Scherer, M. R.; Estep, J. S.; Dubick, M. A.; Holcomb, J. B., Determination of efficacy of new hemostatic dressings in a model of extremity arterial hemorrhage in swine. Journal of Trauma and Acute Care Surgery 2009, 67 (3), 450-460.

Gustafson, S. B.; Fulkerson, P.; Bildfell, R.; Aguilera, L.; Hazzard, T. M., Chitosan dressing provides hemostasis in swine femoral arterial injury model. Prehospital Emergency Care 2007, 11 (2), 172-178.
C. K. Murray, S. A. Roop, D. R. Hospenthal, D. P. Dooley, K. Wenner, J. Hammock, N. Taufen and E. Gourdine, Bacteriology of war wounds at the time of injury, DTIC Document, 2006.
N. E. Aronson, J. W. Sanders and K. A. Moran, Clin. Infect. Dis., 2006, 43, 1045-1051.
X. Yan, C. Yu, X. Zhou, J. Tang and D. Zhao, Angew. Chem., Int. Ed., 2004, 43, 5980-5984.
L. L. Hench, J. Am. Ceram. Soc., 1998, 81, 1705-1728.
Y. Li, Y.-Z. Liu, T. Long, X.-B. Yu, T. T. Tang, K.-R. Dai, B. Tian, Y.-P. Guo and Z.-A. Zhu, J. Mater. Sci.: Mater. Med., 2013, 24, 1951-1961.
Y. Zhu, C. Wu, Y. Ramaswamy, E. Kockrick, P. Simon, S. Kaskel and H. Zreiqat, Microporous Mesoporous Mater., 2008, 112, 494-503.
S. Brunauer, P. H. Emmett and E. Teller, J. Am. Chem. Soc., 1938, 60, 309-319.
E. P. Barrett, L. G. Joyner and P. P. Halenda, J. Am. Chem. Soc., 1951, 73, 373-380.
W. Fan, D. Wu, T. Ma and B. Fan, Dent. Mater. J., 2015, 34, 54-60.
28(a) C. Dai, Y. Yuan, C. Liu, J. Wei, H. Hong, X. Li and X. Pan, Biomaterials, 2009, 30, 5364-5375. 28(b) C. Dai, C. Liu, J. Wei, H. Hong and Q. Zhao, Biomaterials, 2010, 31, 7620-7630.
Y. Imai and Y. Nose, J. Biomed. Mater. Res., 1972, 6, 165-172.
S.-Y. Ong, J. Wu, S. M. Moochhala, M.-H. Tan and J. Lu, Biomaterials, 2008, 29, 4323-4332.
M. Ip, S. L. Lui, V. K. Poon, I. Lung and A. Burd, J. Med. Microbiol., 2006, 55, 59-63.
A. López-Noriega, D. Arcos, I. Izquierdo-Barba, Y. Sakamoto, O. Terasaki and M. Vallet-Regí, Chem. Mater., 2006, 18, 3137-3144.
D. Arcos, M. Vila, A. López-Noriega, F. Rossignol, E. Champion, F. Oliveira and M. Vallet-Regí, Acta Biomater., 2011, 7, 2952-2959.
C. Vaid, S. Murugavel, R. Kashayap and R. P. Tandon, Micropor Mesopor Mat, 2012, 159, 17-23.
X. Yan, X. Huang, C. Yu, H. Deng, Y. Wang, Z. Zhang, S. Qiao, G. Lu and D. Zhao, Biomaterials, 2006, 27, 3396-3403.
M. Franchini, G. Lusvardi, G. Malavasi and L. Menabue, Mater. Sci. Eng., C, 2012, 32, 1401-1406.
M. N. Rahaman, D. E. Day, B. S. Bal, Q. Fu, S. B. Jung, L. F. Bonewald and A. P. Tomsia, Acta Biomater., 2011, 7, 2355-2373.
V. Grover, A. Kapoor, R. Malhotra and R. S. Uppal, J. Indian Soc. Periodontol., 2013, 17, 104.
Y. Zhao, X. Sun, G. Zhang, B. G. Trewyn, I.I. Slowing and V. S.-Y. Lin, ACS Nano, 2011, 5, 1366-1375.
S. R. Coughlin, Nature, 2000, 407, 258-264. 40a B. S. Kheirabadi, J. W. Edens, I. B. Terrazas, J. S. Estep, H. G. Klemcke, M. A. Dubick and J. B. Holcomb, J. Trauma Acute Care Surg., 2009, 66, 316-328.
Brunauer, S.; Emmett, P. H.; Teller, E., Adsorption of gases in multimolecular layers. Journal of the American chemical society 1938, 60 (2), 309-319.
Pourshahrestani, S.; Zeimaran, E.; Kadri, N. A.; Gargiulo, N.; Samuel, S.; Naveen, S. V.; Kamarul, T.; Towler, M. R., Gallium-containing mesoporous bioactive glass with potent hemostatic activity and antibacterial efficacy. Journal of Materials Chemistry B 2016, 4 (1), 71-86.
Barrett, E. P.; Joyner, L. G.; Halenda, P. P., The determination of pore volume and area distributions in porous substances. I. Computations from nitrogen isotherms. Journal of the American Chemical society 1951, 73 (1), 373-380.
Dai, C.; Yuan, Y.; Liu, C.; Wei, J.; Hong, H.; Li, X.; Pan, X., Degradable, antibacterial silver exchanged mesoporous silica spheres for hemorrhage control. Biomaterials 2009, 30 (29), 5364-5375.

\* cited by examiner (c)

(d)

(g)

(a)

(b)

(c)

(d)

(e)

(a)

(b)

(a)

(b)

(c)

(a)

(b)

(a)

(b)

(c)

(d)

(e)

(f)

(i)

(j)

(k)

(l)

(m)

US 11,369,633 B2

MESOPOROUS BIOACTIVE GLASSES AND USES THEREOF

FIELD

The present disclosure relates to mesoporous glasses as well as uses of such glasses, for example, as hemostats.

BACKGROUND

Despite considerable advances in hemostatic innovation over the last two decades, blood loss remains one of the most frequent causes of potentially survivable death in combat settings and the second leading cause of trauma death in civilian hospitals[1]. Further, based on the recent combat mortality analysis, hemorrhage was the main cause in almost 91% of all pre-hospital deaths which were deemed potentially survivable.[2]

In the last decade, a number of hemostatic agents have been used for the rapid control of bleeding. Among those, inorganic hemostats have been used because these materials are free of animal or human derived proteins that can cause allergic reactions.[3] Two of the most common hemostats used on the battlefield are HemCon (HC, chitosan standard dressing, HemCon Inc., Portland Oreg.) and QuikClot (QC, zeolite powder dressing, Z-Medica, Wallingford, Conn.)[4, 5,6,7,8,9] which are inorganic coagulation accelerators that have the ability to staunch bleeding. However, this "first generation" of advanced hemostatic products, whilst offering potent hemostasis in animal haemorrhage models and in some clinical trials, were later abandoned because of either tissue burning (QC) or lack of efficacy in controlling excessive bleeding (HC)[10]. Animal studies and case reports also revealed that the application of QC can result in thermal injuries and abnormal foreign-body reaction because of its highly exothermic reaction and poor biodegradability.[5,11,12] Although the safety concern with QC was addressed in its modified version, QuikClot Advanced Clotting Sponge Plus (ACS+, Z-Medica, Wallingford. Conn., USA), which is made up of synthetic zeolite beads packaged in small porous cotton bags, it is ineffective in controlling arterial bleeding[13]. Therefore, the first generation of hemostats have been replaced by second-generation dressings such as QuickClot Combat Gauze (QCG, kaolin-incorporating gauze, Z-Medica, Wallingford, Conn., USA), WoundStat (WS, clay mineral powder, TraumaCure Inc. Bethesda, Md., USA) and Celox (CX, chitosan powder, Medtrade Products Ltd. Crewe, United Kingdom) which have been reported to offer efficacy in reducing blood loss and improving survival rates. In 2008, QCG was selected by the Committee on Tactical Combat Casualty Care (CoTCCC) as the first-line treatment to control life-threatening external haemorrhage and WS was selected as a backup agent[14]. However, neither generation was found to be free of side effects. Some studies also found that QCG does not often provide immediate hemostasis when applied to the bleeding site, resulting in larger blood loss compared with other agents.[15] Furthermore, the dressing may not be reliable for controlling hemorrhage in patients with coagulopathy since its hemostatic abilities depend solely on the blood-clotting activity of the host.[15,16] It has also been shown to be less effective in coagulopathic patients[17]. WS was found to have significant safety issues regarding toxicity, embolization and tissue inflammation and was later withdrawn from TCCC Guidelines[18]. Despite possessing many of the ancillary characteristics of an ideal hemostatic dressing and success in controlling haemorrhage, CX has also been reported to induce a strong inflammatory response in some tissue[18(a)]. Although newer hemostatic agents including Chitosan-based gauzes were found to be superior to the first and second generation hemostatics, their dressings have shown variable efficacy under high pressure arterial blood flow in animal studies[19]. For instance, while the gauzes were able to stop low pressure bleeding, they failed to maintain hemostasis after intravenous administration of fluids to raise blood pressure back to baseline[19(a)].

Infection of wounds is a further serious complication that may delay and/or impair healing. Although many antibiotics have been developed to reduce bacteria at the wound site, an important challenge facing caregivers is the increasing rate of antibiotic-resistant bacterial infections.[20,21]

A new generation of bioactive glasses, referred to as mesoporous bioactive glasses (MBGs), were first prepared by Yan et al. in 2004 using the evaporation-induced self-assembly (EISA) process.[22] The bioactive glasses in the 80% $SiO_2$-15% CaO-5% $P_2O_5$ system are distinct from conventional non-mesoporous bioactive glasses developed by Hench and co-workers[23] since they possess highly ordered mesoporous channel structures and significantly greater specific surface area.[22] These MBGs also offer other characteristics including a greater pore volume and pore sizes ranging from 2 to 10 nm that may render them suitable for drug delivery and musculoskeletal applications.[22,24,25]

SUMMARY

The present disclosure relates to methods for modulating hemostasis comprising contacting blood with mesoporous bioactive glasses containing a metal ion. In particular, the present disclosure relates to a method for inducing hemostasis in a subject in need thereof, the method comprising contacting blood with a hemostatically effective amount of a composition comprising a mesopourous bioactive glass (MBG), wherein the MBG comprises:
  (i) silicon dioxide;
  (ii) calcium oxide;
  (iii) phosphorous pentoxide; and
  (iv) a metal ion having antibiotic activity which is gallium, tantalum, zinc, germanium or strontium.

In one embodiment, the metal ion is present in an amount less than about 1.5 mol %.

The present disclosure also includes medical devices or bandages which are coated and/or impregnated with the mesoporous bioactive glasses as described herein.

Further embodiments of the disclosure include methods for reducing hemorrhaging at the site of a wound, cut or incision comprising applying a composition or bandage coated and/or impregnated with the composition as described herein.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the drawings in which.

DETAILED DESCRIPTION

I. Definitions

Figure 1:
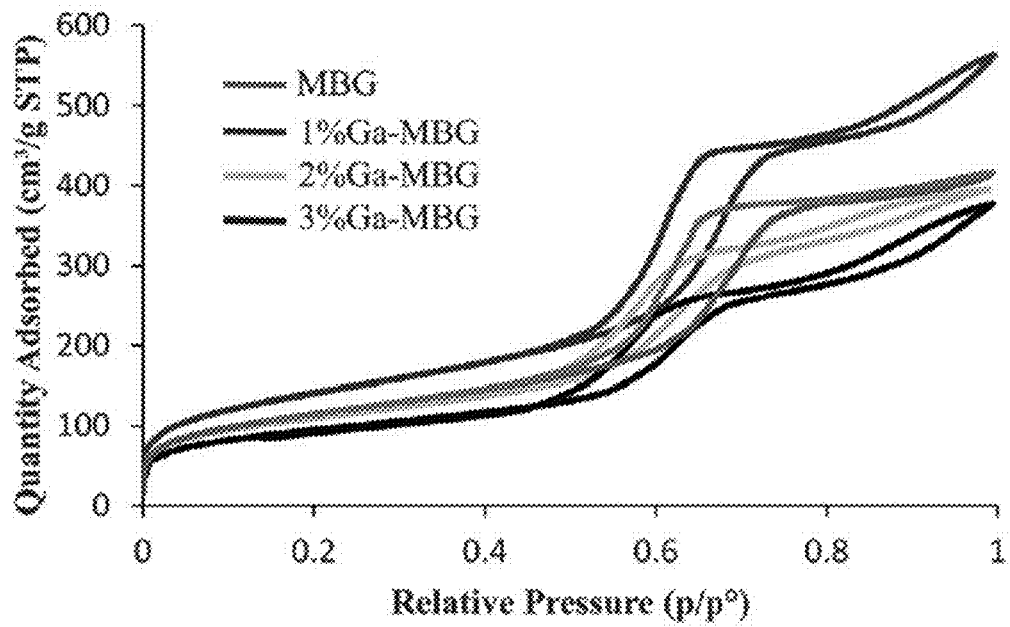
FIG. 1 shows (a) $N_2$ adsorption-desorption isotherms and (b) the corresponding pore size distributions of a mesoporous bioactive glass (MBG) and Ga-substituted mesoporous bioactive glasses (Ga-MBGs; 1, 2 and 3 mol %); (c) small angle X-ray diffraction (SAXRD) of MBG and Ga-MBGs (1, 2 and 3 mol %); and (d) wide-angle X-ray diffraction (WXRD) analysis of MBG and 3% Ga-MBG.
Figure 1:
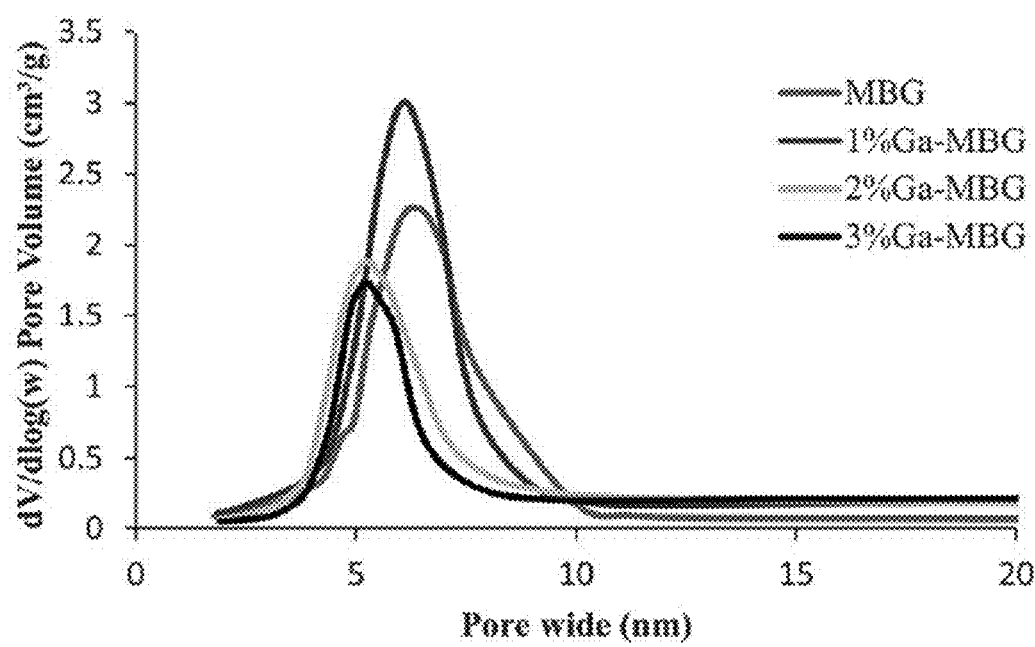
Figure 1:
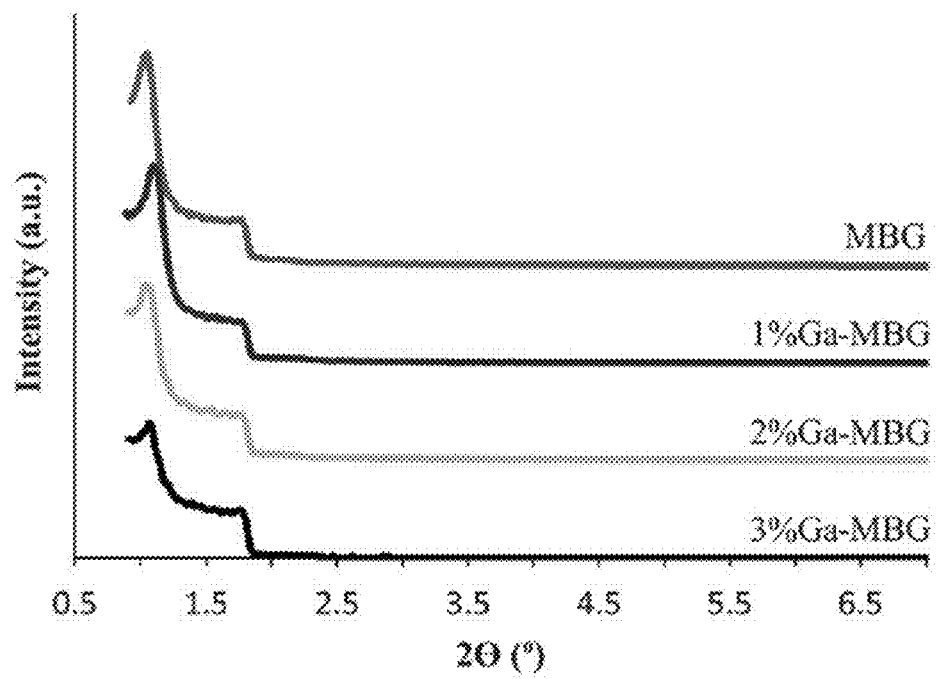
Figure 1:
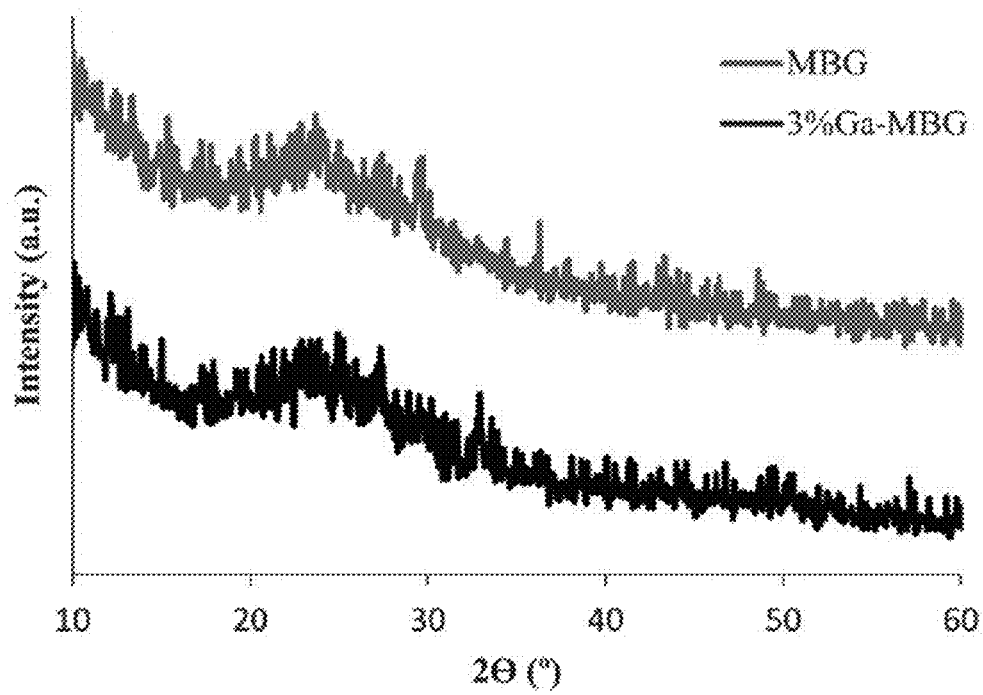

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in the present disclosure, the singular forms "a", "an" and "the" include plural references unless the content clearly dictates otherwise. In embodiments comprising an "additional" or "second" component, the second component is different from the other components or first component. A "third" component is different from the other, first, and second components, and further enumerated or "additional" components are similarly different.

The term "pharmaceutically acceptable" means compatible with the treatment of subjects, for example, animals such as humans.

The term "subject" as used herein, refers to an animal, preferably a mammal, most preferably a human, who is in need of hemostasis, or who is suffering from a hemorrhagic event. The term subject may be interchangeably used with the term patient in the context of the present disclosure.

The term "blood" as used herein refers to whole blood (including plasma and cells) and includes arterial, capillary and venous blood.

The term "induce" or "inducing" or "modulating" as used herein in reference to hemostasis refers to the compositions of the disclosure promoting hemostasis and reducing the time for blood clot formation and a reduction, or stoppage, in bleeding.

The term "hemostasis" as used herein refers to the inhibition or reduction or suppression of bleeding, including the arrest of bleeding, which is accompanied by blood clot formation using the compositions of the disclosure.

The term "hemostatically effective amount" as used herein refers to an amount of a composition which is required for hemostasis.

The term "mesoporous bioactive glass" as used herein refers to a glass having highly ordered mesoporous channel structures and greater specific surface area than regular glass.

The term "antibiotic activity" as used herein refers to a metal ion having the ability to inhibit the growth of or kill a pathogen, such as pathogens present at the site of a wound.

II. Methods and Uses of Mesoporous Glasses

Haemorrhage remains the leading cause of potentially survivable death in both military and civilian populations. Although a large variety of hemostatic agents have been developed, many of them have an inadequate capacity to induce hemostasis and are not effective in killing bacteria. Accordingly, the present disclosure is directed to method for modulating or inducing hemostasis in a subject in need thereof, the method comprising contacting blood with a hemostatically effective amount of a composition comprising a mesopourous bioactive glass (MBG), wherein the MBG comprises:
(i) silicon dioxide;
(ii) calcium oxide;
(iii) phosphorous pentoxide; and
(iv) a metal ion having antibiotic activity which is gallium, zinc, germanium, tantalum, or strontium.

In another embodiment, the present disclosure is directed to the use of a composition comprising a mesopourous bioactive glass (MBG) for inducing hemostatis in a subject, wherein the MBG comprises:
(i) silicon dioxide;
(ii) calcium oxide;
(iii) phosphorous pentoxide; and
(iv) a metal ion having antibiotic activity which is gallium, zinc, germanium, tantalum, or strontium.

In another embodiment, the MBG comprises:
(i) silicon dioxide in an amount from about 50.0 mol % to about 90 mol %;
(ii) calcium oxide in an amount from about 10.0 mol % to about 20 mol %;
(iii) phosphorous pentoxide in an amount from about 1.0 mol % to 10 mol %; and
(iv) a metal ion in an amount from about 0.1 mol % to about 50.0 mol %.

In another embodiment, the MBG comprises:
(i) silicon dioxide in an amount from about 70.0 mol % to about 90 mol %;
(ii) calcium oxide in an amount from about 10.0 mol % to about 20 mol %;
(iii) phosphorous pentoxide in an amount from about 1.0 mol % to 10 mol %; and (iv) a metal ion in an amount from about 0.1 mol % to about 3.0 mol %.

In a further embodiment, the MBG comprises:
(i) silicon dioxide in an amount from about 77.0 mol % to about 79 mol %
(ii) calcium oxide in an amount of about 15.0 mol %;
(iii) phosphorous pentoxide in an amount of about 5.0 mol %; and
(iv) a metal ion in an amount from about 1.0 mol % to about 3.0 mol %.

In another embodiment, the MBG comprises
(i) silicon dioxide in an amount of about 79.0 mol % to about 80 mol %;
(ii) calcium oxide in an amount of about 15.0 mol %;
(iii) phosphorous pentoxide in an amount of about 5.0 mol %; and
(iv) a metal ion in an amount of less than about, or about, 1.0 mol %.

In one embodiment, wherein the MBG comprises
(i) silicon dioxide in an amount of about 79.0 mol %.
(ii) calcium oxide in an amount of about 15.0 mol %;
(iii) phosphorous pentoxide in an amount of about 5.0 mol %;
(iv) a metal ion in an amount of about 1.0 mol %.

In another embodiment of the disclosure, the metal ion is $Ga^{3+}$, $Ta^{5+}$, $Zn^{2+}$, $Ge^{4+}$ or $Sr^{2+}$. In one embodiment, the metal ion is present as an oxide or carbonate. In one embodiment, the $Ga^{3+}$ ion is present as $Ga_2O_3$, the $Ta^{+5}$ ion is present as $Ta_2O_5$, the $Sr^{2+}$ is present as SrO, the $Zn^{2+}$ is present as ZnO and the $Ge^{4+}$ is present as $GeO_2$. It will be understood by those skilled in the art that the mesoporous bioactive glasses is a network formed from silicon dioxide, calcium oxide and phosphorous pentoxide, which form the mesoporous bioactive glasses ($SiO_2.CaO.P_2O_5$). When the metal ions are added during the synthesis of the MBGs, the metal ion, such as $Ga_2O_3$ substitutes for $SiO_2$. For example, if an MBG comprises 80 mol % $SiO_2$, 15 mol % CaO and 5 mol % $P_2O_5$, the addition of a metal ion results in an MBG comprising (80 mol %–x) $SiO_2$, 15 mol % CaO, 5 mol % $P_2O_5$, and x is the amount of metal ion, such as $Ga_2O_3$, where x is the amount of the metal ion, for example, about 0.1 mol % to about 3 mol %, or about 1 mol %.

In one embodiment, the metal ion having antibiotic activity also has anti-inflammatory activity. In one embodiment, the metal ion is $Ga^{3+}$ which has anti-inflammatory activity. In one embodiment, the hemorrhaging event which requires hemostasis is a wound or other insult on the body of a subject which causes the subject's inflammatory response at the site of the wound or insult, and therefore complicating hemostasis. In one embodiment, the metal ion having antibiotic activity also possesses anti-inflammatory activity, further inducing hemostasis.

In one embodiment, the metal ion having antibiotic activity is present in the MBG at an amount of less than 2.0 mol %, less than about 1.5 mol %, or less than about 1.25 mol %, or less than about 1.0 mol %, or about 1.0 mol %. In another embodiment, the metal ion having antibiotic activity is present in an amount which provides antibiotic activity to less than about 2.0 mol %, or about 0.1 mol % to less than 2.0 mol %, or about 0.1 mol % to less than 1.5 mol %. In one embodiment, the compositions comprising the MBG have a surface area of at least 500 $m^2/g$. In one embodiment, the metal ions having antibiotic activity are bivalent or polyvalent metal ions, such as $Ga^{3+}$, and during network formation of the mesoporous bioactive glass, cause an increase in the surface area, mesopore size and pore volume of the MBG compared to when no bivalent or polyvalent metal ion is included. The increase in surface area of the MBG further facilitates hemostasis as it increases the amount of blood that can be absorbed within the composition and stimulating blood coagulation and platelet adhesion.

In another embodiment, MBG has small angle X-ray diffraction peaks of 2θ at 1.1°.

In another embodiment of the disclosure, modulating or inducing hemostasis using the MBG composition decreases the time required for blood coagulation.

In another embodiment of the disclosure, the composition comprising the MBG, consists essentially of, or consists of
(i) silicon dioxide;
(ii) calcium oxide;
(iii) phosphorous pentoxide; and
(iv) a metal ion having antibiotic activity which is gallium, tantalum, zinc, germanium or strontium.

In another embodiment, the MBG consists essentially of, or consists of:
(i) silicon dioxide;
(ii) calcium oxide;
(iii) phosphorous pentoxide; and
(iv) a metal ion having antibiotic activity which is gallium, tantalum, zinc, germanium or strontium present in an amount less than about less than about 1.5 mol %, or less than about 1.25 mol %, or less than about 1.0 mol %, or about 1.0 mol %.

In another embodiment, the MBG consists essentially of, or consists of:
(i) silicon dioxide present at an amount of about 79 mol %;
(ii) calcium oxide present at an amount of about 15 mol %;
(iii) phosphorous pentoxide present at an amount of about 5 mol %; and
(iv) gallium oxide ($Ga_2O_3$) present in an amount of about 1.0 mol %.

In other embodiments, the compositions further comprise pharmaceutically acceptable carriers, diluents, and/or excipients.

The present disclosure also includes a method for reducing hemorrhaging as a result of a hemorrhagic event, such as a wound, insult, cut or incision, in a subject in need thereof, the method comprising contacting the wound, insult, cut or incision with a composition comprising an MBG as described in herein.

The present disclosure also includes a medical device or bandage coated and/or impregnated with the composition comprising the MBG described herein, wherein the composition decreases the time for blood coagulation to occur (or increases the rate or speed at which blood coagulation occurs). In one embodiment, the bandage comprises a knitted cellulosic gauze bandage. Accordingly, in one embodiment of the disclosure, there is included a method for reducing, or stopping, hemorrhaging (as a result of a hemorrhagic event such as a wound, insult, cut or incision) of a subject, comprising applying a gauze bandage coated and/or impregnated with the compositions described herein to the wound, insult, cut or incision, to facilitate hemostasis and reduce the time for blood coagulation to occur.

In other embodiments, the MBG compositions of the disclosure are coated on stents or implants to facilitate hemostasis. In another embodiment, the MBG compositions are used as bone void fillings to facilitate hemostasis in bone.

The present disclosure also includes kits comprising
(i) an MBG composition described above;
(ii) a medical device or bandage;

(iii) instructions for use for coating the medical device or bandage with the composition to facilitate hemostasis.

The following non-limiting examples are illustrative of the present disclosure:

EXAMPLES

Example 1: Gallium-Containing Mesoporous Bioactive Glass with Hemostatic Activity and Antibacterial Efficacy The present study evaluated the in vitro acceleratory effect on the blood coagulation cascade and the antibacterial function of Ga-containing MBGs (Ga-MBGs), in comparison with a Ga-free MBG. Accordingly, a series of MBGs containing three different concentrations of $Ga_2O_3$ (1, 2 & 3 mol %) were prepared by the EISA process, and their physiochemical properties in vitro hemostatic activity, biocompatibility and antibacterial activity against *Escherichia coli* (*E. coli*) and *Staphylococcus aureus* (*S. aureus*) were investigated.

I. Materials and Methods (a) Materials

Tetraethyl orthosilicate (TEOS, 98%, Sigma-Aldrich), triethyl phosphate (TEP, ≥99.8%, Sigma-Aldrich), calcium nitrate tetrahydrate [$Ca(NO_3)_2 \cdot 4H_2O$, ≥99%, Sigma-Aldrich], gallium(III) nitrate hydrate [$Ga(NO_3)_3 \cdot xH_2O$, 99.9%, Sigma-Aldrich], triblock copolymer $EO_{20}PO_{70}EO_{20}$ (P123, Sigma-Aldrich), ethyl alcohol (EtOH, Sigma-Aldrich) and nitric acid ($HNO_3$, Sigma-Aldrich) were of reagent grade and used without any further purification.

(b) Synthesis of MBGs

Ordered MBGs (80−x) % $SiO_2$-15% CaO-5% $P_2O_5$-x % $Ga_2O_3$, doped with different contents of $Ga_2O_3$, were synthesized by using P123 as a structure directing agent. In the present example, CaO and $P_2O_5$ content were kept constant and $SiO_2$ and $Ga_2O_3$ content were varied. The nominal chemical composition of the synthesized samples is reported in Table 1.

TABLE 1

Nominal chemical composition of MBG and Ga-MBGs[1].

| Glass code | $SiO_2$ | CaO | $P_2O_5$ | $Ga_2O_3$ |
|---|---|---|---|---|
| MBG | 80 | 15 | 5 | 0 |
| 1% Ga-MBG | 79 | 15 | 5 | 1 |
| 2% Ga-MBG | 78 | 15 | 5 | 2 |
| 3% Ga-MBG | 77 | 15 | 5 | 3 |

[1]Amounts of components given in mol %.

In an exemplary synthesis, 4 g of P123 was dissolved in 60 g of EtOH, followed by the addition of TEOS, TEP, $Ca(NO_3)_2 \cdot 4H_2O$, $Ga(NO_3)_3 \cdot xH_2O$ (the latter only in the case of Ga-MBGs) and 1.0 mL $HNO_3$ (0.5 M). The mixture was vigorously stirred overnight at room temperature, and then the as-derived clear sol was transferred into a Petri dish and kept for several days at room temperature for the EISA process. The dried gels were calcined at 600° C. for 5 h to remove the redundant organic template and to obtain the final glass powder. The as-synthesized MBG and Ga-MBGs were then ground into two particle sizes ranging in the 32-75 and 250-300 µm intervals and stored in a desiccator until usage.

(c) Characterization of MBG and Ga-MBGs

Nitrogen Adsorption-Desorption at 77K:

Nitrogen ($N_2$) adsorption-desorption analysis at 77 K was performed using a Micromeritics ASAP 2020. The samples were degassed at 200° C. for 5 h. Brunauer-Emmett-Teller (BET) and Barret-Joyner-Halenda (BJH) methods were used for the evaluation of the specific surface area, pore size distribution and pore volume.[26,27]

Small and Wide Angle X-Ray Diffractions:

Small and wide angle X-ray diffraction (SAXRD and WAXRD, respectively) patterns were obtained using a X-ray diffractometer (PANalytical Empyrean) with Cu Kα (l=0.154 nm) radiation (40 kV, 40 mA). The SAXRD patterns were collected in the 2θ range between 0.6° and 7° with a step size of 0.02° and a counting time of 5 s per step. In addition, WAXRD patterns were collected in the 2θ range between 10° and 60° with a step size of 0.02° and a counting time of 5 s per step.

Transmission Electron Microscopy (TEM):

The inner microstructure of the samples was examined by transmission electron microscopy (TEM, JEOL JEM-2100F microscope) operating at 200 kV.

Scanning Electron Microscopy and Energy-Dispersive X-Ray Spectroscopic Analysis (SEM-EDS):

An energy-dispersive X-ray spectrometer (EDS: 20 mm X-Max, Oxford Instruments, Oxford, UK) and the INCA software connected to a scanning electron microscope (SEM: Quanta™ 250 FEG-FEI, USA) at 20 kV were used for the assessment of the surface morphology and composition of the glasses.

Fourier Transform Infrared Spectroscopy (FT-IR):

FT-IR spectra of the synthesized samples were collected using a Fourier transform infrared spectrometer (ATR-FTIR400, Perkin Elmer instruments, USA) within the 400-1400 $cm^{-1}$ wavelength range at room temperature.

Zeta Potential Measurement:

Zeta potential determination was carried out in a Zetasizer Nanoseries (Malvern Instruments) via suspending MBG and Ga-MBG particles in phosphate buffered solution (PBS) at pH 7.4.

In Vitro Ion Release and Degradation Measurements:

Ion release measurements of MBG and Ga-MBGs were performed using a microwave plasma-atomic emission spectrometer (MP-AES) Agilent 4100 (Agilent Technologies, Inc., Santa Clara, Calif., USA) to investigate the concentration of silicate ($SiO_4^{4-}$), phosphate ($PO_4^{3-}$), $Ca^{2+}$ and $Ga^{3+}$ ions in the soaking solution. For this purpose, 20 mg of each dried sample was immersed in a polypropylene vial containing 10 mL of 0.05 M tris(hydroxymethyl)-aminomethane-HCl (Tris-HCl, Sigma-Aldrich) buffer solution (pH=7.4), and incubated up to 3 days at 37° C. with continuous shaking at 120 rpm (n=3).[28] At specified time points (0.5, 1, 2, 3, 6, 12, 24, 48 and, 72 h), the powders were collected by filtration, and the extract was used for ion release studies. The degradation properties of MBG and Ga-MBGs were also evaluated at 37° C. in Tris-HCl solution (pH 7.4). The samples were immersed in vials containing 10 mL of the solution following incubation up to 14 days. At the scheduled time, the samples were separated from the solution by filtration and rinsed with acetone followed by drying in an oven at 37° C. to a constant weight. For measuring the weight loss, the following equation was used: weight loss (%)=$[(W_0-W_t)/W_0] \times 100\%$, where $W_0$ is the initial weight of the samples and $W_t$ is the weight of samples after immersion in the solution.

In Vitro Blood Plasma Coagulation Assay:

To evaluate coagulation behaviors of MBG and Ga-MBGs, the activated partial thromboplastin time (APTT) and prothrombin time (PT) were performed. Fresh human blood anticoagulated with 3.2% sodium citrate was collected from healthy volunteers with approval from the Medical Ethics Committee of University of Malaya, Kuala Lumpur, Malaysia (UMMC reference number 967.10). The platelet poor plasma (PPP) was obtained via centrifugation of whole blood at 3500 rpm for 10 min at 25° C. For each assay, the MBG and Ga-MBGs were placed into test tubes containing 100 mL PPP. For the APTT assay, the above test tubes with selected samples (MBG or Ga-MBGs) and 100 mL APTT reagent were incubated at 37° C. in a water bath for 2 minutes. Then, 100 mL of pre-warmed $CaCl_2$ was added and the clotting time at which the fibrous substance appeared was recorded. For the PT assay, the pre-warmed plasma was incubated with the samples for 2 min at 37° C. The PT was measured simultaneously after the addition of 100 mL of pre-warmed PT reagent. The tests for negative control were performed without MBG and Ga-MBGs.

PBS Absorption Efficiency In Vitro:

The in vitro absorption efficiency of MBG and Ga-MBGs was assessed in PBS (pH=7.4). The test was performed according to Dai's method as already described.[28a] Before doing the test, the samples were dried at 50° C. in a vacuum overnight to completely eliminate the residual water. Briefly, the pre-weighed dried samples (having mass $W_{dry}$) were placed at the center of a folded filter paper in a funnel so that fluid (PBS) can be uniformly absorbed by the samples. After that, the fluid was added dropwise at a rate of 10 mL min$^{-1}$ until the absorption by the samples reached its saturation state (when the first drop of fluid trickled from the funnel). The mass of the wet sample was then recorded as $W_{wet}$ after removing the filter paper. The absorption ratio of samples with PBS was calculated by using the following equation: $(\%)=[(W_{wet}-W_{dry})/W_{dry}]\times100\%$, where $W_{dry}$ and $W_{wet}$ are the weight of the samples before and after the PBS immersion, respectively. For each absorption study, three samples were examined.

In Vitro Thrombus Formation:

The in vitro thrombogenic activity of the samples was evaluated with citrated human blood using a method adapted from Imai.[29] Thirty milligrams of MBG and Ga-MBGs were introduced into the wells of 24-well culture plates containing 1 mL of citrated human blood to start the thrombus formation followed by incubation at 37° C. for three different time points (15, 30 and 60 min). The reactions were stopped at appropriated time intervals through adding 10 mL of deionized water. The formed thrombus was fixed in 37% formaldehyde solution for 10 min at room temperature. The fixed samples were then placed in an oven overnight at 50° C. until constant weight was obtained. The degree of thrombogenicity (DT) of the samples at a given time was defined as follows: $DT=[(W_t-W_0)/W_0]\times100\%$, where $W_0$ and $W_t$ are the weights of the samples before and after in contact with blood, respectively. The assay was done at least three times for each sample. The thrombus formed on the surfaces of the samples was photographed by a digital camera. The interaction of whole blood cells with the synthesized samples was also visualized by a field emission scanning electron microscope (FESEM: Quantat 250 FEG-FEI, USA). Prior to fixing as described above, the soaked samples were washed with PBS to remove the blood cells not fully adhered and then were fixed using 2.5% glutaraldehyde for 2 h, immediately after the rinsing step. Afterwards, samples underwent a graded dehydration series of ethanol and HMDS (hexamethyldisilazane) drying for 10 min. The particles were then left drying for 2 days in a fume hood at room temperature. The dried samples were then sputtered with a thin layer of gold and the photomicrographs were collected with an accelerating voltage of 15 kV.

In Vitro Evaluation of Platelet Adhesion:

A lactate dehydrogenase (LDH) assay was used to measure the number of adherent platelets. Human blood samples were freshly obtained from volunteers and anticoagulated with 3.2% sodium citrate. The citrated human blood samples were centrifuged at 1500 rpm for 10 min to remove leukocytes and erythrocytes. Then the supernatant, platelet rich plasma (PRP), was again centrifuged at 3000 rpm for 10 min to yield a platelet pellet with platelet poor plasma as the supernatant. The platelet pellet was re-suspended in PBS to a concentration of $4\times10^8$ platelets per mL. The MBG and Ga-MBGs were then exposed to the platelets and incubated at 37° C. for three different time intervals (15, 30, and 60 min). At the end of each time interval, the samples were removed and dip rinsed ten times in PBS to remove the platelets that are not attached. The samples were then placed into PBS containing 1% Triton X-100 for 1 h at 37° C. to lyse the adherent platelets. The number of platelets adhered on the surface of the materials was quantified by the LDH assay kit (Sigma-Aldrich, USA). A platelet calibration curve was obtained using serial dilutions of a known number of platelets by measuring optical density (OD) at 450 nm by an Epoch microplate spectrophotometer (BioTek; Winooski, Vt., USA). Each measurement was performed at least thrice. After the measurement of platelet adhesion, the interaction of platelets with MBG and Ga-MBGs was observed by FESEM (Quantat 250 FEG-FEI, USA) at 15 kV. In this regard, samples were fixed in 2.5% glutaraldehyde followed by dehydration in an ascending series of ethanol up to 100%. The samples were then dried in HMDS and coated with gold in a sputter coater for FESEM studies.

Antibacterial Efficacy:

Killing time assays were used to evaluate antibacterial efficacy of MBGs doped with various concentrations of $Ga_2O_3$ against *E. coli* and *S. aureus*.[30,31] Briefly, a suspension of *E. coli* or *S. aureus* was obtained from freshly grown colonies on tryptic soy agar after incubation at 37° C. overnight. 10 mL of the bacteria suspension ($4\times10^8$ CFU mL$^{-1}$) was added to each vial containing 3 mL of tryptic soy broth. Ga-MBGs that were previously sterilized under ultraviolet (UV) light for 12 h were then added and incubated at a temperature of 37° C. for 0, 1, 3, 6 and 12 h. After that, aliquots were taken at specified time intervals and, subsequently, serial dilutions of each bacterial culture were plated on agar plates to count the number of living bacterial colonies. Each evaluation was carried out in triplicate. The antibacterial activity was quantitatively estimated by the following relationship: $R(\%)=100\times[(B-C)/B]$, where R is the antibacterial activity (%), B is the mean number of survived bacteria on the control samples (CFU mL$^{-1}$), and C is the mean number of bacteria on the MBG and Ga-MBGs (CFU mL$^{-1}$). The MBG and pure LB broth culture were used as positive control and negative control, respectively. After 12 h incubation at 37° C., digital images of the plates were captured.

In Vitro Cytotoxicity Assays:

MBG and Ga-MBG samples, which were previously sterilized under UV light for 12 h, were soaked in 100 mL of DMEM, preheated to 37° C. After 24 h under sterile conditions, DMEM was filtered to separate MBG and Ga-MBGs, and these extracts were used as culture medium. To evaluate the effect of the bioactive glasses on cell viability, human dermal fibroblast (HDF) cells were seeded ($1 \times 10^4$ cells per well) in a 24-well plate and allowed to attach overnight. Then the cells were treated in the presence of different extracts obtained from MBG and Ga-MBGs. HDF cells without extract (treated with normal medium) were used as control. Each condition was set up in triplicate. Plates were assayed 1 and 3 days after the addition of extracts. The 3-(4,5-dimethylthiazol-2-yl)-2,5-diphenyl tetrazolium bromide (MTT) assay was used in this study to measure cell vitality and proliferation. The MTT agent (Biotium, Inc., Hayward, Calif.) reacts with its tetrazolium ring to produce blue formazan crystals in viable cells. At 1 and 3 days, the supernatant was removed from the wells, and the cells were rinsed three times with PBS to eliminate nonviable cells. 500 mL of fresh media were added to each well and then fifty microliters of the MTT solution (5 mg $mL^{-1}$ in PBS) were added in each well, and the cells were incubated at 37° C. for 4 h to allow the formation of formazan crystals. After incubation, the supernatant was removed, and 1 mL of dimethyl sulfoxide (DMSO) was then added to each well to dissolve the formazan crystals under continuous pipetting. The optical density was measured at a wavelength of 570 nm using a microplate reader. The results from three individual experiments were averaged and normalized to the control.

Statistical Analysis:

All data were expressed as mean±standard deviations of a representative of three experiments carried out in triplicate. The data were analyzed using statistical software (IBM SPSS Statistics for Windows, Version 22). In all the statistical evaluations, a value of $p<0.05$ was considered statistically significant.

II. Results (a) Structural and Morphological Characterization of MBGs

MBGs with different concentrations of $Ga_2O_3$ were successfully synthesized via EISA. The $N_2$ adsorption-desorption isotherms at 77 K of the synthesized samples were measured (FIG. 1(a)) together with the corresponding pore size distribution (FIG. 1(b)). The main textural parameters of the prepared samples are shown in Table 2. All the glasses revealed type IV isotherms along with H1 hysteresis loops, which are characteristic of a mesoporous structure and non-defective cylindrical pores, respectively (FIG. 1(a)).[32] FIG. 1(b) illustrates the pore size distribution curves as calculated from the adsorption branches by the BJH model. All of the samples exhibited very narrow pore size distributions centered between 5 and 7 nm.

TABLE 2

Textural parameters obtained by N2 adsorption-desorption at 77 K for MBG and Ga-MBGs

| Sample code | $Ga_2O_3$ content (mol %) | Surface area ($m^2 g^{-1}$) | Average pore diameter (nm) | Pore volume ($cm^3 g^{-1}$) |
| --- | --- | --- | --- | --- |
| MBG | 0 | 415 | 5.75 | 0.55 |
| 1% Ga-MBG | 1 | 509 | 6.34 | 0.78 |
| 2% Ga-MBG | 2 | 396 | 5.74 | 0.54 |
| 3% Ga-MBG | 3 | 340 | 6.65 | 0.52 |

As shown in Table 2, 1% Ga-MBG showed a higher surface area and pore volume compared with MBG and higher substituted Ga-MBGs. The pore structure of the samples with different $Ga_2O_3$ contents was investigated by SAXRD (FIG. 1(c)). All glasses exhibited two characteristic peaks at around $2\theta=1.1°$ and $1.8°$ that are associated with the ordered p6 mm hexagonal space group. The presence of these diffraction peaks indicated that the synthesized glasses have a high degree of hexagonal mesoscopic organization. However, 2 and 3% Ga-MBGs showed a weaker diffraction peak at around $2\theta=1.1°$ compared with MBG and 1% Ga-MBG. No evidence of residual crystallinity was observed in the WXRD pattern of the samples indicating that each glass is amorphous (FIG. 1(d)).

Figure 2:
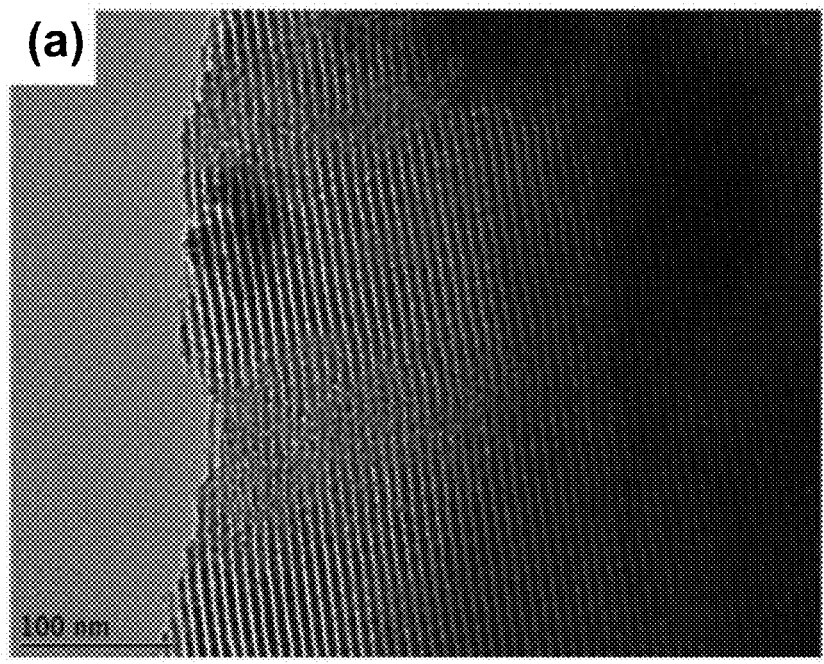
FIG. 2 shows transmission electron microscopy (TEM) images of the (a) MBG and (b) 1% Ga-MBG samples presenting their highly ordered mesoporous channel structure; scanning electron microscopy (SEM) images and the energy-dispersive X-ray spectroscopy (EDS) pattern of the MBG (c and d, respectively) and 3% Ga-MBG (e and f, respectively) samples; and (g) Fourier transform infrared (FT-IR) spectra of, from bottom to top, the MBG; 1% Ga-MBG; 2% Ga-MBG; and 3% Ga-MBG samples, indicating, from left to right by dotted ovals, Si—O—Si stretching, Si-non-bridging oxygens (NBO), Si—O—Si rocking and Si—O—Si bending. Scale bar in (a) and (b) is 100 nm. Scale bar in (c) and (e) is 50 μm.
Figure 2:
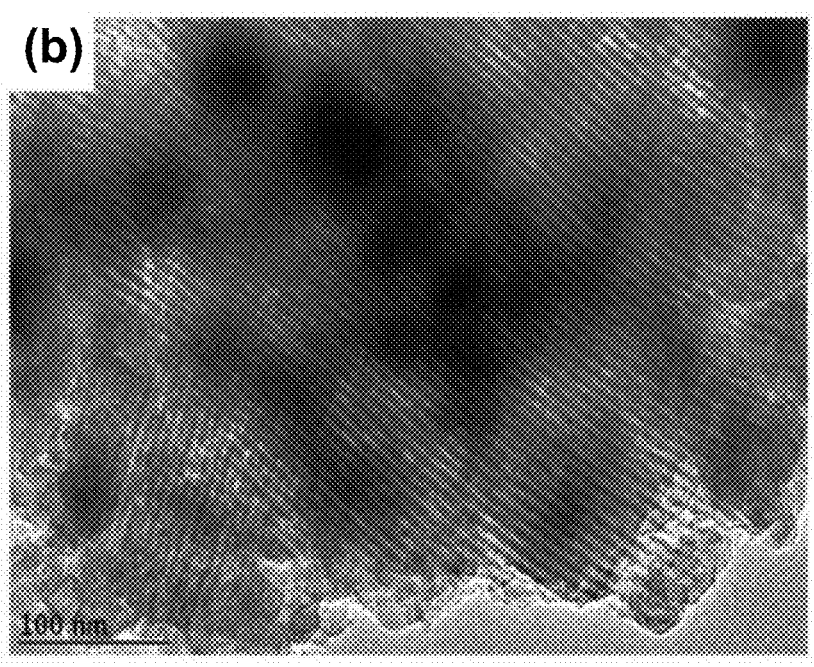
Figure 2:
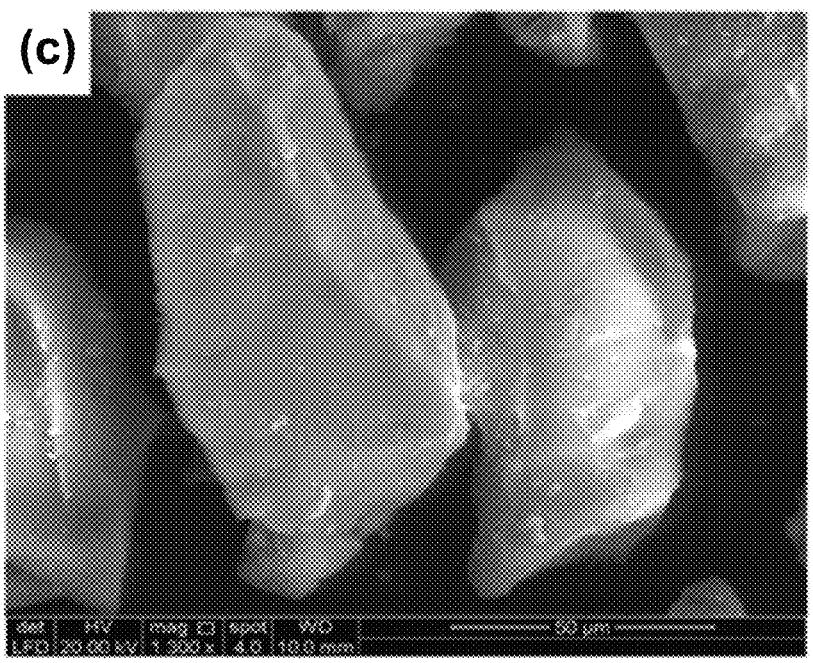
Figure 2:
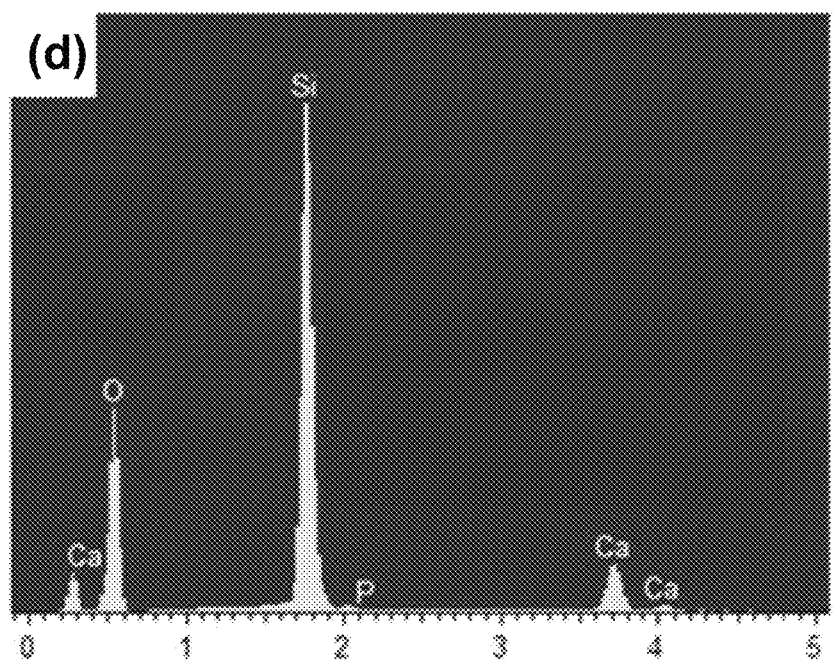
Figure 2:
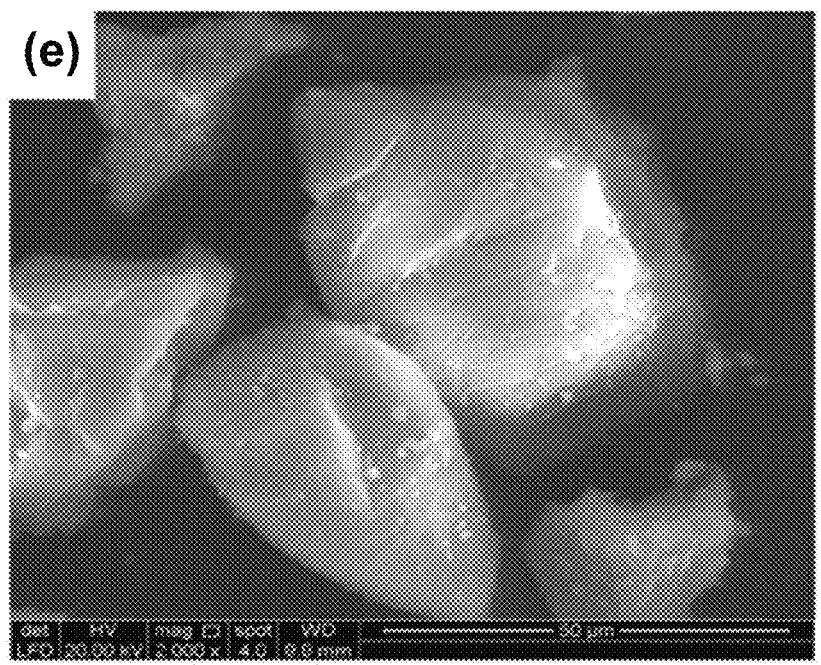
Figure 2:
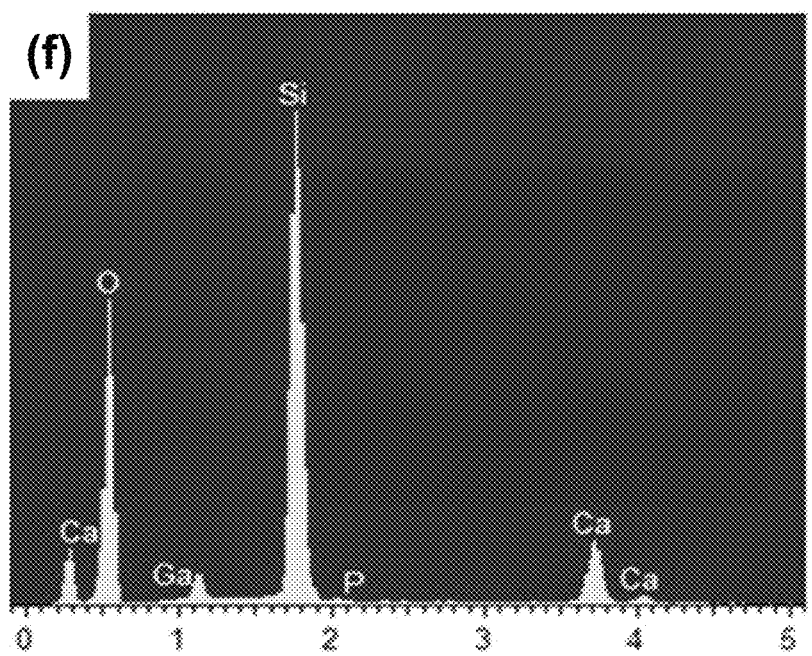
Figure 2:
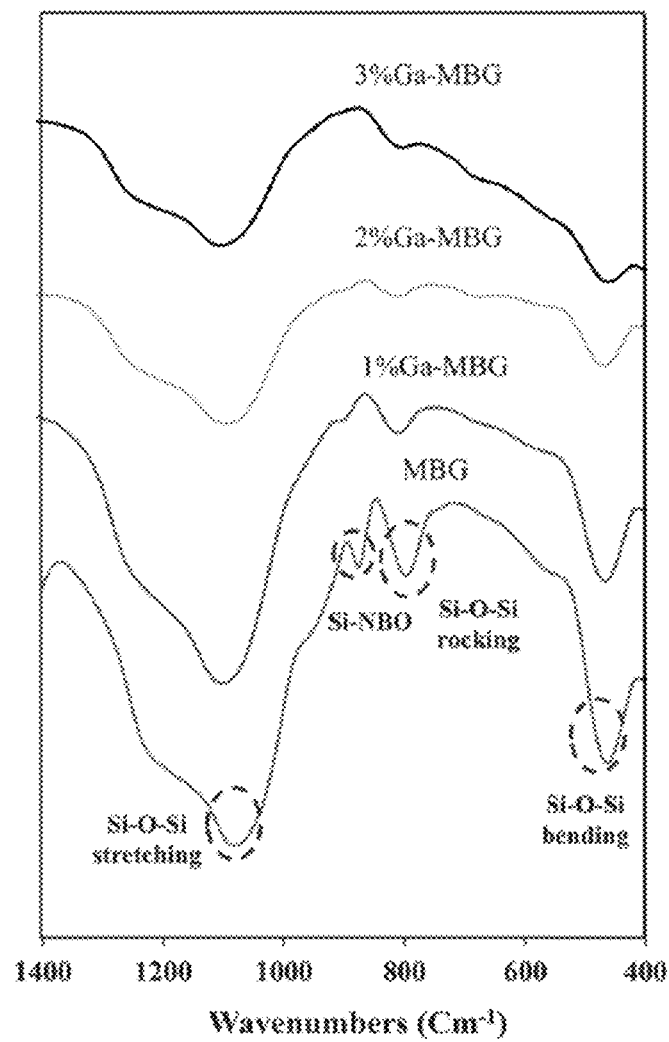

The presence of ordered mesoporous channels in the prepared glasses was also confirmed by TEM images. All synthesized glasses showed a typical 2D-hexagonal ordered mesoporous arrangement. The TEM images of the MBG and 1% Ga-MBG are presented in FIG. 2. Well-ordered pore arrays can be clearly observed in MBG (FIG. 2(a)) and 1% Ga-MBG (FIG. 2(b)) samples. However, the TEM images indicated a loss of order as the $Ga_2O_3$ content in the pores was increased (data not shown), confirming the results of SAXRD. The EDS analysis of the synthesized samples confirmed the presence of Si, Ca, P and Ga. The SEM morphologies and EDS spectra of the MBG (FIG. 2(c) and FIG. 2(d), respectively) and 3% Ga-MBG (FIG. 2(e) and FIG. 2(f), respectively) are also shown in FIG. 2. Based on the EDS results, the composition of the glasses were approximately similar to the theoretical value.

Evidence for the local structural changes with addition of different concentrations of $Ga_2O_3$ can be obtained from the FT-IR spectroscopy. FT-IR spectra of the MBG and Ga-MBGs are given in FIG. 2(g). All glasses presented two absorption peaks centered at around 1070 and 800 $cm^{-1}$ corresponding to the Si—O—Si asymmetric stretching mode and symmetric Si—O—Si stretching or vibration modes of the silica ring structures, respectively.[33,34] The peak at around 460 $cm^{-1}$ is also assigned to the Si—O—Si bending mode.[33] As can be seen in FIG. 2(g), the intensity of the 460, 800 and 1070 $cm^{-1}$ bands decreased with increasing $Ga_2O_3$ content up to 3 mol % indicating, while not wishing to be limited by theory, the depolymerizing role of $Ga^{3+}$ on the silicate network. Therefore incorporation of $Ga^{3+}$ into the MBG framework led to a decrement in the intensity of 460, 800 and 1070 $cm^{-1}$ absorption bands, thus confirming the formation of more non-bridging oxygen NBOs (corresponding to the 970 $cm^{-1}$ vibrational band). However, this band is not observed in 2% Ga-MBG and 3% Ga-MBGs due to the overlap with the broad Si—O—Si rocking peak.[35]

The zeta potentials of MBG and Ga-MBGs in PBS solution were measured in order to characterize their surface properties (Table 3).

TABLE 3

Zeta potential measured for the four MBGs prepared.

| Sample | Zeta potential (mV) in PBS at pH 7.4 |
| --- | --- |
| MBG | −30.4 |
| 1% Ga-MBG | −27.3 |
| 2% Ga-MBG | −26.2 |
| 3% Ga-MBG | −25.5 |

The surface of MBG was highly negative; the zeta potential was −30.4 mV, as a result of negatively charged silanol groups. In contrast to MBG, Ga-MBGs negligibly increased the zeta potential which can, while not wishing to be limited by theory, be attributed to the incorporation of $Ga^{3+}$.

(b) Ion Release and Degradability of MBG and Ga-MBGs in Tris-HCl Solution

Figure 3:
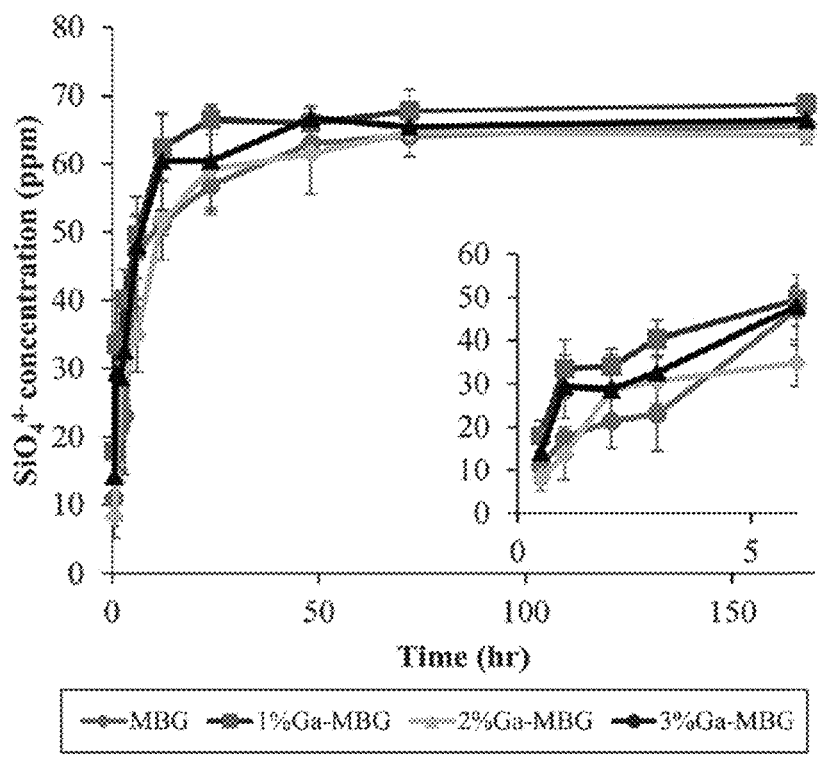
FIG. 3 shows the concentration variation of (a) $SiO_4^{4-}$, (b) $Ca^{2+}$, (c) $PO_4^{3-}$ and (d) $Ga^{3+}$ with the soaking time in hours in Tris-HCl solution. The inset in each plot shows the ion release profile of the ions during the first 6 h; and (e) the change of weight loss of MBG, 1% Ga-MBG, 2% Ga-MBG and 3% Ga-MBG samples in Tris-HCl solution as a function of time in days.
Figure 3:
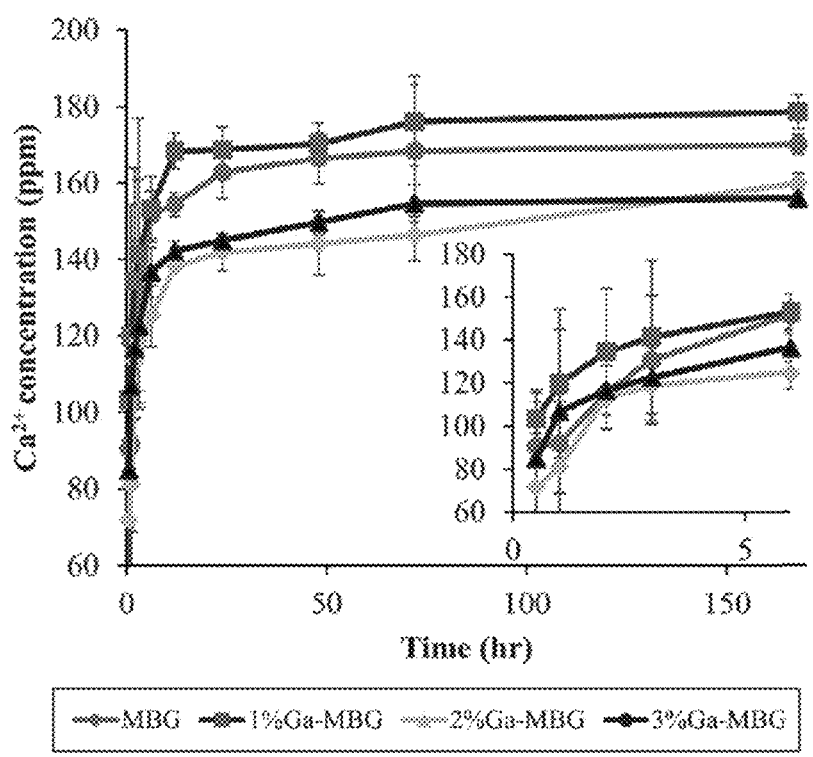
Figure 3:
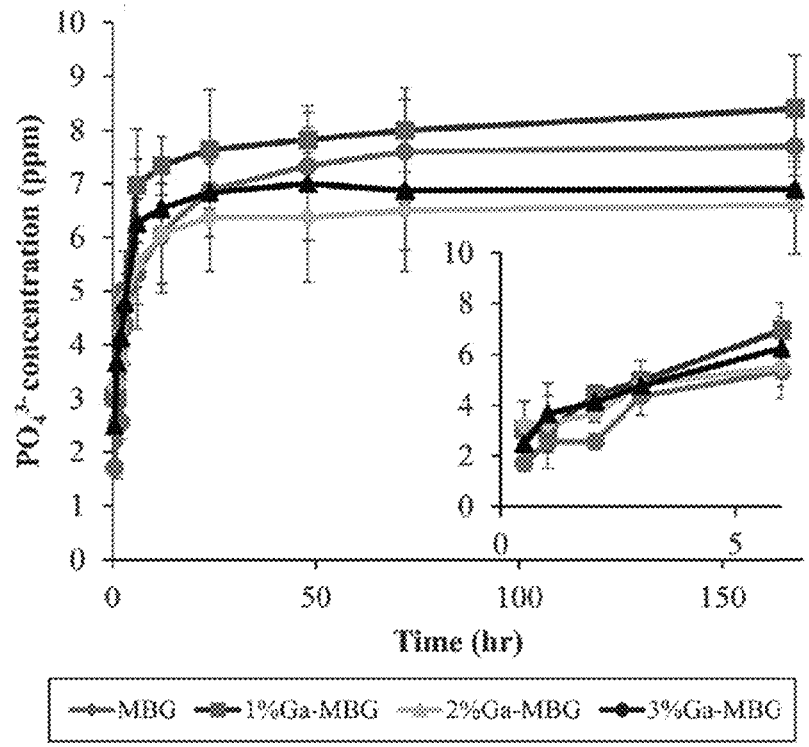
Figure 3:
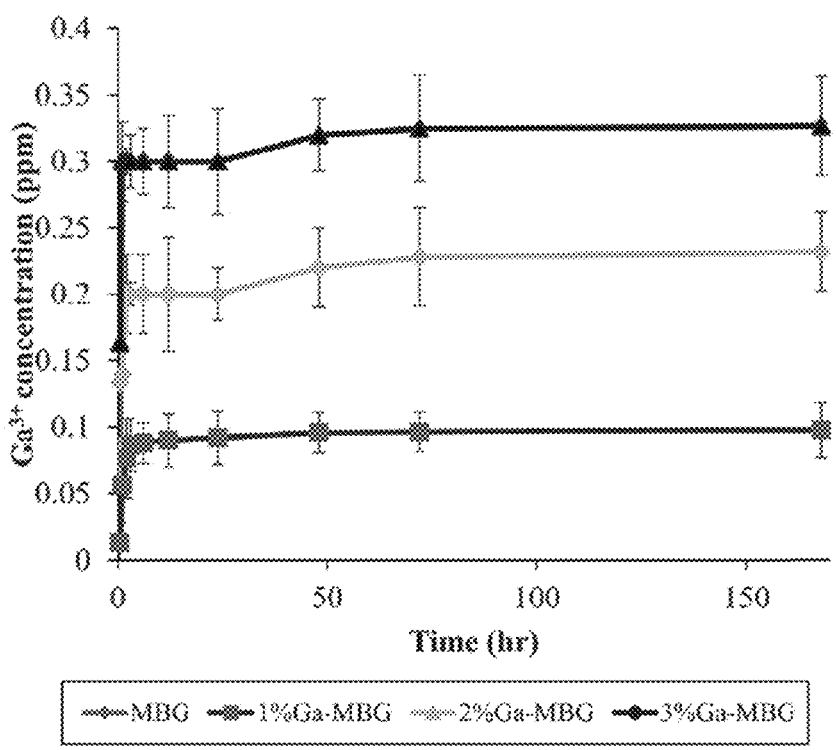
Figure 3:
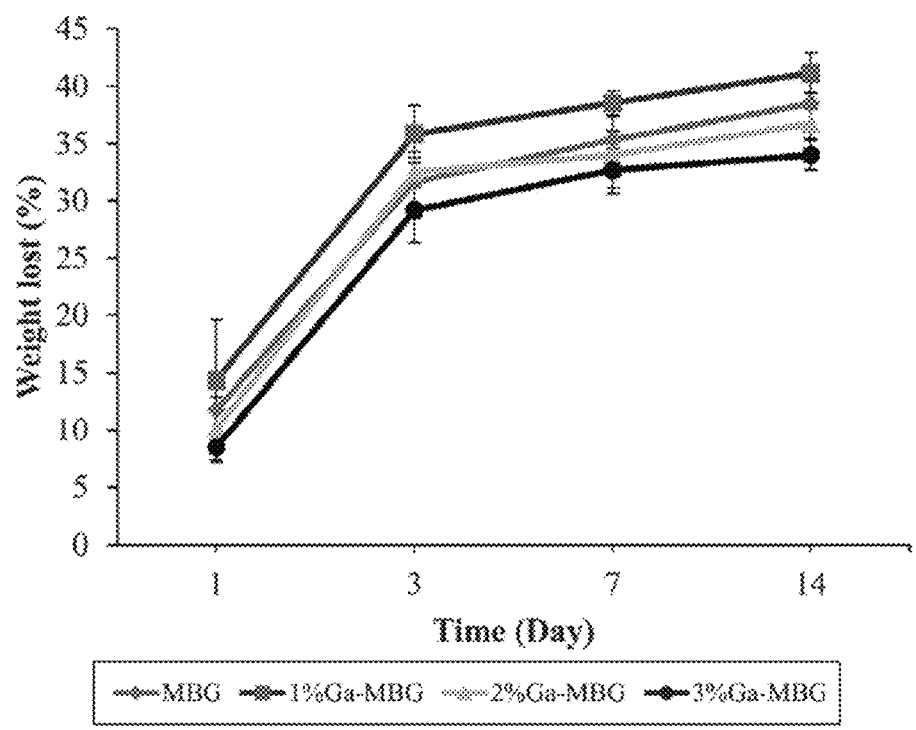

Changes in $SiO_4^{4-}$, $Ca^{2+}$, $PO_4^{3-}$ and $Ga^{3+}$ concentrations in Tris-HCl buffer solution after various soaking times are presented in FIG. 3. As can be observed in FIG. 3(a), the $SiO_4^{4-}$ concentration drastically increased in all samples during the first 48 h and then reached a steady state ranging from 60-70 ppm. A sharp increase in the $Ca^{2+}$ concentration was also detected during the first 72 h of the test for all samples (FIG. 3(b)). Nevertheless, the concentration of $Ca^{2+}$ for the glasses with higher $Ga_2O_3$ content (2% Ga-MBG and 3% Ga-MBG) was lower than that of MBG and 1% Ga-MBG. $PO_4^{3-}$ ion release profiles (FIG. 3(c)) of all the glasses also followed the same trend and increased up to 72 h, reaching values close to 6-8 ppm. Surprisingly, the concentration of the $PO_4^{3-}$ ions were higher for 1% Ga-MBG as compared with others. However, a different trend was found for $Ga^{3+}$ ion release in Ga-substituted MBGs (FIG. 3(d)). The $Ga^{3+}$ concentration increased after 3 h in the three Ga-containing samples and then experienced a steady state, reaching a value of 0.32 ppm in 3% Ga-MBG, that was approximately triple the amount found in 1% Ga-MBG. While not wishing to be limited by theory, the reason why leaching of $Ga^{3+}$ is low with respect to other ions is because of its high electric charge, which make it difficult to release from the glass network into the solution.[36] The concentration of $Ga^{3+}$ ions arrived to a steady state earlier than that of $SiO_4^{4-}$, $Ca^{2+}$, and $PO_4^{3-}$ concentration in the glasses. The in vitro degradation properties of the samples were also determined by testing the weight loss ratio of the samples after soaking in Tris-HCl solution for various times. As can be inferred from FIG. 3(e), the weight loss increased upon prolonged immersion up to 14 days for all the materials, and then negligibly increased or remained almost constant.

(c) Blood Coagulation Experiments

To study the effect of the MBG and Ga-MBGs on the blood coagulation process, the PT and APTT of the glasses at two different amounts (5 and 10 mg) were measured. The APTT test is used to investigate the intrinsic pathway of blood coagulation and PT is a test performed to investigate extrinsic pathway of blood coagulation. The APTT and PT results are shown in FIG. 4(a) and FIG. 4(b), respectively. The APTT results (FIG. 4(a)) revealed that all of the samples resulted in a significant activation of intrinsic pathways of the coagulation cascade since the values obtained for APTT were significantly diminished with respect to the negative control (blood without the sample). 1% Ga-MBG induced a somewhat more pronounced effect on the APTT value than that observed with other glasses. However, no significant dosage-dependent trends were observed in APTT values since increasing the amount of samples from 5 to 10 mg did not significantly decline the values of APTT (FIG. 4(a)). Additionally, at 5 mg there was no significant difference in the PT values of the glasses (FIG. 4(b)). All the glasses showed approximately the same effect on PT values of that of the negative control. However, in the case of the higher glass amount (10 mg), PT was prolonged.

(d) PBS Absorption Study In Vitro

The absorption capacity of the prepared samples was evaluated in vitro using PBS. The absorption ratios are presented in FIG. 5. The results revealed that the absorption coefficient of MBG with lowest $Ga_2O_3$ content (1% Ga-MBG) increased as compared with other glasses, which may be due to its outstanding textural properties (high surface area and pore volume).

(e) In Vitro Thrombus Formation

Figure 6:
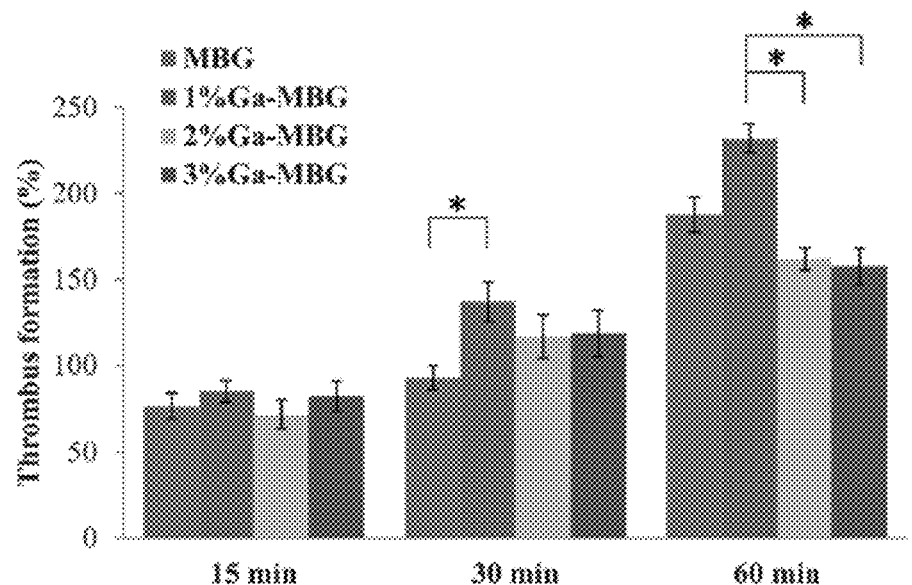
FIG. 6 shows (a) a plot of quantitative results of thrombus formation to the material surface after incubation times of 15, 30 and 60 minutes for, from left to right in each time: MBG, 1% Ga-MBG, 2% Ga-MBG and 3% Ga-MBG. * Indicates a significant difference, $p<0.05$; images of the blood clot formed on (b) MBG and (c) 1% Ga-MBG surfaces captured by a digital camera; field emission scanning electron microscope (FESEM) micrographs of red blood cell (RBC) agglutination and adhesion on the surface of (d) MBG after 30 minutes of incubation; and accumulated RBCs on (e) MBG surface under higher magnification (5000×); FESEM micrographs of RBC agglutination and adhesion on the surface of (f) 1% Ga-MBG glasses after 30 min of incubation; and accumulated RBCs on (g) 1% Ga-MBG surfaces under higher magnification (5000×). Many RBCs are trapped in a mesh of fibrin fibers and coalesced into thrombus on the 1% Ga-MBG surface. Scale bar in (d) and (f) is 50 μm. Scale bar in (e) and (g) is 20 μm.
Figure 6:
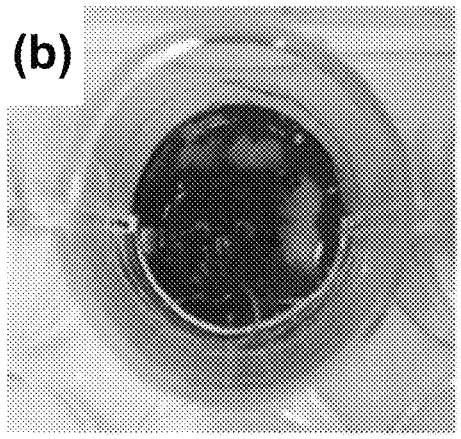
Figure 6:
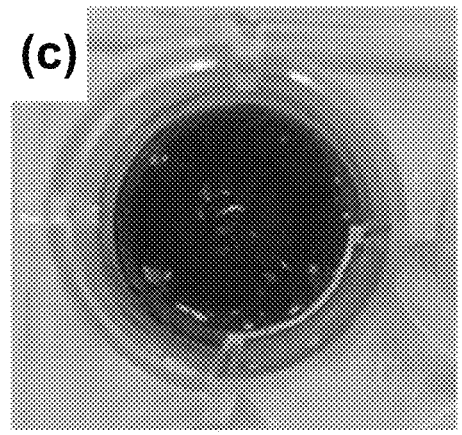
Figure 6:
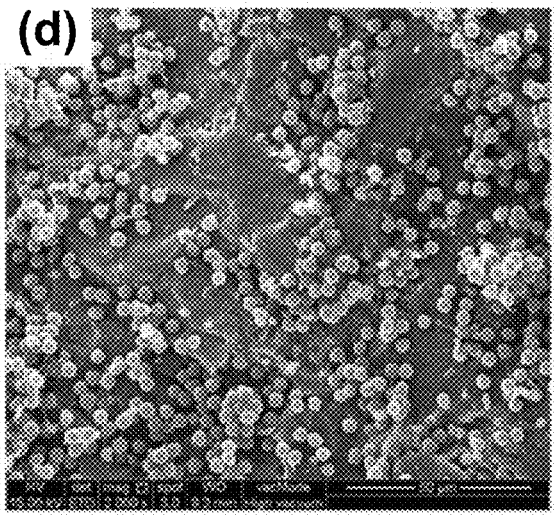
Figure 6:
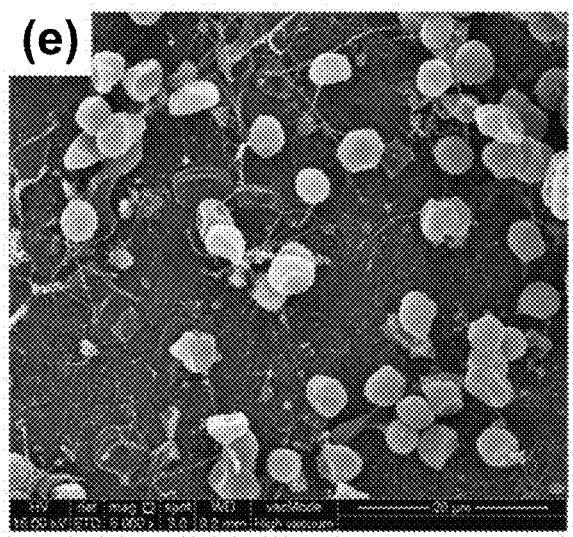
Figure 6:
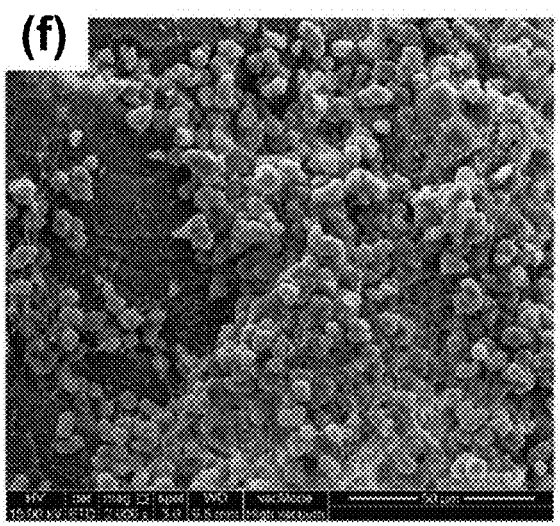
Figure 6:
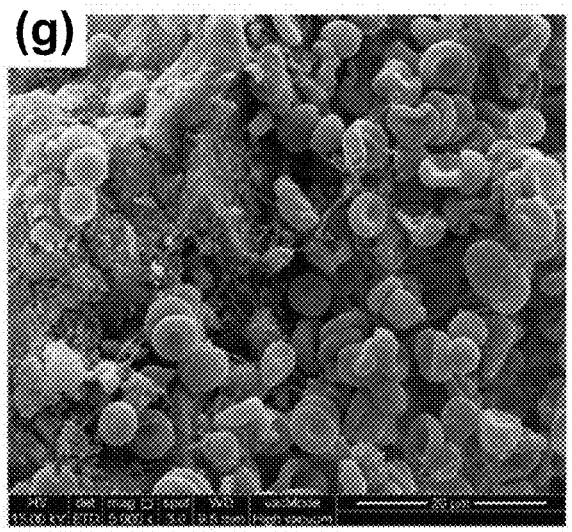

The effect of Ga-substituted MBGs in comparison with MBG on thrombus formation is shown in FIG. 6(a). In all cases, thrombus formation increased with incubation time. As observed from FIG. 6(a), the amount of thrombus formed was not significantly different between the groups during the initial 15 min. With increasing incubation periods up to 60 min, 1% Ga-MBG produced more thrombus in contact with blood than MBG, while not wishing to be limited by theory, indicating its higher thrombogenic activity. These results revealed the same trends as the blood coagulation experiments and PBS absorption studies. The digital image of MBG (FIG. 6(b)) and 1% Ga-MBG (FIG. 6(c)) also were in line with the results of the thrombus formation test. More red blood cells (RBCs) surrounded by a fibrin meshwork were aggregated on the 1% Ga-MBG surface with respect to MBG. The interaction of whole blood with MBG and Ga-MBGs was also seen by FESEM. FESEM images of both MBG (FIGS. 6(d) and (e)) and 1% Ga-MBG samples (FIGS. 6(f) and (g)) revealed that RBCs adhered onto their surface were dehydrated and aggregated, causing a change in cellular morphology.

More specifically, the RBCs on the 1% Ga-MBG surface (FIGS. 6(f) and (g)) seemed to form larger aggregates and coalesced into an erythrocyte plug trapped in the more extensive fibrin protein mesh with respect to MBG (FIGS. 6(d) and (e)), for which much fewer aggregates were observed on its surface. The images were in agreement with the results of thrombus formation measurements.

(f) Platelet Adhesion

Figure 7:
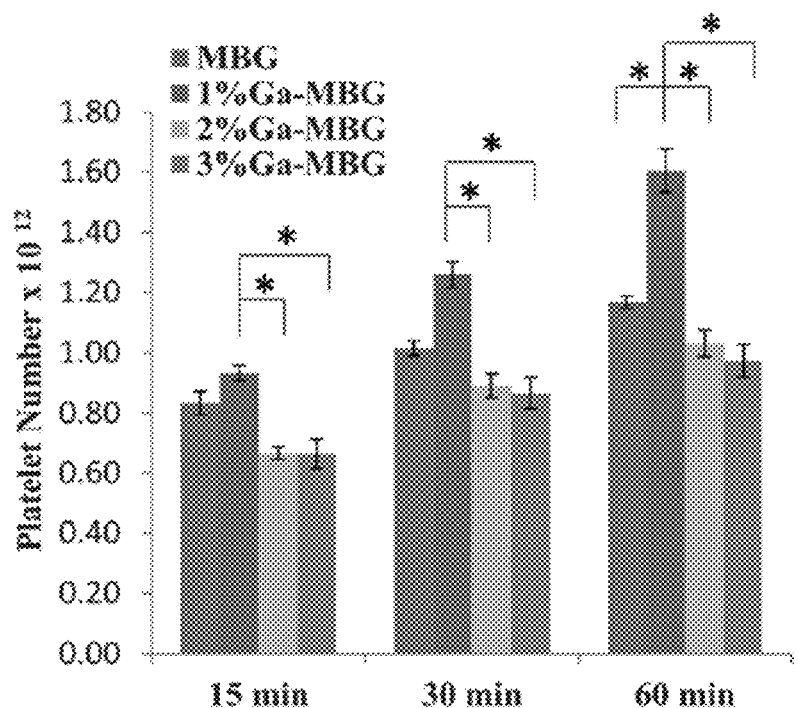
FIG. 7 shows (a) a plot of quantification of platelet adhesion on the MBG and Ga-MBGs at time points of 15, 30 and 60 minutes for, from left to right in each time: MBG, 1% Ga-MBG, 2% Ga-MBG and 3% Ga-MBG. * Represents a significant difference, $p<0.05$; and SEM images of platelets adhered on the glasses: (b) MBG, (c) 1% Ga-MBG, and (d) higher magnification image of (c). Scale bar in (b) is 5 μm; scale bar in (c) is 3 μm; and scale bar in (d) is 2 μm.
Figure 7:
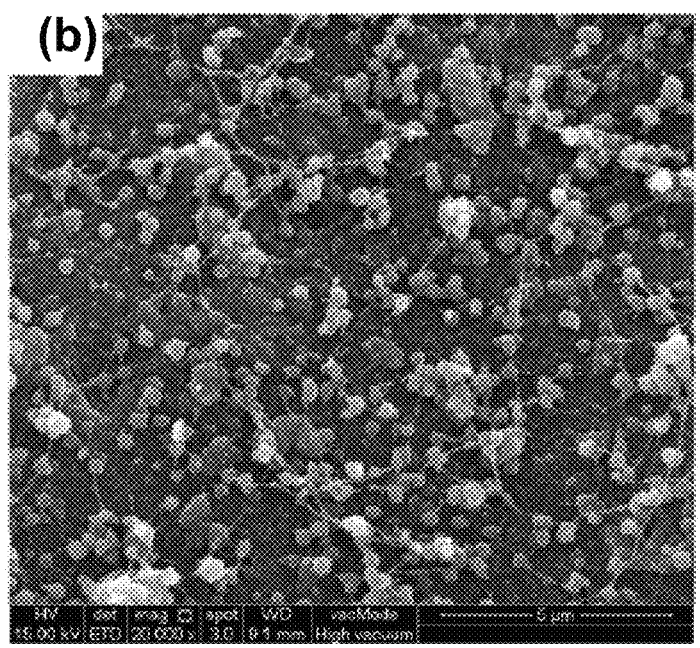
Figure 7:
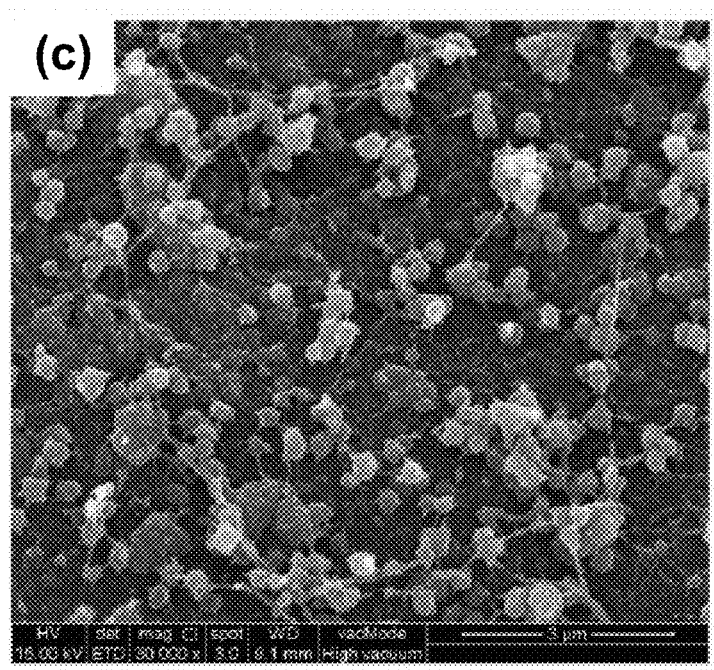
Figure 7:
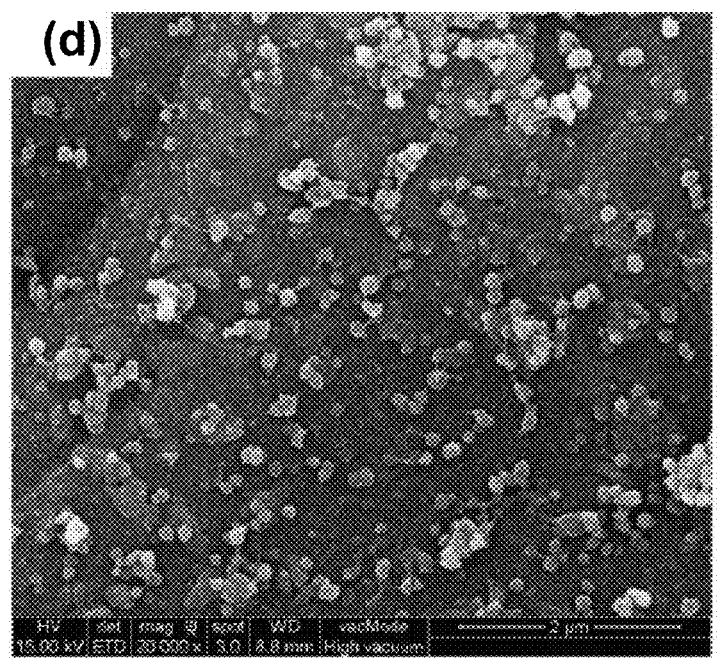

To assess the ability of Ga-substituted MBGs in enhancing platelet adhesion and aggregation in vitro, the synthesized materials were mixed with platelet suspensions for three time intervals (15, 30 and 60 min), and platelet adhesion was quantitatively measured using an LDH assay kit. FIG. 7 shows the qualitative and quantitative results of platelet adhesion on MBG and Ga-MBGs.

It can be seen from the results (FIG. 7(a)) that all the synthesized materials were able to significantly increase the number of adherent platelets at different time intervals. After 15 min incubation, no significant differences were found in the numbers of adherent platelets to the surfaces of the four types of glass studied. Most changes in the platelet number occurred during the subsequent 30 and 60 min. As compared with non-Ga-containing MBG, 2% Ga-MBG and 3% Ga-MBG, numerous platelets adhered on the surface of 1% Ga-MBG after 30 and 60 min incubation with PRP. However, the results showed an almost negligible increment in the number of platelets adhered onto the surface of other glasses with increasing incubation time. The FESEM also confirmed the significant ability of the 1% Ga-MBG to initiate platelet aggregation (FIGS. 7(b) and (c)) after 30 min of incubation with PRP. The images show that the 1% Ga-MBG surface was covered with more platelets alongside silky fibrin than MBG (FIG. 7(d)), and also many pseudopodia were observed on the surface of 1% Ga-MBG, implying, while not wishing to be limited by theory, higher activation and aggregation of platelets. By contrast, less platelet adhesion and fibrin formation occurred on the surface of non-Ga-containing MBG (FIG. 7(d)).

(g) Antibacterial Activity

Figure 8:
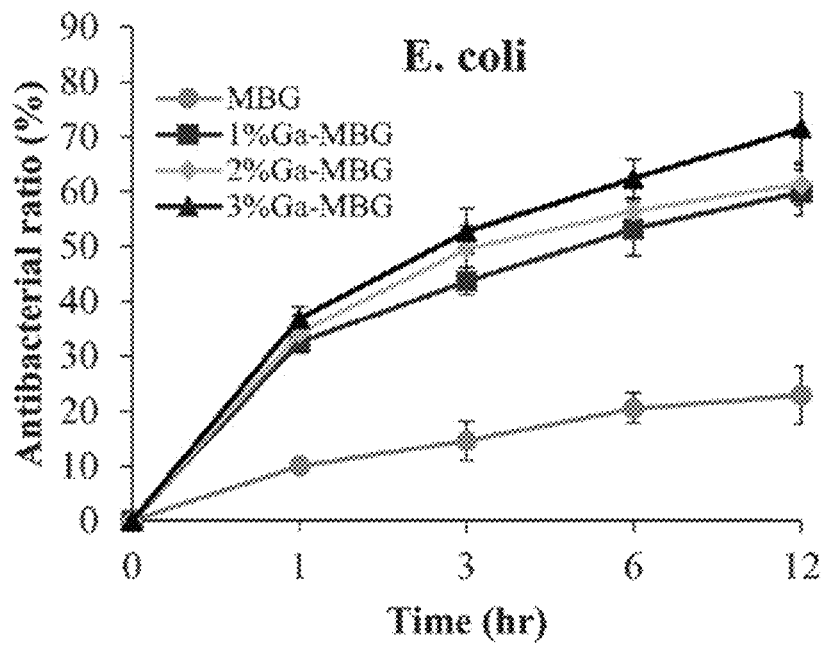
FIG. 8 shows plots of bacteriostatic efficacies (antibacterial ratio as a function of time in hours) of MBG and Ga-MBGs (1, 2 and 3 mol %) against (a) *Escherichia coli* (*E. coli*) and (b) *Staphylococcus aureus* (*S. aureus*); digital images representing the bacterial culture plates of (c) *E. coli* upon exposure to (c) the negative control and (d) 3% Ga-MBGs; and digital images of the bacterial culture plates of *S. aureus* treated with (e) the negative control and (f) 3% Ga-MBG.
Figure 8:
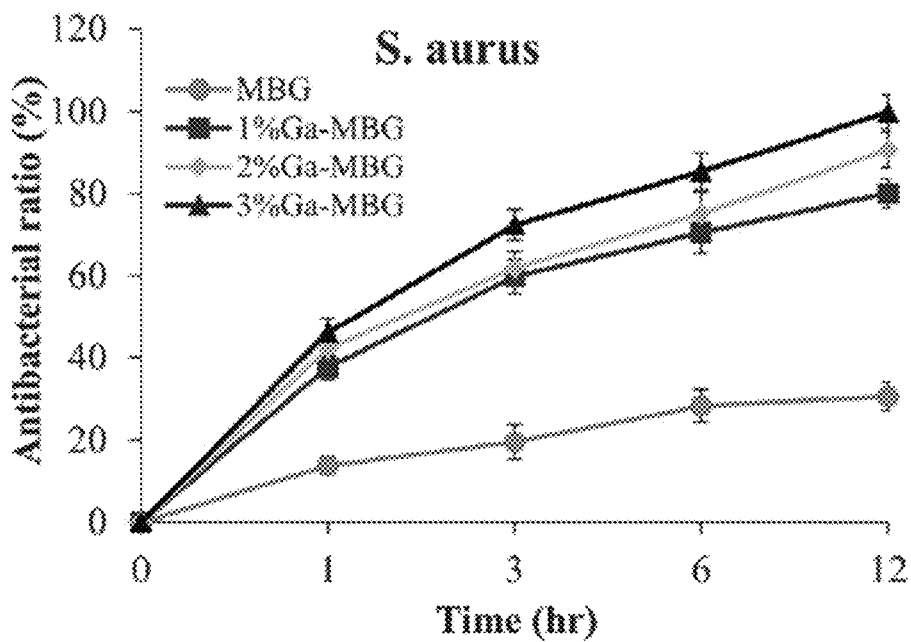
Figure 8:
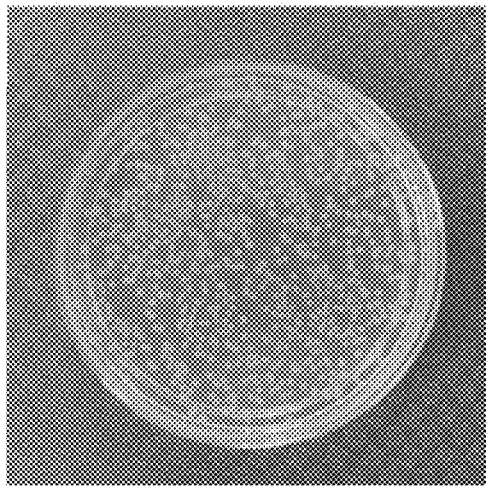
Figure 8:
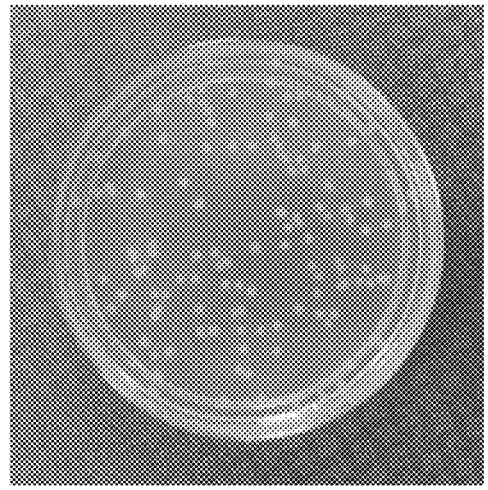
Figure 8:
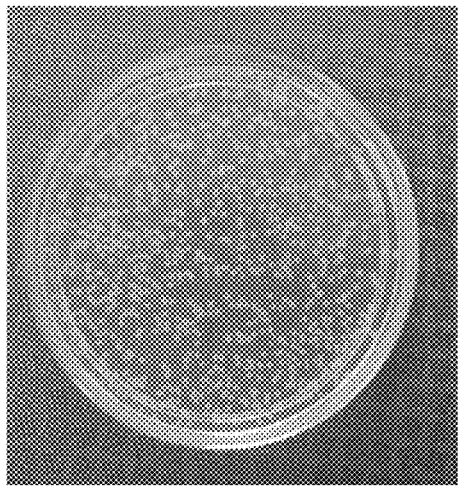
Figure 8:
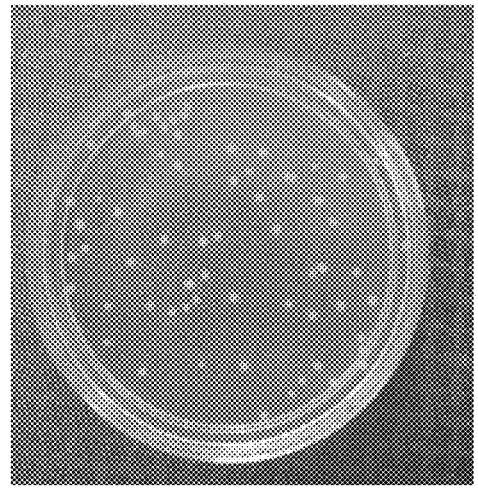

The antibacterial activity of Ga-MBGs was compared with that of non-Ga-containing MBG against both *E. coli* and *S. aureus* over 12 h as shown in FIG. 8(a) and FIG. 8(b). Ga-MBGs demonstrated a potent antibacterial effect against both pathogens which can, while not wishing to be limited by theory, be attributed to the presence of $Ga^{3+}$, since MBG did not impart a significant antibacterial effect. While not wishing to be limited by theory, the increase in pH resulting from ion release in the solution is considered a possible antibacterial mechanism of MBG. The antibacterial efficacy of Ga-MBGs against both *E. coli* and *S. aureus* increased with $Ga_2O_3$ content over time. FIG. 8(a) shows that 3% Ga-MBG exerted higher antibacterial activity against *E. coli* compared to MBGs with lower $Ga_2O_3$ content (1% Ga-MBG and 2% Ga-MBG) and achieved significant reduction in the number of viable cells within 12 h (FIG. 8(a)). However, differences between the antibacterial effect of 1% Ga-MBG and 2% Ga-MBG were not significant. In the case of *S. aureus* (FIG. 8(b)), 3% Ga-MBG had slightly more inhibitory effect compared to 1% Ga-MBG and 2% Ga-MBG, reaching its antibacterial rate of 99% at 12 h. FIG. 8 also presents images of colonies of *E. coli* (FIG. 8(c) and FIG. 8 (d)) and *S. aureus* (FIG. 8(e) and FIG. 8(f)) incubated on agar plates obtained from cultured suspensions with negative control and 3% Ga-MBG. An obvious reduction was detected in the population of the *E. coli* colonies after exposure to the 3% Ga-MBG for 12 h (FIG. 8(d)) compared with the negative control (FIG. 8(c)). A more pronounced reduction in *S. aureus* colonies was also seen upon exposure to 3% Ga-MBG (FIG. 8(f)) in comparison to the negative control (FIG. 8(e)). Ga-MBGs displayed a more significant antibacterial impact against *S. aureus* than against *E. coli*.

(h) Cytotoxicity Effects

Figure 9:
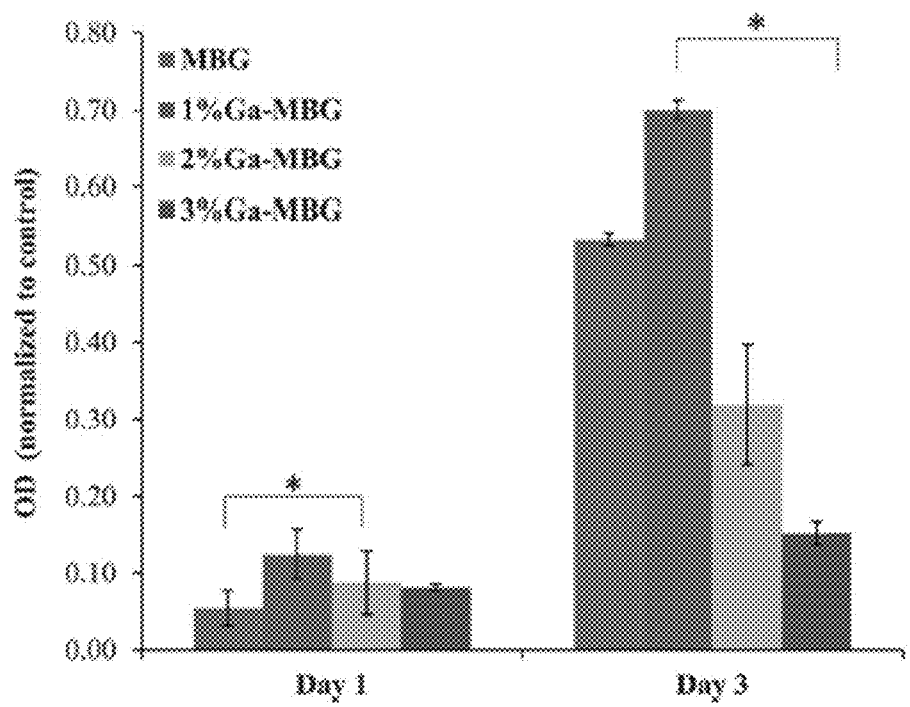
FIG. 9 shows a plot of viability of fibroblast cells after 1 day and 3 day exposure to the extracts obtained from MBG (far left at each time) and Ga-MBGs (from right to left at each time: 3% Ga-MBG, 2% Ga-MBG and 1% Ga-MBG). Data were obtained using MTT assay. * Represents a significant difference, $p<0.05$.

To study the biocompatibility of the MBG and Ga-MBGs, cell viability of HDF cells was evaluated after they were treated with extracts of the bioactive glasses for 1 and 3 days. The MTT assay (FIG. 9) indicated that the cell viability of HDF cells in the presence of the MBG and Ga-MBG extracts increases with culture time, suggesting, while not wishing to be limited by theory, that all glasses were non-cytotoxic to HDF cells. In comparison to the control, a slightly higher cell viability was noted for all MBG materials at day 1. However, a significant increase in cell numbers for all the materials was observed after 3 days when compared to the control. The increment in the cell viability was more pronounced in the presence of 1% Ga-MBG.

III. Discussion

Much attention has been focused on the fabrication of inorganic mesoporous materials as a new generation of inorganic hemostats that may be able to overcome shortcomings associated with commercial inorganic hemostats such as QC and QCG. Whilst some reports highlight the hemostatic performance and antibacterial properties of MBGs,[28(a),28(b),31] more studies are needed to clarify the hemostatic properties and antibacterial activity of these materials.

Figure 4:
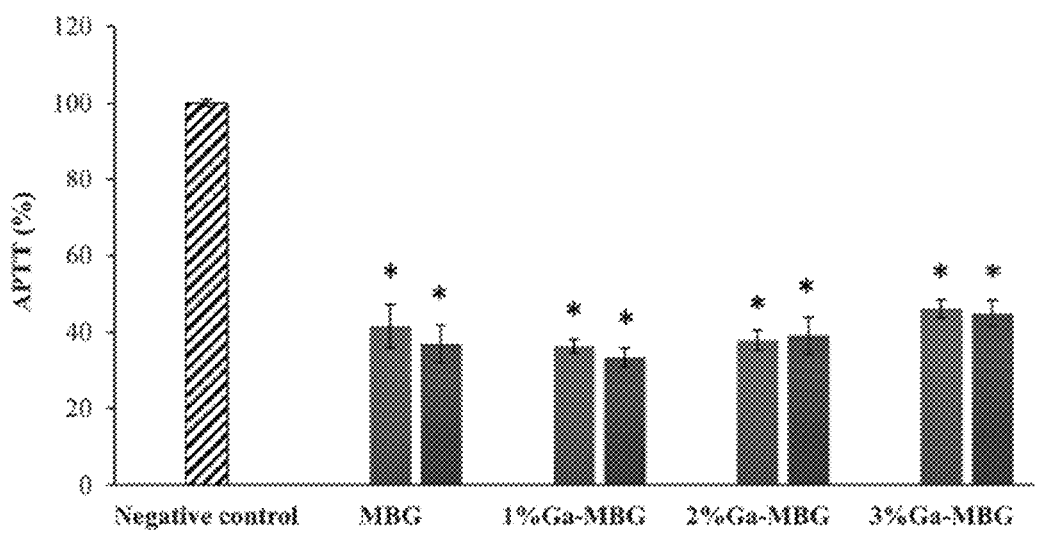
FIG. 4 shows the influence of MBG and Ga-MBGs on (a) activated partial thromboplastin time (APTT) and (b) prothrombin time (PT) of human plasma. From left to right in each plot: negative control, 5 mg MBG, 10 mg MBG, 5 mg 1% Ga-MBG, 10 mg 1% Ga-MBG, 5 mg 2% Ga-MBG, 10 mg 2% Ga-MBG, 5 mg 3% Ga-MBG, 10 mg 3% Ga-MBG. * Represents a significant difference with respect to negative control at $p<0.05$.
Figure 4:
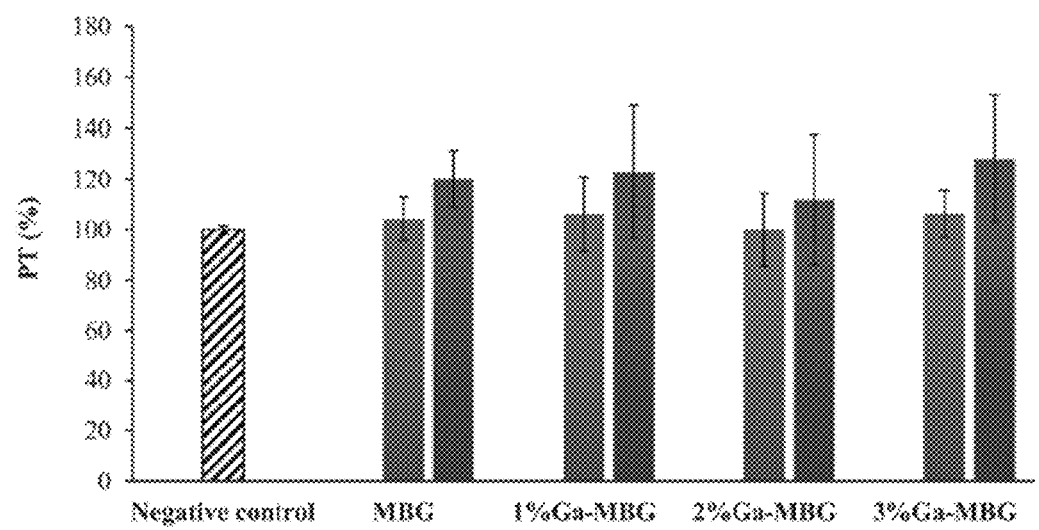

Hemostasis is a complex physiological process that prevents blood loss and proceeds via the synchronized action of three mechanisms including vasoconstriction, formation of a platelet plug and blood coagulation.[3] So, the hemostatic agents that perform their task by accelerating one or more of the processes above can be of help in achieving hemostasis. There are multiple mechanisms underlying MBG and Ga-MBGs' hemostatic properties. Based on the obtained results in the coagulation assays, it was observed that, unlike the extrinsic pathway that was insignificantly affected by the bioactive glasses, the intrinsic coagulation pathway was considerably accelerated in the presence of the synthesized materials with respect to the negative control (FIG. 4). The accelerated coagulation response induced by the synthesized samples can depend on multiple factors. In detail, both MBG and Ga-MBGs, due to possessing mesoporous interconnected structures with large specific surface area, can act as factor concentrators and share a mechanism of action similar to QC. Such materials capture and store large volumes of water within their pores resulting from the electrostatic interaction with $Ca^{2+}$ ions residing in their pores. These interactions lead to the hyperconcentration of coagulation factors and other protein and cellular components of the plasma that in turn would accelerate the coagulation cascade and the subsequent fibrin clot formation. However, a prolonged APTT was observed with increasing $Ga_2O_3$ content in the MBG network (e.g., for 3% Ga-MBG) in comparison with MBG (FIG. 4). While not wishing to be limited by theory, this prolonged effect of MBG with higher $Ga_2O_3$ content on APTT values can be related to deterioration of the hexagonal ordered structures of the MBG, which decreases its textural properties (specific surface area and pore volume) and subsequently reduces its water absorption coefficient.

Figure 5:
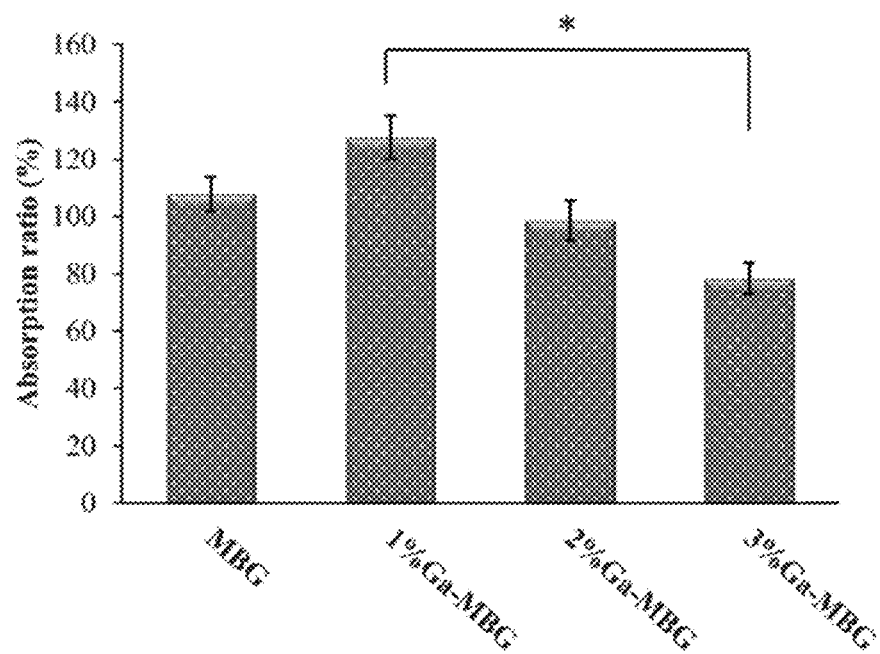
FIG. 5 shows phosphate buffered saline (PBS) absorption ratio of MBG (far left) and Ga-MBG samples (from right to left: 3% Ga-MBG, 2% Ga-MBG and 1% Ga-MBG). * Indicates that the difference between the absorption ratios of 1% Ga-MBG and 3% Ga-MBG was statistically significant (*$p<0.05$).

In contrast to 3% Ga-MBG and other prepared bioactive glasses, a shortening of the APTT occurred as a result of adding MBG with lowest $Ga_2O_3$ content (1% Ga-MBG), which can be attributed to its outstanding textural properties. The 1% Ga-MBG surface, due to its larger specific surface area (509 $m^2$ $g^{-1}$) and pore volume (0.78 $cm^3$ $g^{-1}$), serve plenty of spaces resulting in greater permeability of the water molecules to their pores and subsequent blood clot formation. Accordingly, the mesoporous structure of the MBG materials plays a pronounced role in the activation of the intrinsic pathway. These results were consistent with the PBS absorption results: indeed, the 1% Ga-MBG sample was superior to all other synthesized glasses in water absorption ability (FIG. 5).

Another favorable factor that contributes to the hemostatic function of the glasses can be related to their potent procoagulant activity resulting from their negative surface charge. The presence of the negative charge on the surface of all synthesized materials was confirmed by zeta potential measurements (Table 3). The synthesized materials exhibited significant negative zeta potential in PBS at pH 7.4. While not wishing to be limited by theory, when the bioactive glasses come in contact with body fluids, a unique surface reaction occurs including rapid ion exchange reactions between the glass network modifiers with $H^+$ (or $H_3O^+$) ions from the solution.[37,38] This reaction leads to hydrolysis of the silica groups, subsequent formation of silanol (Si—OH) groups on the glass surface and, eventually, the production of a negatively charged surface with functional groups (Si—$O^-$).

The presence of $Ca^{2+}$ in the glass network also plays a role in its procoagulant action. The synthesized materials have ability to present $Ca^{2+}$ to blood, which speeds up the intrinsic pathway of blood coagulation. $Ca^{2+}$ (known as clotting factor IV) is a cofactor that plays a ubiquitous role in the coagulation cascade. It is involved in the immobilization and orientation of clotting enzymes on cellular surfaces, serving as the ionic bridge between two negatively charged residues (such as the cellular surface and clotting factors). It also serves as a required co-factor for several enzymatic reactions, including conversion of prothrombin to thrombin, the enzyme that aids in the generation of insoluble fibrin from the soluble fibrinogen. $Ca^{2+}$ ions are also consumed during splitting fibrinogen into fibrin monomers and polymerization of monomers into a fibrin strand and, eventually, lead to crosslinking and formation of ticker fibrin strands. Indeed, they act as an adhesive to hold the fibrin monomers to each other to form the polymeric fibrin fibers.

Hence, $Ca^{2+}$ availability in the MBG framework is another factor favorable to the activation of the intrinsic pathway and subsequent shortened APTT.

Comparing the results from the ion release study and coagulation assay indicated a very close correlation between shortened APTT and $Ca^{2+}$ release profiles so that 1% Ga-MBG, having a higher capability to release $Ca^{2+}$ than other glass formulations, led to the further reduction of APTT. Contrary to what occurs in conventional glasses (melt and sol-gel bioactive glasses), where a higher amount of network modifier leads to lower network connectivity, a rapid ion exchange and a subsequent rapid ion release, mesoporous bioactive glasses do not apparently exhibit the same trend. Here, it was observed that an increase in the $Ga_2O_3$ content provoked a decrease in the release rate of the ions, which is evidenced by MP-AES results. While not wishing to be limited by theory, the incorporation of a higher amount of $Ga^{3+}$ into MBG disrupts the order of the mesostructure, resulting in a decrement of the textural properties, which are parameters to produce a unique ion release profile in the mesoporous bioactive glasses. Therefore, the lower $Ca^{2+}$ release rate of the 3% Ga-MBG system was considered, while not wishing to be limited by theory, to be a cause of APTT prolongation. On the contrary, in the case of 1% Ga-MBG, with the lowest $Ga_2O_3$ content and textural properties (higher specific surface area and pore volume), the $Ca^{2+}$ release profile evidenced that, just after 0.5 h immersion in Tris-HCl solutions, a substantial amount of $Ca^{2+}$ (~103 ppm) was released. While not wishing to be limited by theory, these results could be explained as owing to the synergy of both the low $Ga_2O_3$ content (1 mol %) and high specific surface area (502 $m^2 g^{-1}$), which provoked a larger $Ca^{2+}$ release, necessary for the activation of the intrinsic pathway.

While not wishing to be limited by theory, a reason why 1% Ga-MBG despite lower $Ga_2O_3$ content is a stronger activator of the coagulation cascade compared to the other samples can be attributed to the synergy of both its intrinsic textural and structural features alongside the presence of $Ga^{3+}$.

Besides the role of the glasses in the activation of the intrinsic pathway, they were also found to be effective in thrombus formation and platelet aggregation. From the results of thrombus formation assay in FIG. 6, distinct amounts of thrombus were noted on four MBGs, in particular on the 1% Ga-MBG surface. Unlike typical clotting which is composed of a platelet plug and a mesh of cross-linked fibrin protein, the unique blood clot formed by MBG materials also consisted of a homogenous layer of RBCs that are stuck in the fibrin mesh to form a clot. While not wishing to be limited by theory, two main factors, including the silanol-rich surface of MBGs that bind with the phosphatidyl choline-rich RBC membrane[39] and the large surface area and pore volume of the glasses that provide more lattice to trap cellular and blood plasma components, are involved in this process. Hence, while not wishing to be limited by theory, a possible explanation for the higher thrombogenic potential of 1% Ga-MBG is attributed to its higher surface area that increases the accessibility of silanol groups to the blood cells, leading to the production of a stable hemostatic clot.

These results were consistent with those of the platelet adhesion assay. 1% Ga-MBG enhanced the platelet adhesion and activation compared to other glasses, since a large number of platelets were detected on its surface with spread morphology and protruding pseudopodia. While not wishing to be limited by theory, a larger surface area in 1% Ga-MBG served as a favourable surface for interaction with platelets and fibrinogen, causing clumping and activation of platelets. Likewise, the $Ca^{2+}$ ions that are released from the synthesized materials can contribute to platelet activation, since they accelerate the production of the proteolytic enzyme thrombin. Thrombin is a serine protease that stimulates platelet activation and aggregation through activation of protease-activated receptors on the platelet cell membrane.[40]

The major concern with known inorganic hemostats such as QC and Woundstat (WS, a Smectite clay) is related to their nonbiodegradability, which can lead to thrombosis in distal organs such as brain and lungs.[40a] Here, the degradation ability of MBG and Ga-MBGs was assessed after immersion in Tris-HCl solution over time. 1% Ga-MBG showed a more pronounced degradation over 14 days compared with other glasses and lost about 32% of its initial weight after soaking for 14 days. While not wishing to be limited by theory, the faster degradation rate of 1% Ga-MBG is probably due to its quick dissolution.

In addition to assessing the hemostatic functions of the prepared bioactive glasses, their antibacterial properties and biocompatibility were investigated, since infection and cellular toxicity at the site of bleeding are other challenges faced by hemostatic agents. Based on the results of the antibacterial activity, incorporation of $Ga^{3+}$ into the MBG framework resulted in a faster and more potent bacteriostatic action than non-Ga-containing MBG against both pathogens that were tested. As compared to both pure LB broth culture and MBG, 3% Ga-MBG had a significant inhibitory effect on the growth of both *E. coli* and *S. aureus* in time-kill assays, in particular at 12 h. Moreover, 1% Ga-MBG and 2% Ga-MBG samples exhibited more bacteriostatic activity with respect to either pure LB broth culture or MBG. These results were in good agreement with the $Ga^{3+}$ release profile from the glass network (FIG. 3). Although $Ga^{3+}$ had a slower release rate than other ions, it achieved a significant antibacterial effect.

MBG also demonstrated slight antibacterial activity against the two bacterial strains considered in this work. While not wishing to be limited by theory, this could be due to the change in pH (data not shown) during the glass degradation, as observed in Tris-HCl.

$Ga^{3+}$ does not appear cytotoxic to HDF cells as its release was maintained well below the toxicity level (14 ppm).

In short, the synergistic effect of all the factors presented above, including chemical activation and physical absorption, promote the blood coagulation cascade and render Ga-MBG materials very suitable hemostatic materials. Among the samples, 1% Ga-MBG exhibited the best overall performance.

IV. Conclusions

In the present study, Ga-MBG materials have been produced which are useful for hemostatic application and their antihemorrhagic effect alongside biocompatibility and antibacterial properties were evaluated.

Example 2: Comparative Efficacy of Haemorrhage Control of a Novel Mesoporous Bioactive Glass Versus Two Commercial Hemostats In Example 1, MBGs substituted with three different concentrations of $Ga_2O_3$ (1, 2 & 3 mol %) for staunching bleeding were developed. It was found that the $Ga_2O_3$ content in the MBG framework can affect the rate of blood clot formation in vitro. MBG containing 1 mol % $Ga_2O_3$ with high surface area and pore volume was shown to promote hemostasis compared to the Ga-free MBG. Accordingly, an objective of this example is to compare the in vitro hemostatic response of this new inorganic coagulation accelerator, 1% $Ga_2O_3$-containing mesoporous bioactive glass (1% Ga-MBG), against two commercially available hemostatic agents, Celox (CX) and QuikClot Advanced Clotting Sponge Plus ($ACS^+$).

I. Materials and Methods (a) Materials

Nonionic triblock copolymer $EO_{20}PO_{70}EO_{20}$ (P123), Tetraethyl orthosilicate (TEOS, 98%,) triethylphosphate (TEP, 99.8%), calcium nitrate tetrahydrate, $(Ca(NO_3)_2 \cdot 4H_2O$, 99%), gallium(III) nitrate hydrate $[Ga(NO_3)_3 \cdot xH_2O$, 99.9%), ethyl alcohol (EtOH) and nitric acid ($HNO_3$) were all purchased from Sigma-Aldrich (USA). The chemicals were of reagent grade and used as purchased. CX and $ACS^+$ were also purchased from their respective commercial sources. Both FDA approved products are available for purchase without prescription. $ACS^+$ beads were removed from the porous bag that they were supplied in and were used in their bead form for all the tests.

(b) Preparation of 1% Ga-MBG

MBG (80–x) % $SiO_2$-15% CaO-5% $P_2O_5$ substituted with $xGa_2O_3$ (1 mol %) was synthesized following the procedure described in Example 1. Briefly, TEOS, TEP, Ca $(NO_3)_2 \cdot 4H_2O$ and Ga $(NO_3)_3 \cdot xH_2O$ were added to a P123-ethanol mixture followed by the addition of 1.0 mL $HNO_3$. The reaction mixture was allowed to stir at room temperature overnight and the resulting sol was then introduced into a petri dish to undergo an evaporation-induced self-assembly (EISA) process for several days. The dried gel was then calcined at 600° C. for 5 h to remove any remaining surfactant. The 1% Ga-MBG obtained was then ground into beads of 250-300 μm particle size using mortar and pestle and stored in a desiccator at room temperature before usage.

(c) Physicochemical Characterization

Field emission scanning electron microscopy (FESEM, Quanta™ 250 FEG-FEI, USA) and High-resolution transmission electron microscopy (HRTEM, JEOL JEM-2100F; accelerating voltage: 200 kV) were used to study the surface morphology and inner microstructure of the samples, respectively. Small angle X-ray diffraction (SAXRD) was performed on 1% Ga-MBG and $ACS^+$ samples with a PANalytical Empyrean X-ray diffractometer equipped with Cu Kα radiation (λ=0.154 nm). Data were collected in the range 0.6°<2θ<7° with a counting time of 5 s per step and a step size of 0.02°. Wide angle X-ray diffraction (WAXRD) was also performed on 1% Ga-MBG, CX and $ACS^+$ in the 2θ range between 5° and 70° with a time step of 5 s and a step size of 0.02°. The textural properties of 1% Ga-MBG and the commercial hemostats were assessed by $N_2$ adsorption/desorption isotherms at 77 K using a Micromeritics ASAP 2020 instrument. To determine specific surface area, pore volume and pore size distribution, the Brunauer-Emmett-Teller (BET)[41] and the Barret-Joyner-Halenda (BJH)[42] methods were employed.

(d) Water Absorption Efficacy and Degradation Behaviour In Vitro

The in vitro water absorption study of 1% Ga-MBG, CX and $ACS^+$ was carried out using PBS according to a known method.[41a] Briefly, each sample was weighed after drying at 50° C. in a vacuum oven overnight ($W_{dry}$) and placed on a filter paper in a funnel. The fluid (PBS) was continuously added dropwise to the samples at a rate of 10 ml/min until the absorption ratio of the samples reached its maximum capacity (when the first drop of fluid fell from the funnel). The wet samples were then weighed as $W_{Wet}$ after removing the filter paper. The fluid absorption ratio was calculated from the following equation:

$$A(\%)=[(W_{wet}-W_{dry})/W_{dry}]\times 100.$$

Each absorption assay was performed in triplicate

The in vitro degradation behaviour of the samples was also assessed by testing their weight loss ratio after immersing in 0.05 M Tris(hydroxymethyl)-aminomethane-HCl solution (Tris-HCl, Sigma-Aldrich, pH 7.4). For this purpose, 20 mg of each pre-dried sample was immersed in a polypropylene vial containing 10 mL Tris-HCl solution following incubation up to 14 days at 37° C. with continuous shaking at 120 rpm (n=3). At the selected time points, the samples were removed from the solution through filtration and carefully washed with distilled water. The samples were subsequently oven-dried to a constant weight at about 50° C. The weight loss ratio at different time points was calculated according to the following equation:

$$\text{Weight loss}(\%)=(W_t-W_0)/(W_0)\times 100\%,$$

where $W_0$ is the initial dry weight and $W_t$ is the weight of samples after immersion in the solution.

(e) In Vitro Coagulation Assay

The activated partial thromboplastin time (APTT) and prothrombin time (PT) were determined according to methods outlined in a previous report in order to explore the effectiveness of the materials on blood plasma coagulation.[41a] Briefly, citrated Human blood samples (9:1 whole blood to 3.2% sodium citrate) were freshly collected from healthy volunteers with approval from the Medical Ethics Committee of University of Malaya, Kuala Lumpur, Malaysia (UMMC reference number 967.10). After centrifugation of the anti-coagulated blood at 3500 rpm for 10 min, the platelet poor plasma (PPP) was obtained. For APTT tests, 100 μL of pre-warmed plasma (37° C.) was incubated for 2 minute with 100 APTT reagent (μL) and selected samples (1% Ga-MBG, CX and $ACS^+$) at various concentrations (5 and 10 mg) followed by measurement of APTT after the addition of 100 μL of pre-warmed $CaCl_2$. For PT tests, different concentrations of the samples were incubated with 100 μL of pre-warmed plasma for 2 minutes, at 37° C. Then 100 μL of the PT reagent was added to the plasma and PT was measured. A negative control (no hemostatic material) was also included.

(f) In Vitro Thrombin Generation, Platelet Adhesion and Thrombus Formation

To study the thrombogenic potential of 1% Ga-MBG, CX and $ACS^+$ in vitro, thrombin generation, platelet adhesion and thrombus assays were systematically investigated. To determine the thrombin-generating activity of the hemostatic materials (1% Ga-MBG, CX and $ACS^+$), a Human thrombin ELISA (Enzyme-Linked Immunosorbent Assay) kit was used to measure thrombin-antithrombin complex (TAT) levels that is an indicator of how much thrombin was formed over a period of time. Fresh human blood anticoagulated with 3.2% sodium citrate was freshly obtained from healthy volunteers. The platelet poor plasma (PPP) was immediately obtained by centrifuging the blood at 3000 rpm for 10 min. The materials were placed in a 24-well culture plates and incubated with PPP at 37° C. for 30 to 60 minutes to induce thrombin generation. After removal of the hemostatic materials at appropriate time intervals, 50 μL of PPP was taken from the each well and then was added to 96-well plates coated with human thrombin-specific antibody for the quantitative measurement of thrombin-antithrombin complex concentrations. A calibration curve was previously obtained in a series of known concentrations of thrombin by measuring the optical density at 450 nm using a microplate reader. The levels of TAT over the materials was estimated using the calibration curve. PPP without hemostatic materials was used as the negative control.

Platelet adhesion response was assayed by lactate dehydrogenase (LDH) as previously describe[41a,43]. Briefly, the hemostatic materials were incubated with platelet rich plasma (PRP) at 37° C. for 30 and 60 min. At the end of each time period, the materials were removed and dip rinsed ten times in PBS to remove the unattached platelets. Thereafter, the materials were placed into PBS containing 1% Triton X-100 for 1 h at 37° C. to lyse the adhered platelets. The number of the adherent platelets on the surfaces of the hemostatic materials was quantified using the LDH/LD kit (Sigma-Aldrich, USA) at 450 nm by an Epoch microplate spectrophotometer (BioTek; Winooski, Vt., USA). The platelets adhered onto the materials was thus calculated with the calibration curve. After platelet adhesion measurements, the morphology of the adhered platelets was examined using a FESEM (Quantat 250 FEG-FEI, USA) at 10-15 kV. In this respect, the materials were fixed in 2.5% glutaraldehyde followed by dehydration in a graded series of ethanol. The materials were then dried in HMDS (hexamethyldisilazane) and coated with gold using a sputter coater for FESEM studies.

The tendency of 1% Ga-MBG, CX and ACS$^+$ to produce a stable blood clot (thrombus) was evaluated by a thrombus generation assay. Thirty milligrams of each hemostatic material was incubated with 1 mL of citrated human blood at 37° C. for two different time points (30 and 60 min) to start the thrombus formation. After each incubation period, the reaction was stopped by adding 10 mL of deionized water followed by soaking the materials in 37% formaldehyde solution for 10 min to fix the formed thrombus. After drying the materials at 50° C. for 8 hours, the degree of thrombogenicity (DT) of the samples at a given time was determined by the equation:

$$\Delta = [(W_t - W_0)/W_0] \times 100\%,$$

where $W_t$ and $W_0$ represent the weight of hemostatic materials before and after in contact with blood, respectively. The thrombus formed on the hemostatic materials' surfaces was photographed by a digital camera. FESEM (Quantat 250 FEG-FEI, USA) images were obtained to observe the interaction of whole blood with the materials. Prior to imaging, the materials were carefully washed with PBS to remove the loosely adherent blood cells. After fixing the adhered blood cells in 2.5% glutaraldehyde for 2 h, the hemostatic materials underwent a graded dehydration series of ethanol and then were dried in HMDS for 10 min. The dried materials were then sputtered with gold and the images were collected with an accelerating voltage of 15 kV.

(g) In Vitro Biocompatibility Assays

The in vitro cytotoxicity of 1% Ga-MBG, CX and ACS$^+$ was assessed by MTT assays using Human dermal fibroblast (HDF) cells. Prior to performing the assays, the tested materials were sterilized under UV light for 12 h. The cells were seeded ($1 \times 10^4$ cells per well) in a 24-well plates and allowed to attach and grow. After 48 h of culture in growth medium (supplemented with normal growth medium containing L-DMEM supplemented with 5% FBS, 1% Penicillin/Streptomycin and 1% Glutamax-1), the cells were subjected to a serum reduction of 1% FBS to arrest cell cycle progression for 24 h; then 5 mg/ml of either 1% Ga-MBG, CX or ACS$^+$ was added directly to the cells. The culture without sample was used as a negative control. Each condition was set up in triplicate. Cell viability was observed at 1 and 3 days using MTT assay (Biotium, Inc., Hayward, Calif.) according to the manufacturer's protocol. The optical density was measured spectrophotometrically at a wavelength of 570 nm using a microplate reader. The results from three individual experiments were averaged, normalized to control.

(h) Confocal Laser Scanning Microscopy

Fluorescence imaging was used to qualitatively verify cell viability. A live/dead solution of 2 µM calcein AM/4 uM EthD-III (Biotium, USA) was prepared by adding 4 mM calcein AM and mM EthD-III to PBS. The tested materials were placed into a small cell-culture dish and covered with the live/dead solution, and the stains allowed to develop in the dark for 30 min. Images were obtained with a fluorescence microscope (CLSM; Leica TCS SP5 II, Leica Microsystems CMS GmbH, Mannheim, Germany) at excitation/emission, 495 nm/515 nm).

(i) Statistical Analysis

Results are given as mean±standard deviations. Statistical difference was analyzed using statistical software (IBM SPSS Statistics for Windows, Version 23). In all the statistical evaluations, a value of $p < 0.05$ was considered to be statistically significant.

II. Results (a) Physicochemical Characterization of the Hemostats

Figure 10:
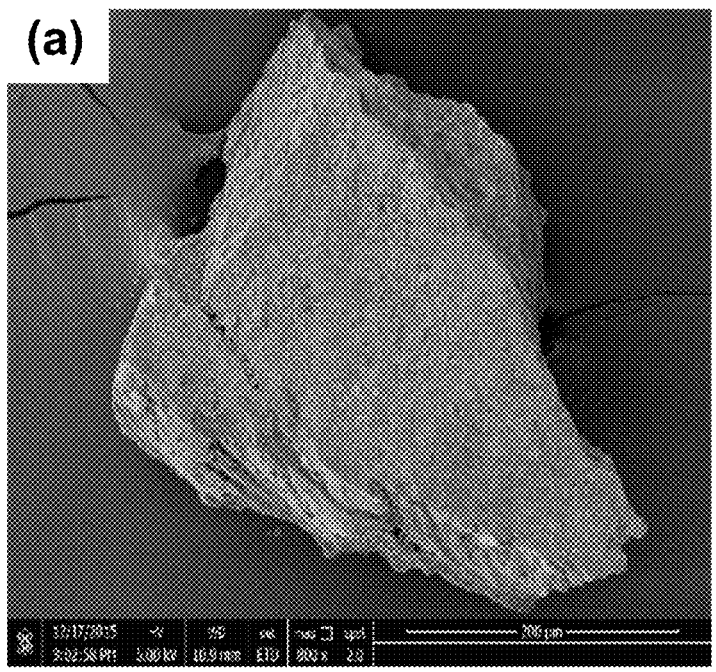
FIG. 10 shows (a) a low magnification FESEM image of 1% Ga-MBG; (b) a high magnification FESEM image of 1% Ga-MBG; (c) a low magnification FESEM image of ACS⁺; (d) a high magnification FESEM image of ACS⁺; (e) a low magnification FESEM image of CX; (f) a high magnification FESEM image of CX; (g) a TEM image of 1% Ga-MBG; (h) a TEM image of ACS⁺; (i) SAXRD of 1% Ga-MBG; (j) SAXRD of ACS⁺; (k) WXRD analysis of 1% Ga-MBG; (l) WXRD analysis of CX; and (m) WXRD analysis of ACS⁺. The high magnification FESEM images (b), (d) and (e) reveal a rough surface texture of all materials. The mesoporosity in the ACS⁺ is marked by a white arrow in (h). Scale bar in (a) and (e) is 200 μm; scale bar in (b) is 50 μm; scale bar in (c) is 1 mm; scale bar in (d) is 20 μm; scale bar in (f) is 30 μm; scale bar in (g) is 50 nm; scale bar in (h) is 20 nm.
Figure 10:
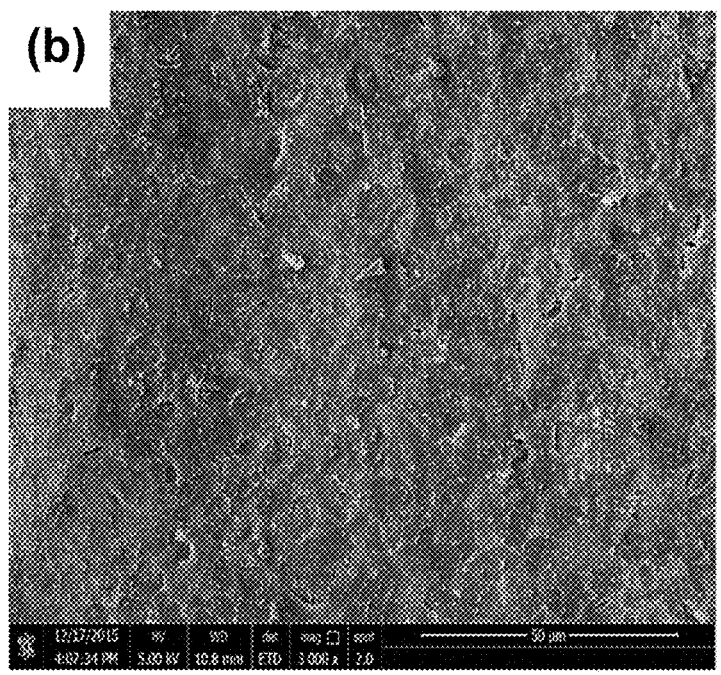
Figure 10:
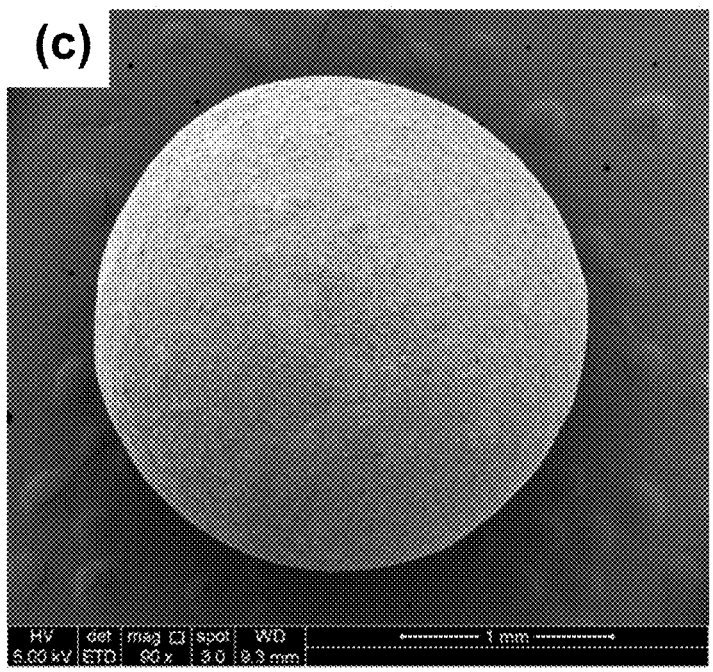
Figure 10:
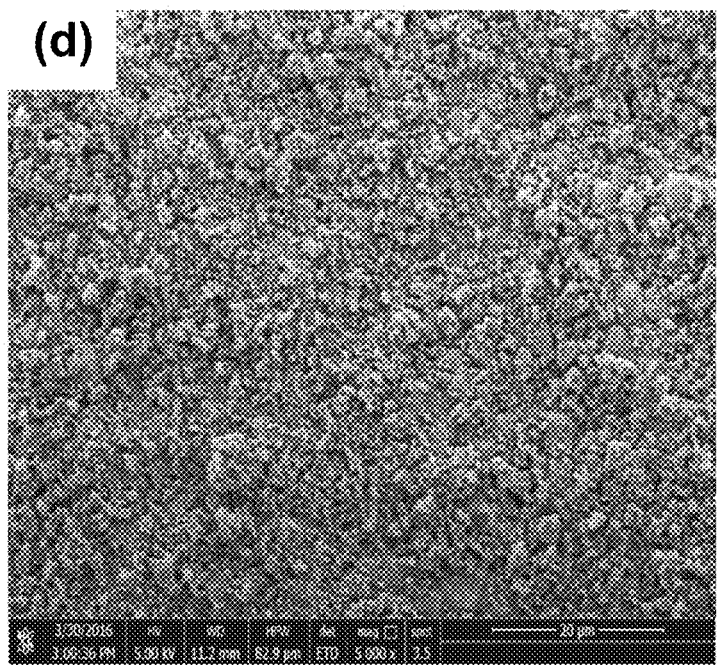
Figure 10:
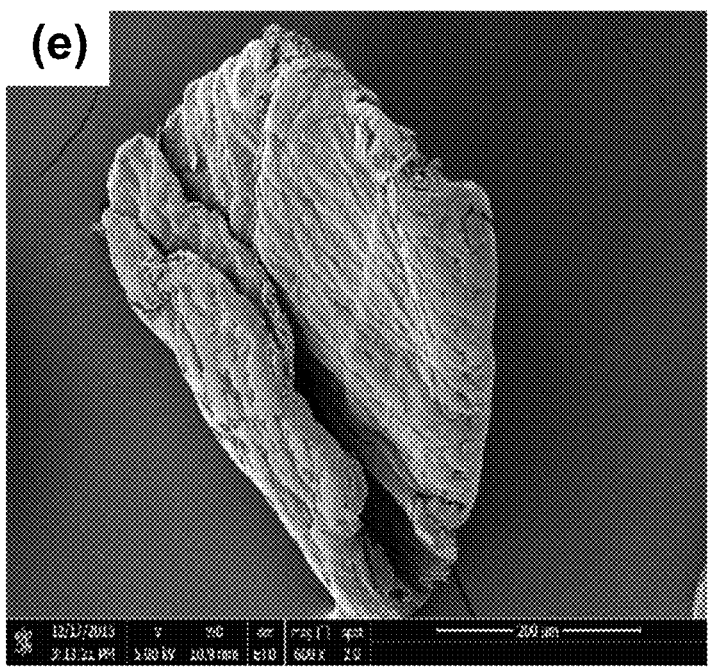
Figure 10:
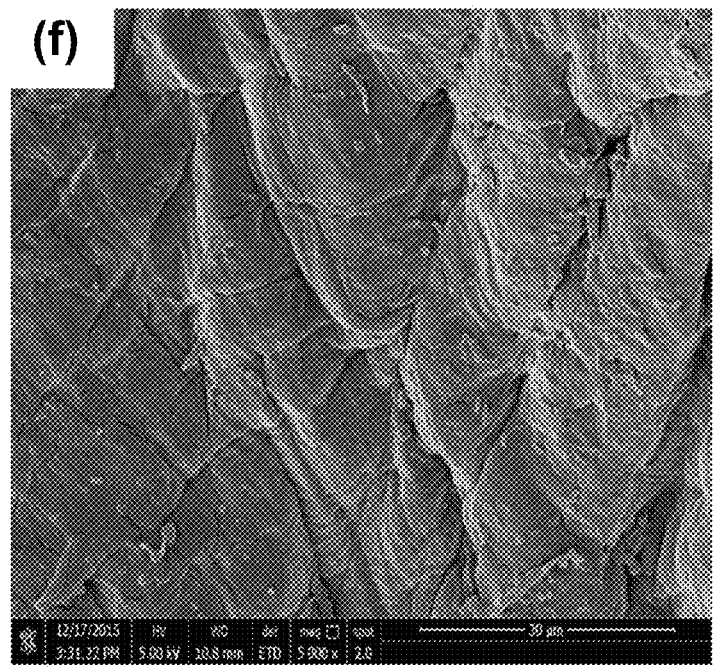
Figure 10:
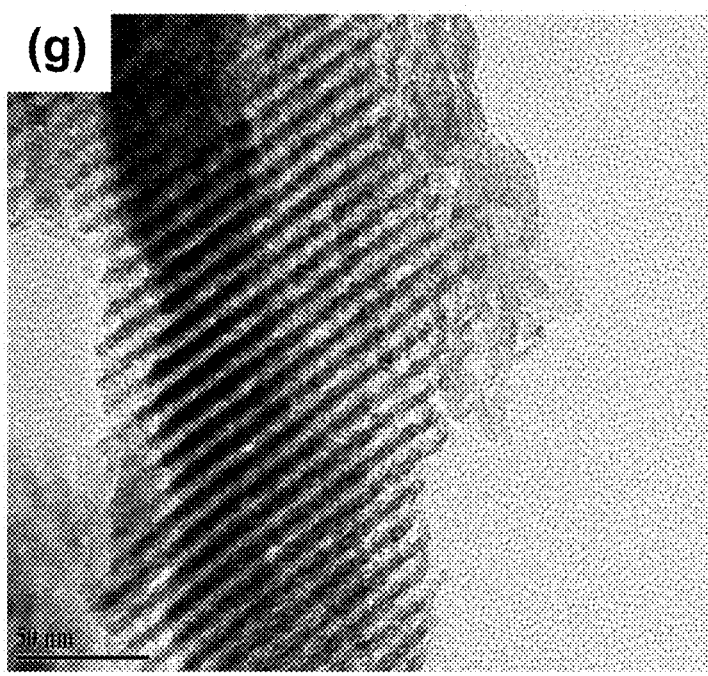
Figure 10:
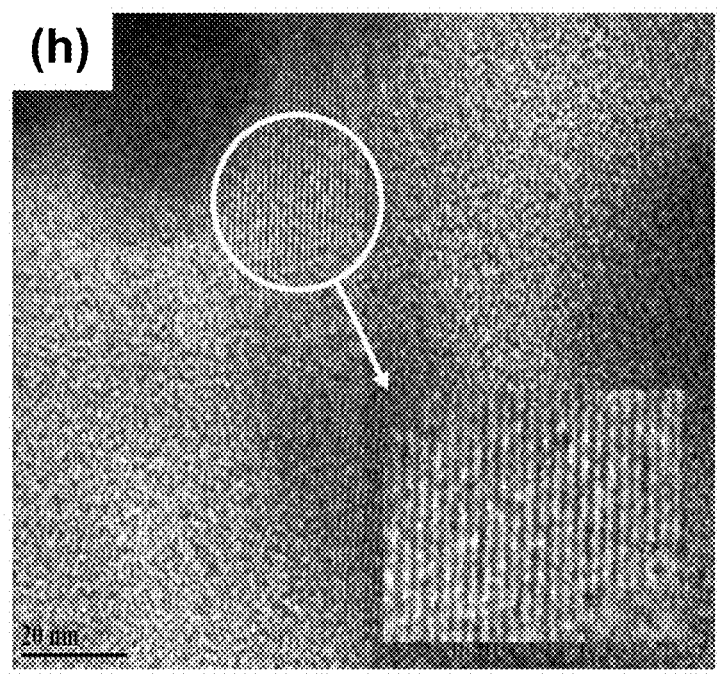
Figure 10:
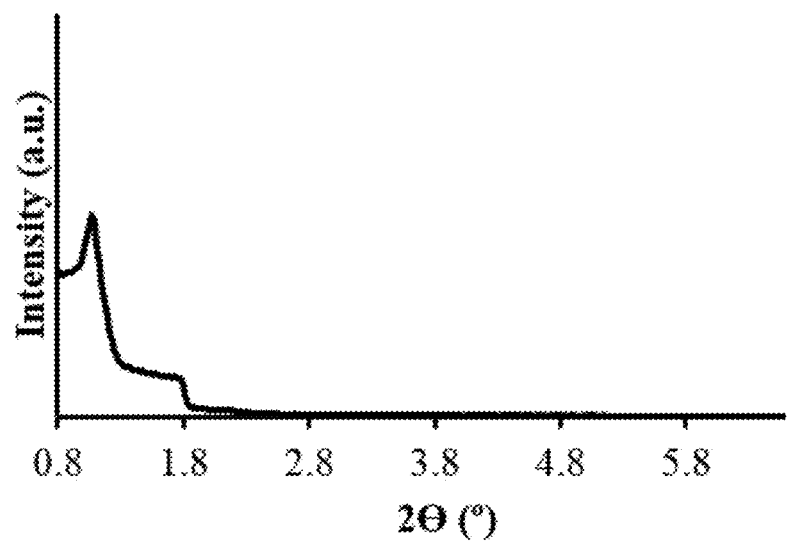
Figure 10:
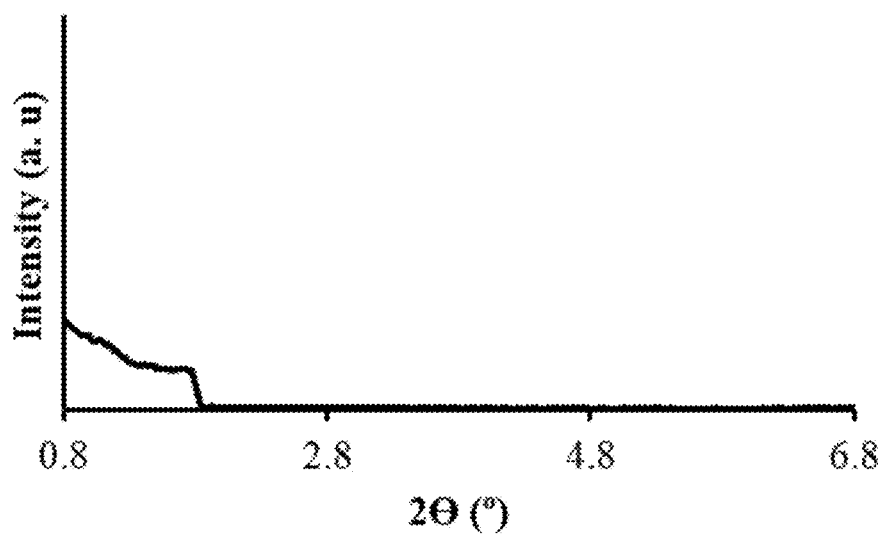
Figure 10:
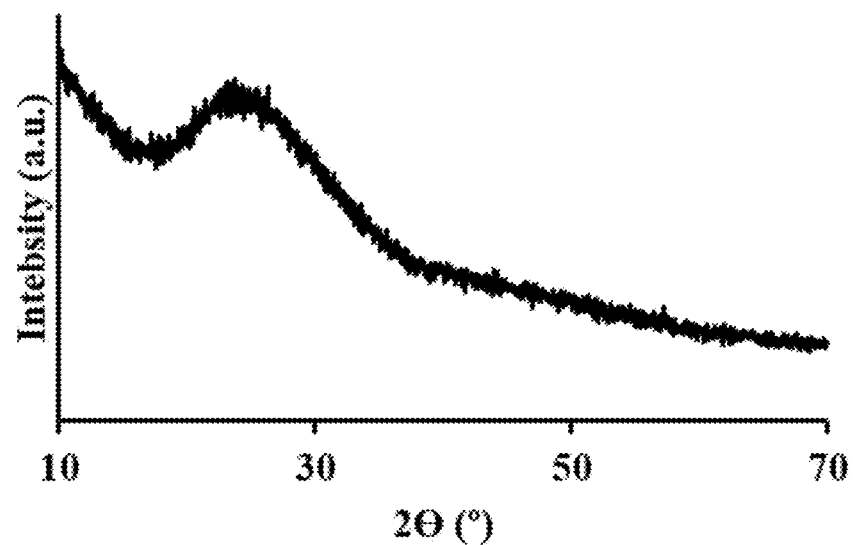
Figure 10:
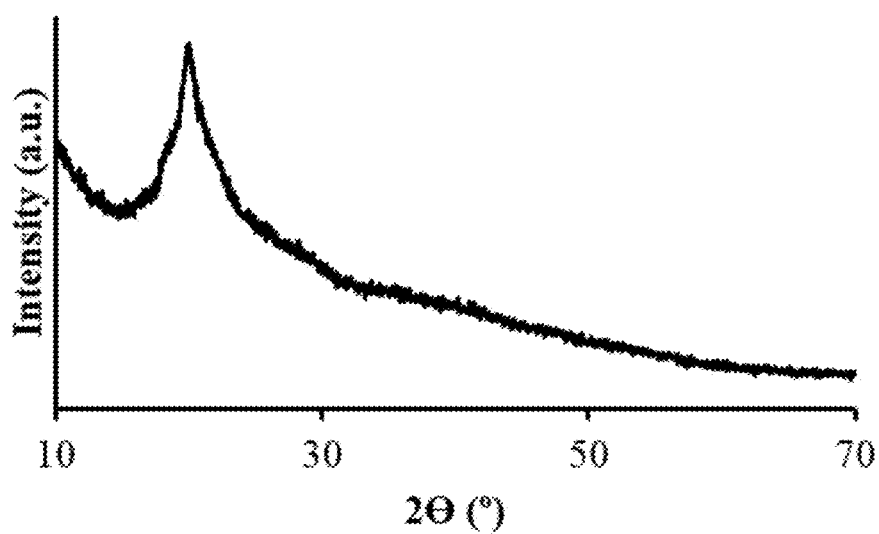
Figure 10:
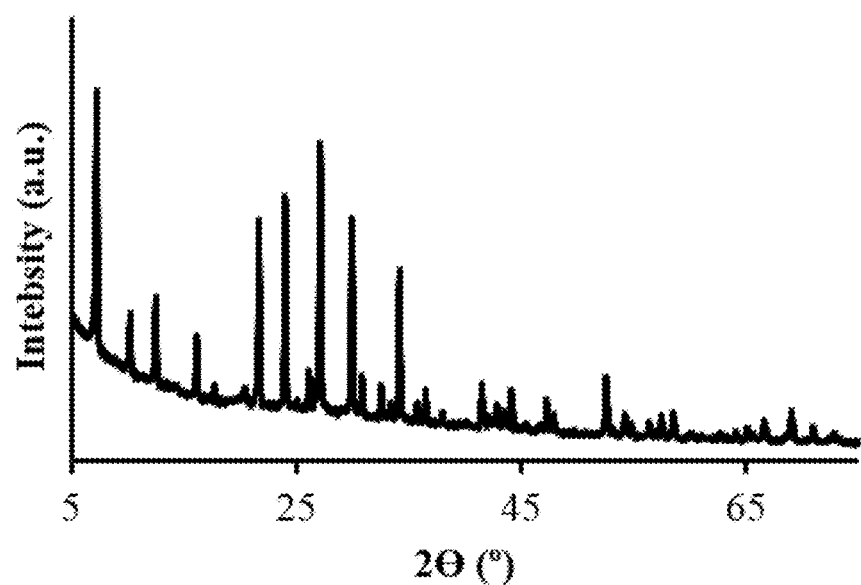

The surface morphologies and microstructures of 1% Ga-MBG and both commercial hemostats (CX and ACS$^+$), examined using FESEM, are depicted in FIG. 10. 1% Ga-MBG sample was made up of irregularly shaped particles, (FIGS. 10(a) and (b)) exhibiting less roughness than the ACS$^+$ (FIG. 10(c), and (d)) which exhibited a spherical particle shape. The FESEM micrographs of CX (FIGS. 10(e) and (f)) also show a rough and folded surface morphology. To identify the internal morphology of 1% Ga-MBG and ACS$^+$, HRTEM was used. The HRTEM image of 1% Ga-MBG (FIG. 10(g)) revealed a highly ordered two-dimensional (2D) hexagonal mesostructure with uniform cylindrical pore channels, whereas the image of ACS$^+$ (FIG. 10(h)), which is a primarily microporous material, barely evidences a secondary mesoporous structure.

The ordered mesoporous structure of the 1% Ga-MBG was also demonstrated by the SAXRD data. The SAXRD patterns of the 1% Ga-MBG (FIG. 10(i)) displayed two diffraction peaks in the small-angle regime, at around $2\theta = 1.09°$ and $1.7°$ demonstrating the presence of a high degree of mesoscopic organization and local hexagonal symmetry which agreed with the results obtained by TEM. However, the SAXRD of ACS$^+$ (FIG. 10(j)) exhibited two poorly resolved peaks in $2\theta$ range $1-1.5°$. WXRD patterns were also collected to determine the amorphous or crystalline states of 1% Ga-MBG, CX and ACS$^+$. In contrast to WAXRD patterns of 1% Ga-MBG (FIG. 10(k)) and CX (FIG. 10(l)), which show only one broad diffraction peak at $2\theta = 15-35°$ revealing their amorphous states, the WAXRD pattern of ACS$^+$ (FIG. 10(m)) shows several crystal diffraction peaks associated with the zeolite Linde type 5A (LTA-5A) which is in agreement with a highly crystalline state of ACS$^{+44}$.

The $N_2$ adsorption-desorption isotherm at 77 K of 1% Ga-MBG (not shown), which was found to be type IV with a H1 hysteresis loop, further was in agreement with the presence of a mesoporous structure with hexagonally packed cylindrical channels. The pore size distribution of the sample also indicates a monomodal distribution centered in the mesoporous range (5.3 nm). As compared to 1% Ga-MBG, the isotherm of ACS⁺ exhibits an intermediate behaviour between type I and IV isotherm, while not wishing to be limited by theory, suggesting the presence of both microporosity and mesoporosity[45]. The obtained pore size distribution also displays the bimodal micro- and mesoporous nature of ACS⁺. However, CX showed the lowest surface area and pore volume. Table 4 presents the main textural parameters including specific surface area, pore diameter and pore volume of the various samples measured by the $N_2$ adsorption porosimetry at 77 K. The textural studies revealed that 1% Ga-MBG possesses better textural properties compared to those of CX and ACS⁺. Although ACS⁺ has comparable surface area to that of 1% Ga-MBG, its pore volume is significantly smaller due to the prevalence of micropores on mesopores.

TABLE 4

Textural properties of 1% GaMBG, CX and ACS⁺.

| Samples | $S_{BET}$ (m² g⁻¹) | Pore size (nm) | Pore volume (cm³ g⁻¹) |
|---|---|---|---|
| 1% Ga-MBG | 597 | 5.3 | 0.77 |
| CX | 1.00 | 6.2 | 0.003 |
| ACS⁺ | 561 | 8.5 | 0.124 |

(b) Water Absorbability and Degradation In Vitro

FIG. 11(a) shows the absorption ratio of the samples in PBS. CX had greater absorption than those of 1% Ga-MBG and ACS⁺. As compared with ACS⁺, 1% Ga-MBG also exhibited a higher absorption ratio which, while not wishing to be limited by theory, may be due to its higher surface area and pore volume. The in vitro degradation behaviours of the tested materials were also investigated in Tris-HCl solution at 37° C. As can be seen in FIG. 11(b), the degradation rate of all samples increased with prolonged immersion time particularly during the first three days. However, a notable difference between the groups was observed in their degradation at either of the four time points. 1% Ga-MBG demonstrated a higher weight loss than that of CX and ACS⁺ over 14 days which, while not wishing to be limited by theory, can be attributed to its larger specific surface area and higher pore volume, making the 1% Ga-MBG dissolve faster over time. ACS⁺ showed the lowest weight loss of 10%, which is in agreement with its poor degradability.

(c) APTT and PT Assay

Figure 12:
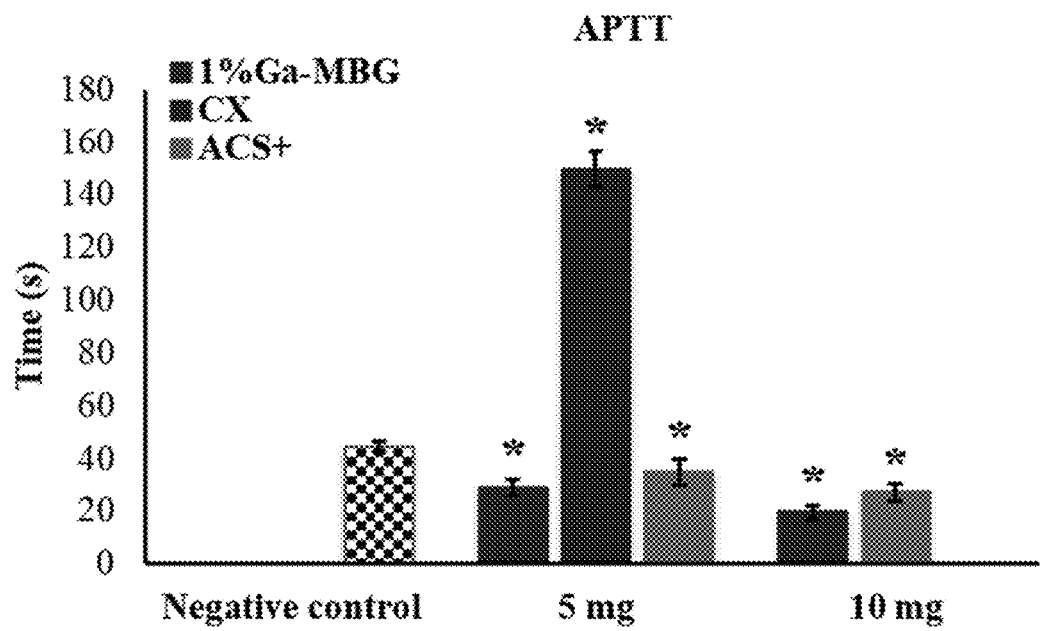
FIG. 12 shows plots of (a) APTT and (b) PT measurements of 1% Ga-MBG, CX and ACS⁺ in comparison to a negative control.
Figure 12:
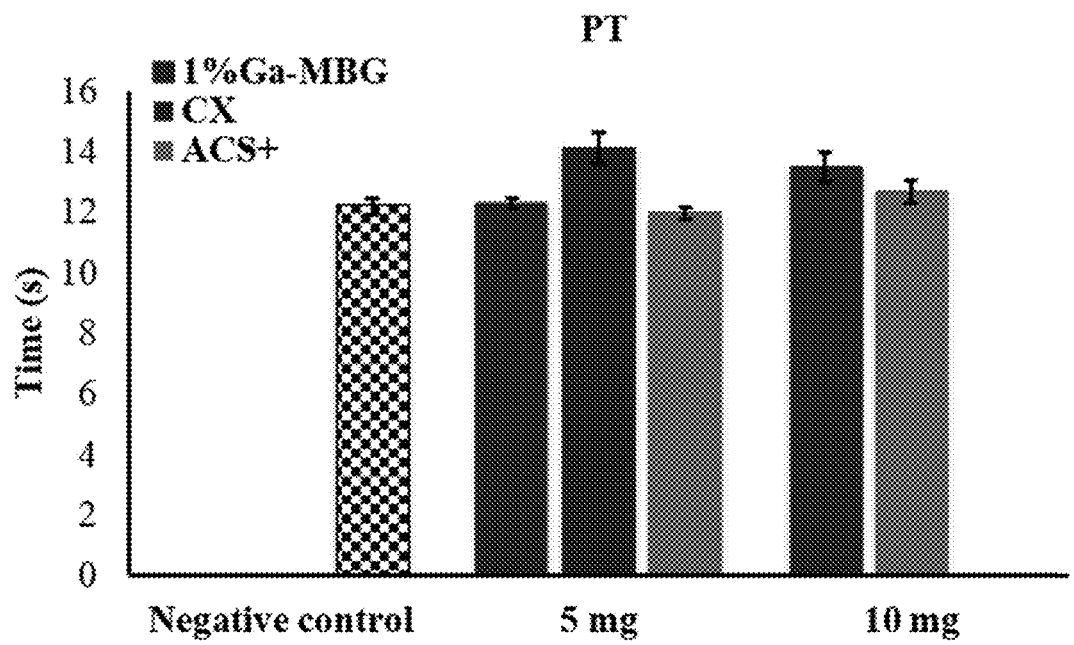

To assess the in vitro pro-coagulant activity of hemostatic materials (1% Ga-MBG, CX and ACS⁺), two commonly used parameters, i.e., APTT and PT of the investigated materials were measured using two different amounts (5 and 10 mg). APTT and PT tests are used to investigate the intrinsic and extrinsic pathway, respectively. Both methods are used to investigate the common coagulation pathways. FIG. 12 presents the APTT and PT results of the investigated materials. It was found that the administration of the hemostatic materials to the blood serum remarkably affected the values of APTT in a dosage-dependent way. As can be seen in FIG. 12(a), at the lowest dosage examined (5 mg), a shortened APTT was observed for the blood plasma treated with 1% Ga-MBG and ACS⁺ in comparison to the negative control, whereas, conversely, APTT was found to be substantially prolonged in the presence of CX. Unlike CX that led to formation of a mechanically unstable gel layer at higher amount (10 mg) interfering with the clotting mechanism, the time to initiate the intrinsic pathway (APTT) was significantly decreased with 1% Ga-MBG (19.55 s) in comparison to the ACS⁺ (26.81) and negative control (44.26 s). Stable and strong hemostatic clots were formed by trapping 1% Ga-MBG and ACS⁺ particles in a fibrin meshwork, whereas CX caused the clot to rupture. On the other hand, PT of the investigated materials remained unchanged at the given amounts (5 and 10 mg), suggesting, while not wishing to be limited by theory, that the hemostatic materials had no observed effect on PT (FIG. 12(b)). However, in the case of the higher CX amount (10 mg), PT was markedly prolonged similar to that of APTT.

(d) Thrombin Generation Assay

Figure 13:
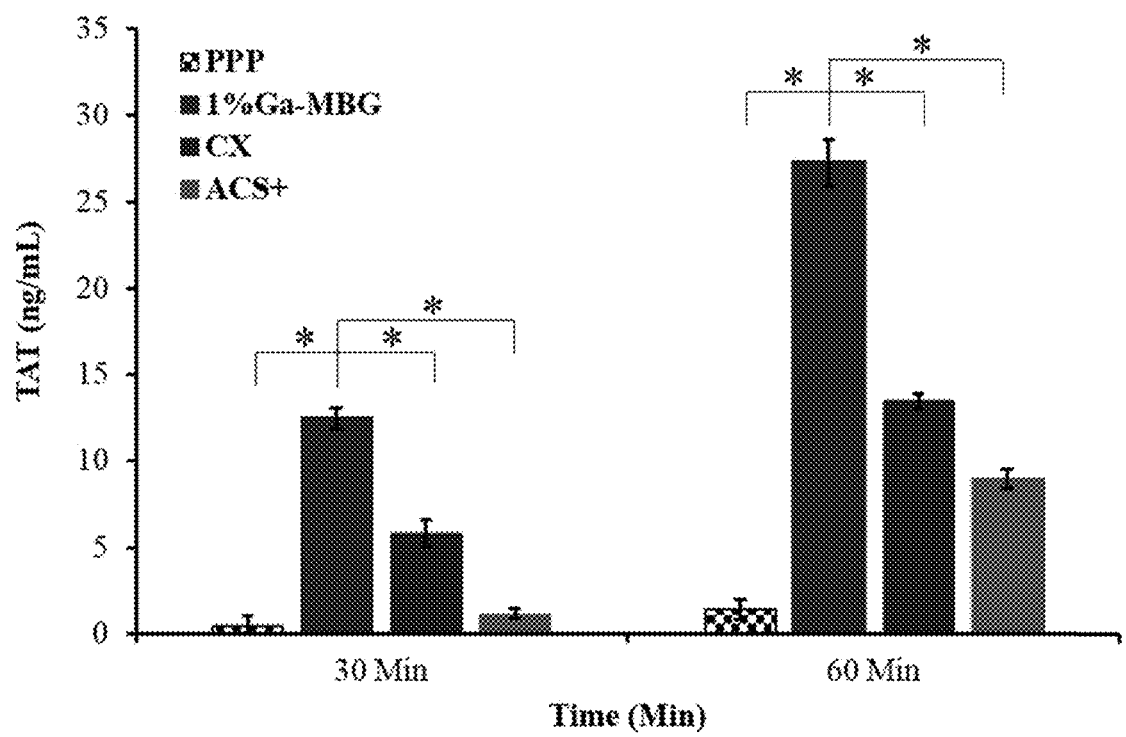
FIG. 13 shows the effect of different hemostatic materials (1% Ga-MBG, CX and ACS⁺) on thrombin generation over time, as measured by the levels of TAT complex in comparison to a negative control (PPP).

To evaluate the thrombin-generating activity of the tested materials, the TAT of the materials was measured in PPP. The results (FIG. 13) revealed that the TAT levels were elevated over time in PPP contacted with all the samples with respect to the negative control. However, it was found to be higher in 1% Ga-MBG as compared with CX and ACS⁺ over 60 min (FIG. 13).

(e) Platelet Adhesion and Activation

Figure 14:
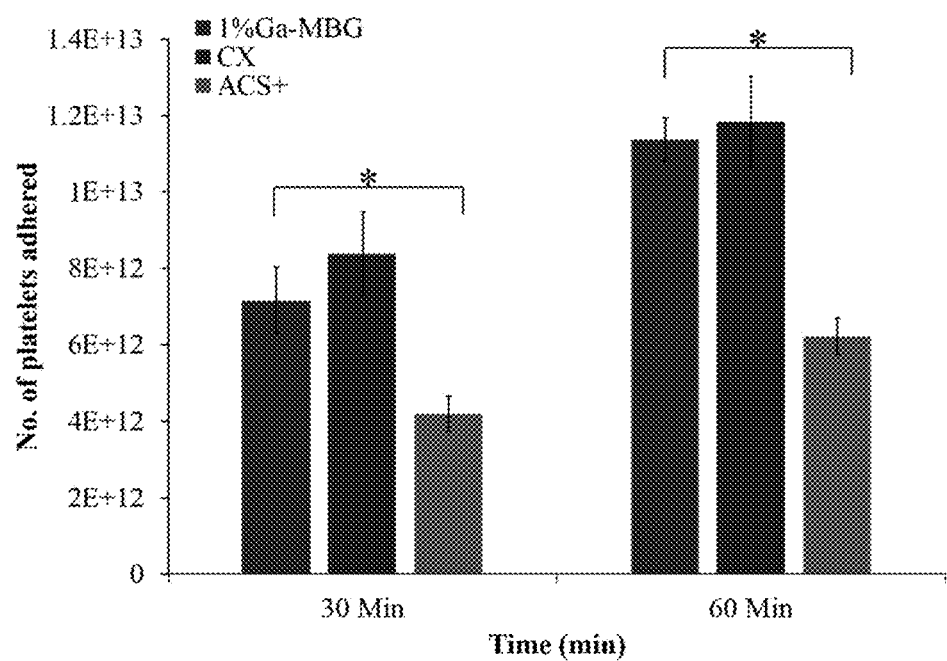
FIG. 14 shows (a) quantification of platelet adhesion on the hemostatic materials (1% Ga-MBG, CX and ACS⁺) after different incubation times (30 minutes and 60 minutes) in platelet rich plasma (PRP). * Represents a significant difference, $p<0.05$; and FESEM micrographs of platelets adhered to the surface of (b) 1% Ga-MBG (scale bar 40 μm); (c) 1% Ga-MBG (scale bar 10 μm); (d) CX (scale bar 40 μm); (e) CX (scale bar 10 μm); (f) ACS⁺ (scale bar 40 μm); and (g) ACS⁺ (scale bar 10 μm) after 30 min of incubation in PRP.
Figure 14:
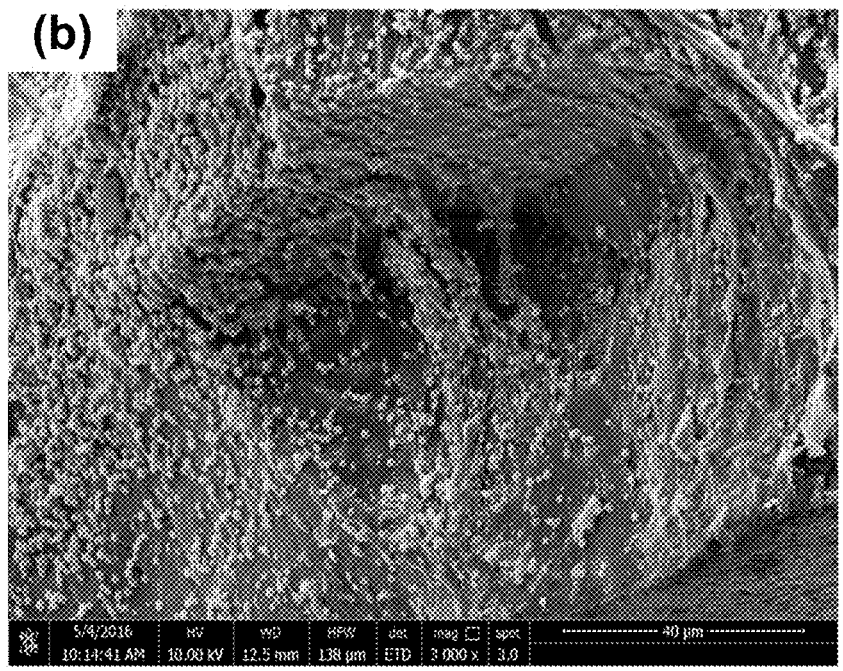
Figure 14:
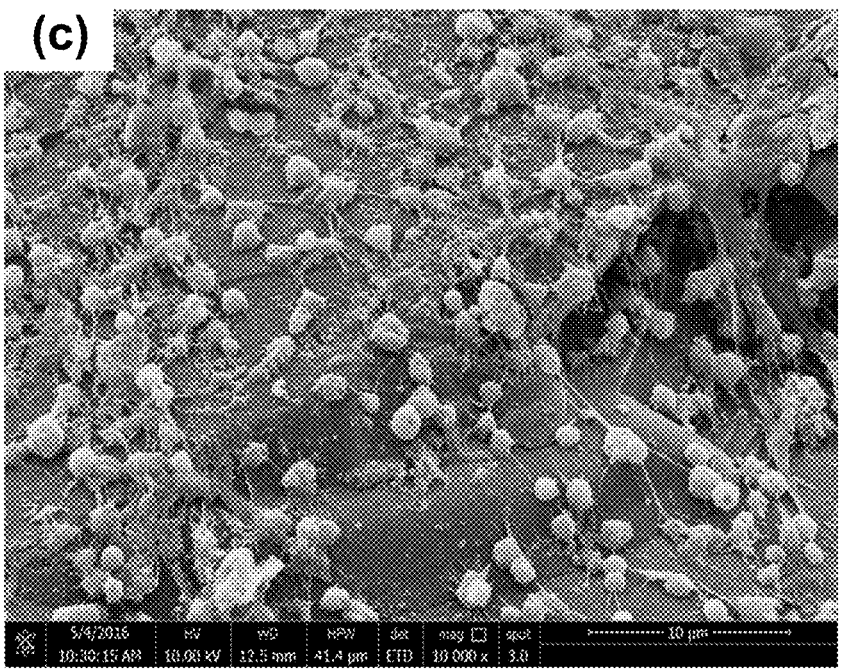
Figure 14:
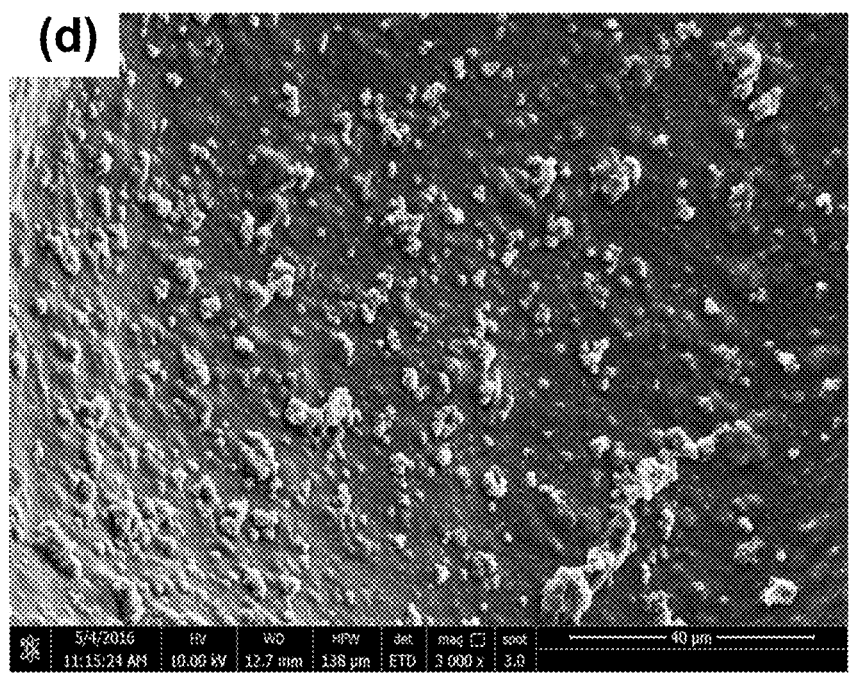
Figure 14:
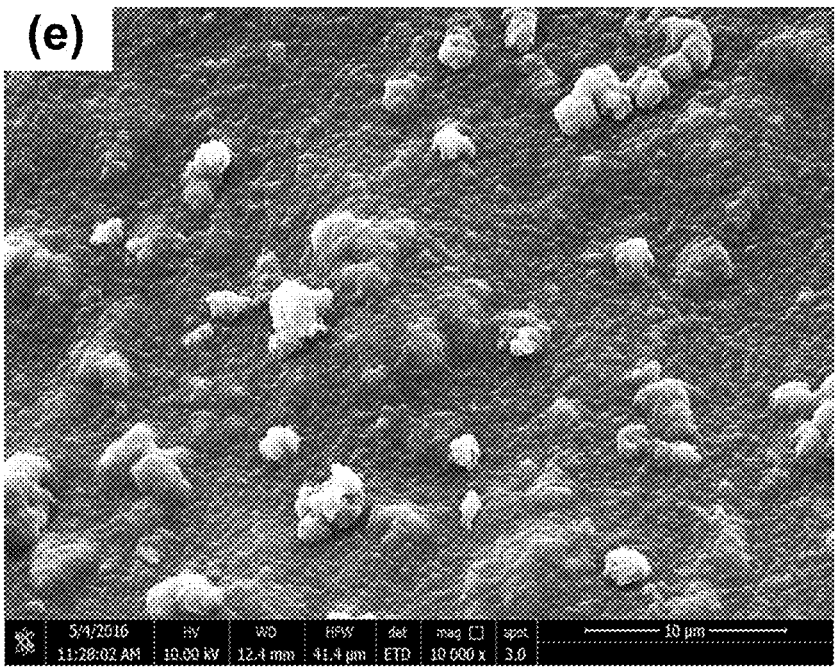
Figure 14:
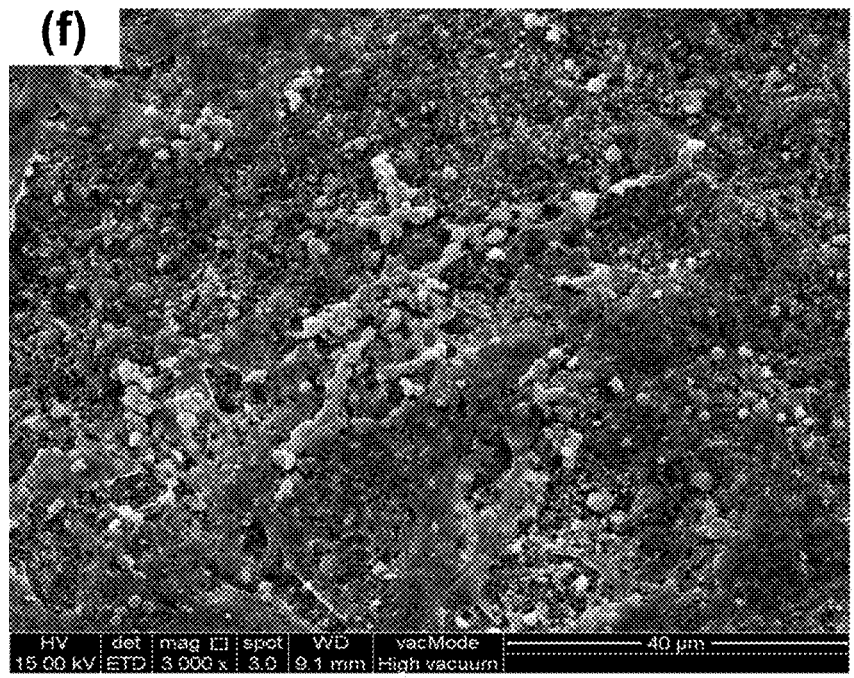
Figure 14:
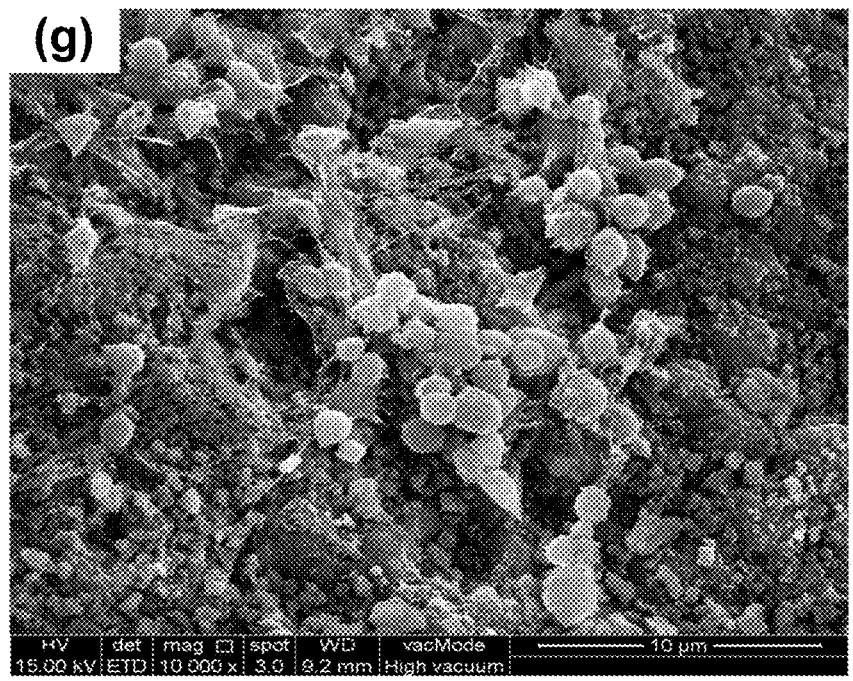

The in vitro capability of 1% Ga-MBG to aggregate and activate platelets was compared to CX and ACS⁺. In this regard, the number of platelets adhered on the surface of the hemostats was quantified by the activity of LDH and the morphology of the adherent platelets was visualized using FESEM (FIG. 14). The quantitative result (FIG. 14(a)) demonstrated that the number of adherent platelets to the surface of these three hemostatic materials increased in number with incubation time up to 60 min. However, while the number of adherent platelets to the surface of 1% Ga-MBG and CX increased significantly after 60 min incubation with PRP, a negligible increase occurred in the number of platelets adhered on the surface of ACS⁺. These results were further confirmed by FESEM micrographs, as shown in FIG. 14(b-g). Much more platelet aggregates and spread platelets were observed on the surface of 1% Ga-MBG (FIG. 14(b), (c)) and CX (FIG. 14(d), (e)) in comparison with ACS⁺ (FIG. 14(f), (g)), for which only few aggregates were observed. However, although no significant difference was found in the number of adhering platelets among the 1% Ga-MBG and CX groups, the platelets adhered to the 1% Ga-MBG were remarkably more activated than those on the CX, as platelets extended long pseudopodia.

(f) In Vitro Blood Clot Formation

Figure 15:
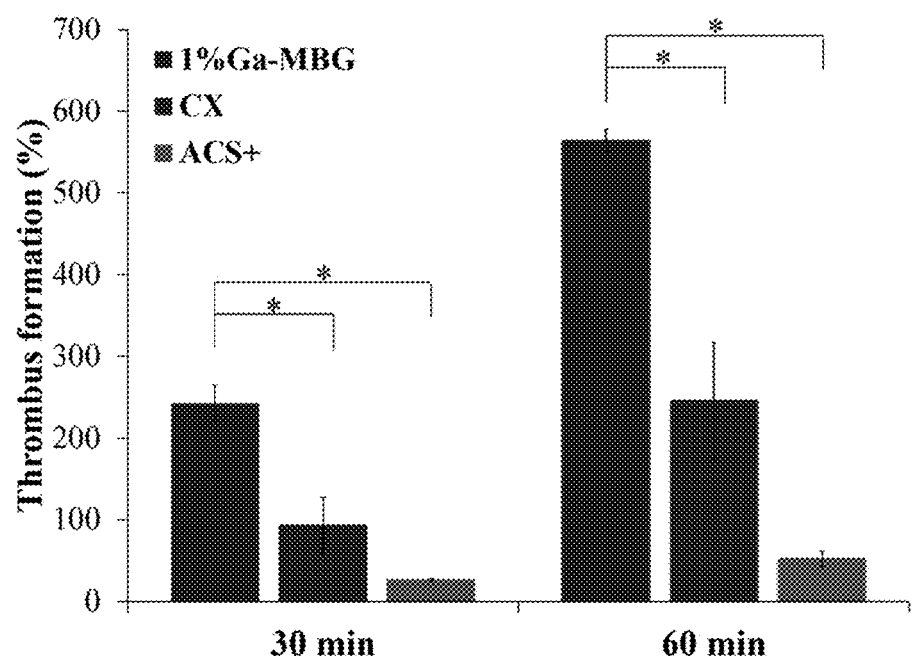
FIG. 15 shows (a) quantitative analysis of thrombus formation on the hemostatic materials (1% Ga-MBG, CX and ACS⁺) surface upon incubation over 30 and 60 minutes; digital photographs of the thrombus formed on (b) CX before fixation by glutaraldehyde; (c) CX after fixation by glutaraldehyde; (d) ACS⁺ before fixation by glutaraldehyde; (e) ACS⁺ after fixation by glutaraldehyde; (f) 1% Ga-MBG before fixation by glutaraldehyde; and (g) 1% Ga-MBG after fixation by glutaraldehyde; and FESEM observations at low and high magnification, respectively, of agglutinated RBCs on the surface of (h, i) 1% Ga-MBG, (j, k) CX and (l, m) ACS⁺. More RBCs clumped in fibrin threads to form a thrombus on 1% Ga-MBG surface compared with CX and ACS⁺. Scale bar in (h), (j) and (l) is 50 μm; scale bar in (i), (k) and (m) is 20 μm.
Figure 15:
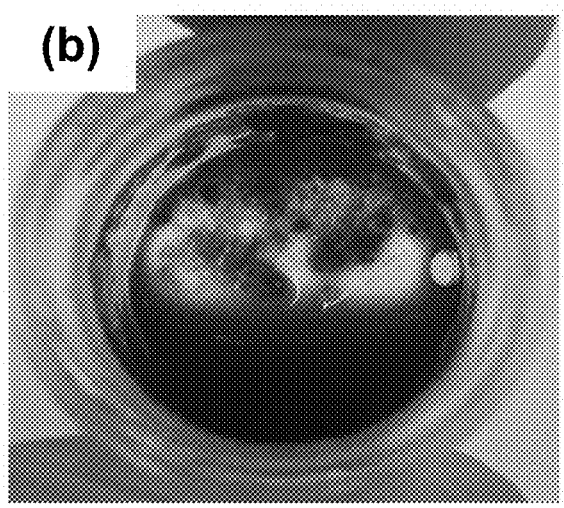
Figure 15:
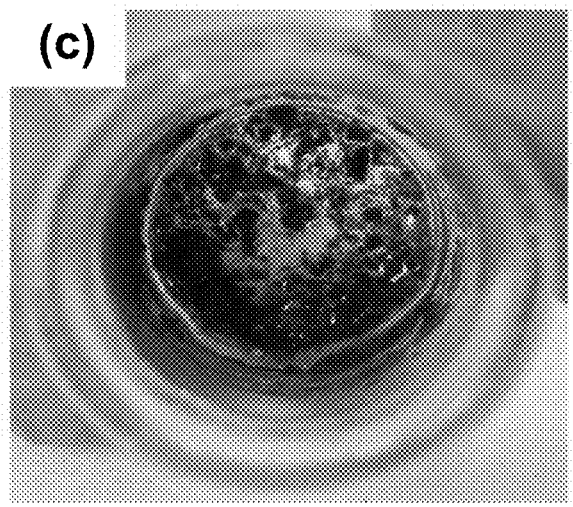
Figure 15:
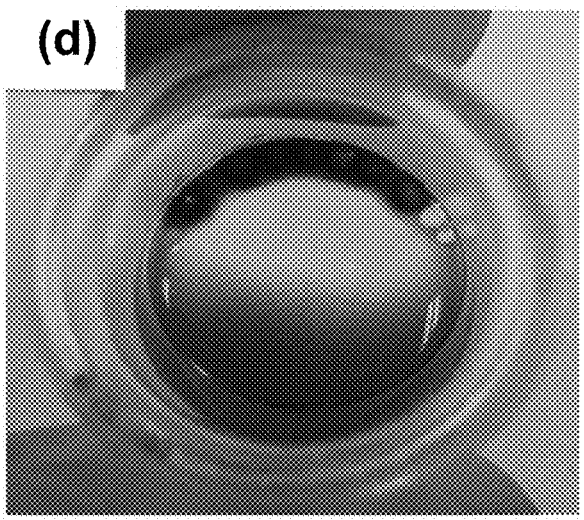
Figure 15:
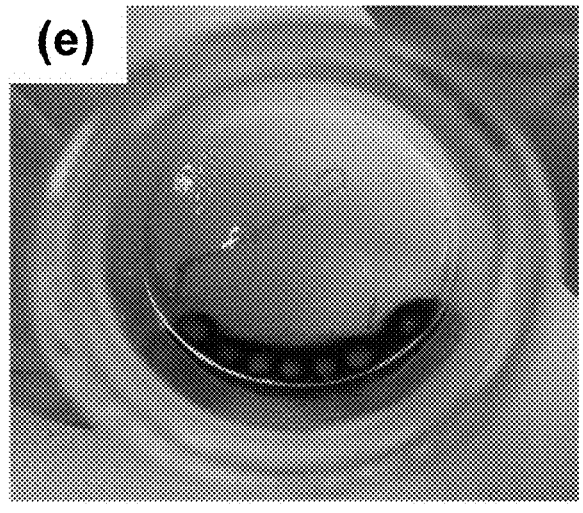
Figure 15:
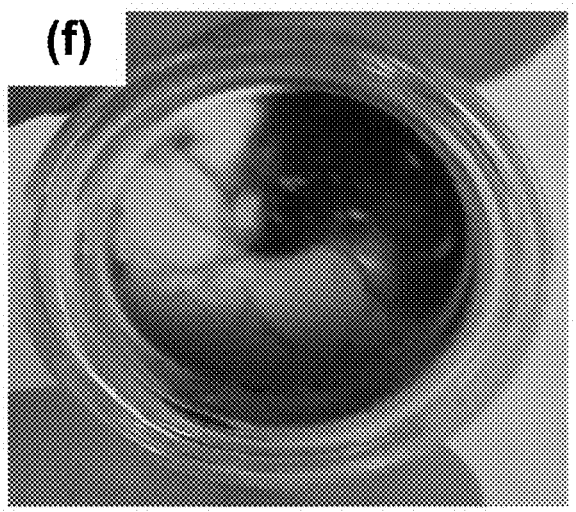
Figure 15:
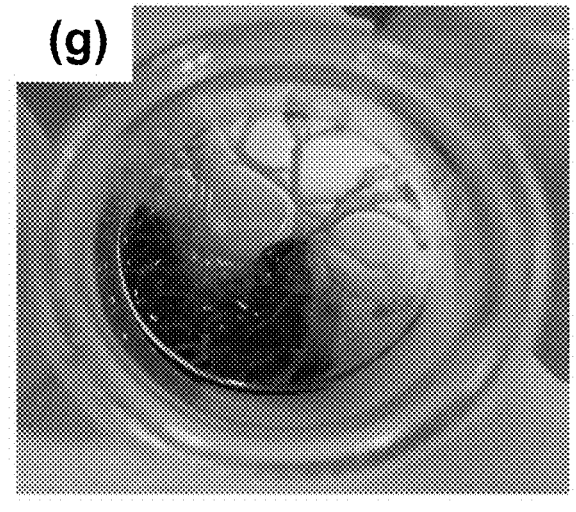
Figure 15:
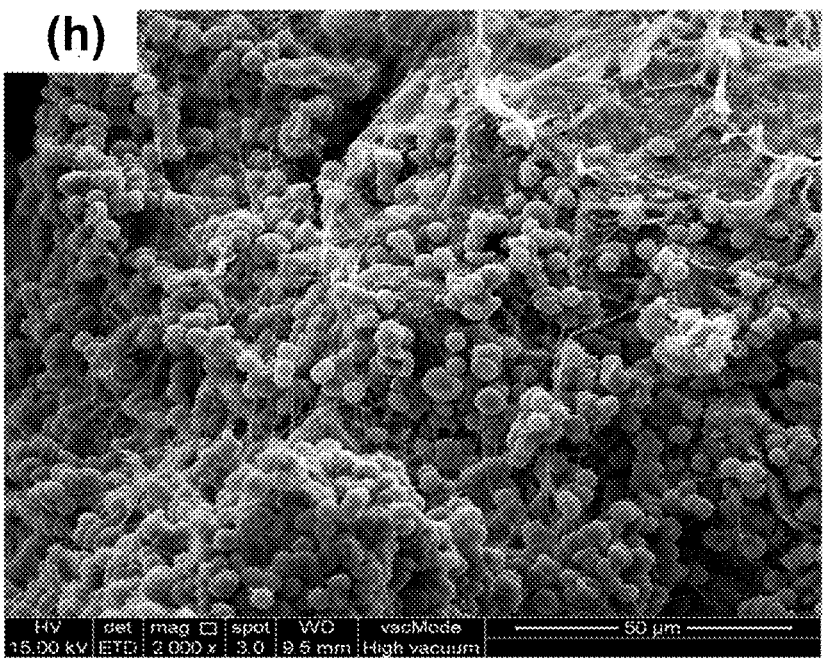
Figure 15:
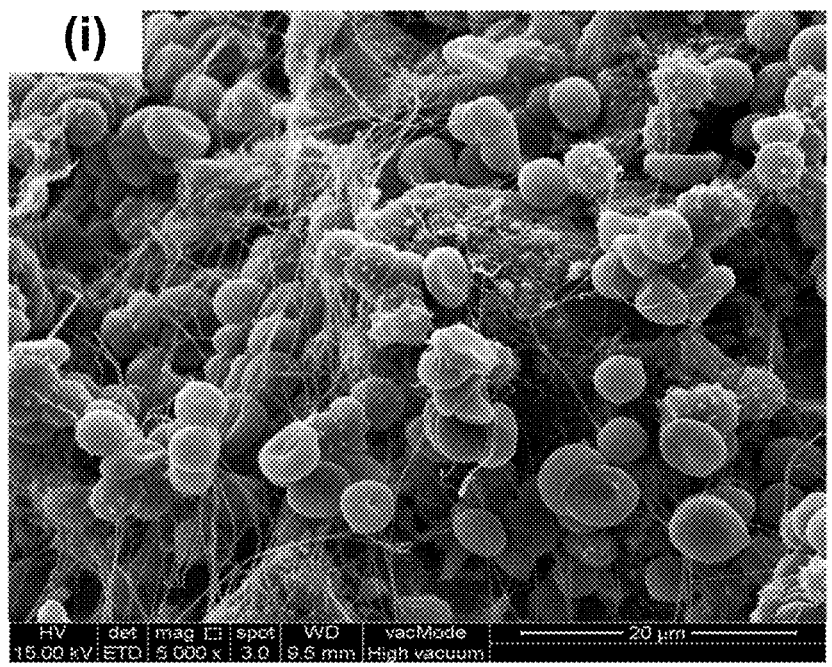
Figure 15:
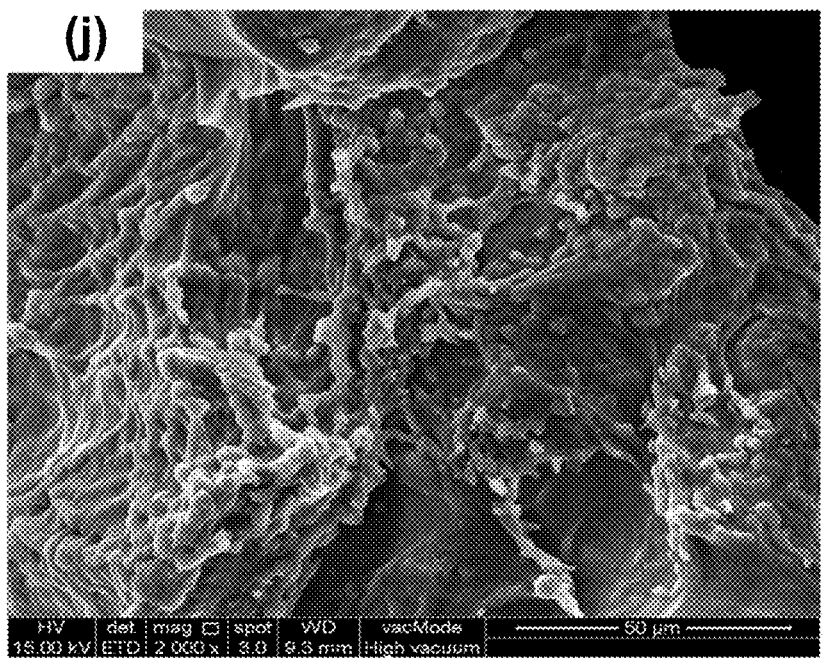
Figure 15:
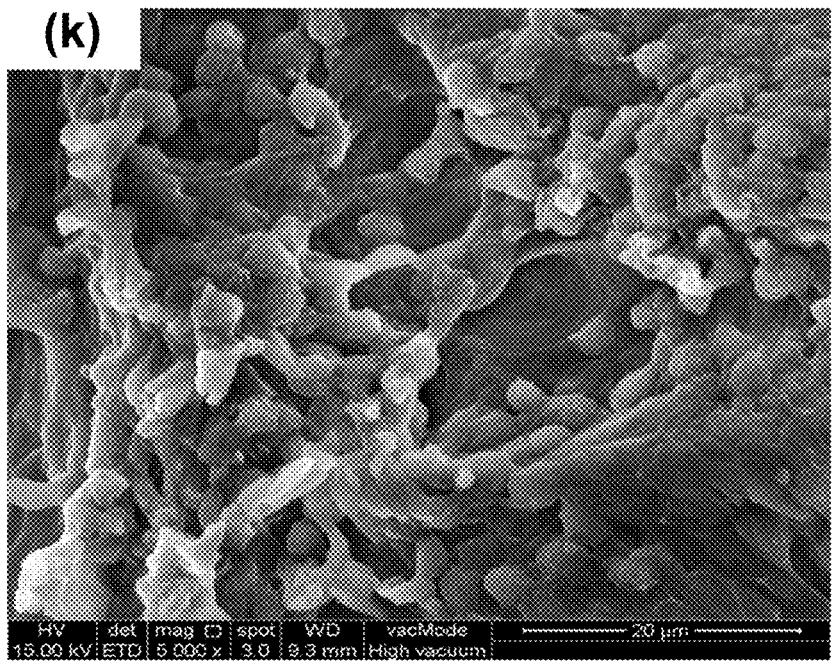
Figure 15:
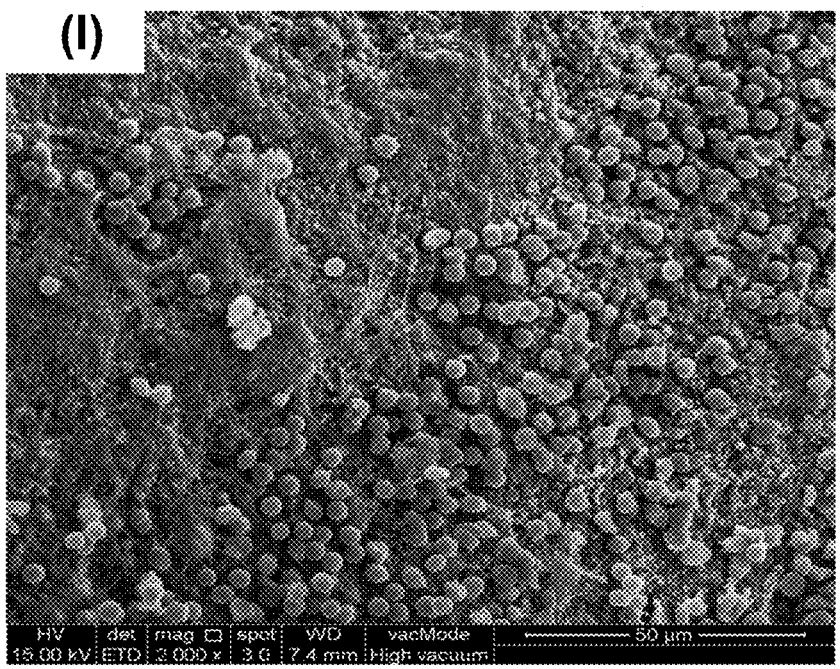
Figure 15:
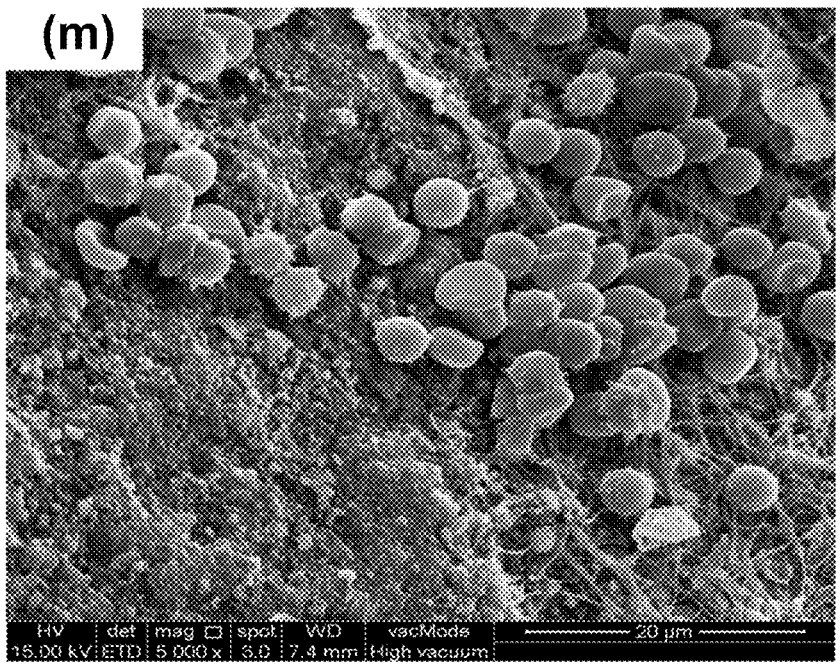

The induced thrombotic effects of 1% Ga-MBG were compared with those of CX and ACS⁺ and the results are depicted in FIG. 15(a). As compared to the lower thrombus formation ability of CX and ACS⁺, 1% Ga-MBG resulted in the highest thrombus formation over the 60 min incubation period, demonstrating its thrombogenic nature. These results exhibited the same trend as the blood coagulation experiments (PT and APTT), where 1% Ga-MBG was found to be superior to other samples. The results of the thrombus formation test were further confirmed by digital photographs and FESEM (FIG. 15(b-g)). As can be seen from the digital images, unlike CX (FIG. 15(b), (c)) and ACS⁺ (FIG. 15(d), (e)), which resulted in the formation of small and unstable hemostatic clots, more red blood cells (RBCs) were coalesced into an erythrocyte clot on the 1% Ga-MBG (FIG. 15(f), (g)) surface forming a physically more stable clot surrounded by a dense meshwork of fibres. The clots formed on the surface of the 1% Ga-MBG were darker in colour and adhered better to the material surface with respect to CX and ACS⁺. FESEM images also showed the physical interaction of blood components with 1% Ga-MBG, CX and ACS⁺ to form a clot (FIG. 15 (h; 1% Ga-MBG low magnification), (i; 1% Ga-MBG high magnification), (j; CX low magnification), (k; CX high magnification), (l; ACS$^+$ low magnification) and (m; ACS$^+$ high magnification). Although adhesion of RBCs was observed on all investigated materials, more RBCs seemed to clump in a fibrin protein mesh, forming a larger agglomerate on the 1% Ga-MBG surface compared with CX and ACS$^+$, where fewer erythrocyte plugs were noted on their surface. Nevertheless, it should be noted that RBCs formed more aggregates on the CX surface compared to ACS$^+$, while more fibrin was observed on ACS$^+$. These results were in line with the previous observation in clot formation tests.

(g) Fibroblast Responses to Hemostatic Materials

Figure 16:
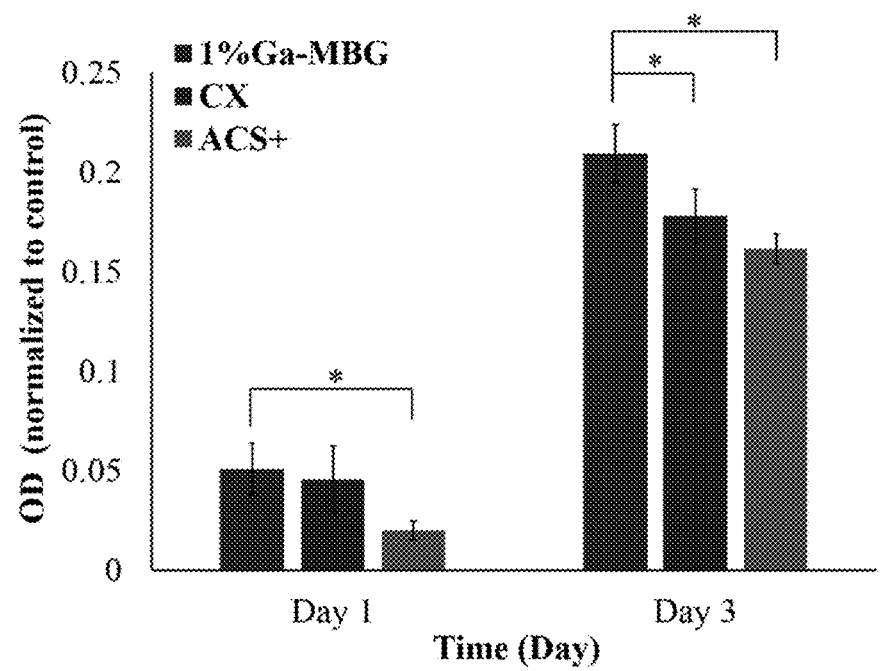
FIG. 16 shows (a) quantitative analysis by MTT assay of human dermal fibroblast (HDF) cells viability after 1 and 3 days exposure to 1% Ga-MBG, CX and ACS⁺; and fluorescent microscopy images of HDF cells cultured in the presence of (b) 1% Ga-MBG, (c) CX and (d) ACS⁺ for 3 days. Live and dead cells appeared as green and red fluorescence respectively in color images. White arrows show the particles surrounded by HDFs cells. Inset picture in (b), (c) and (d) shows phase contrast micrographs of 1% Ga-MBG, CX and ACS⁺, respectively. Scale bar in (b), (c) and (d) is 200 µm.
Figure 16:
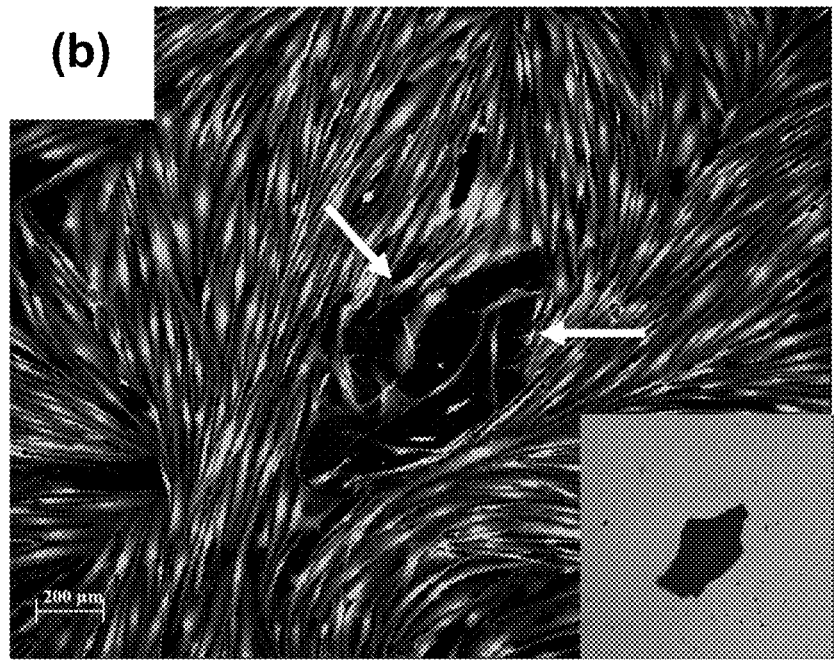
Figure 16:
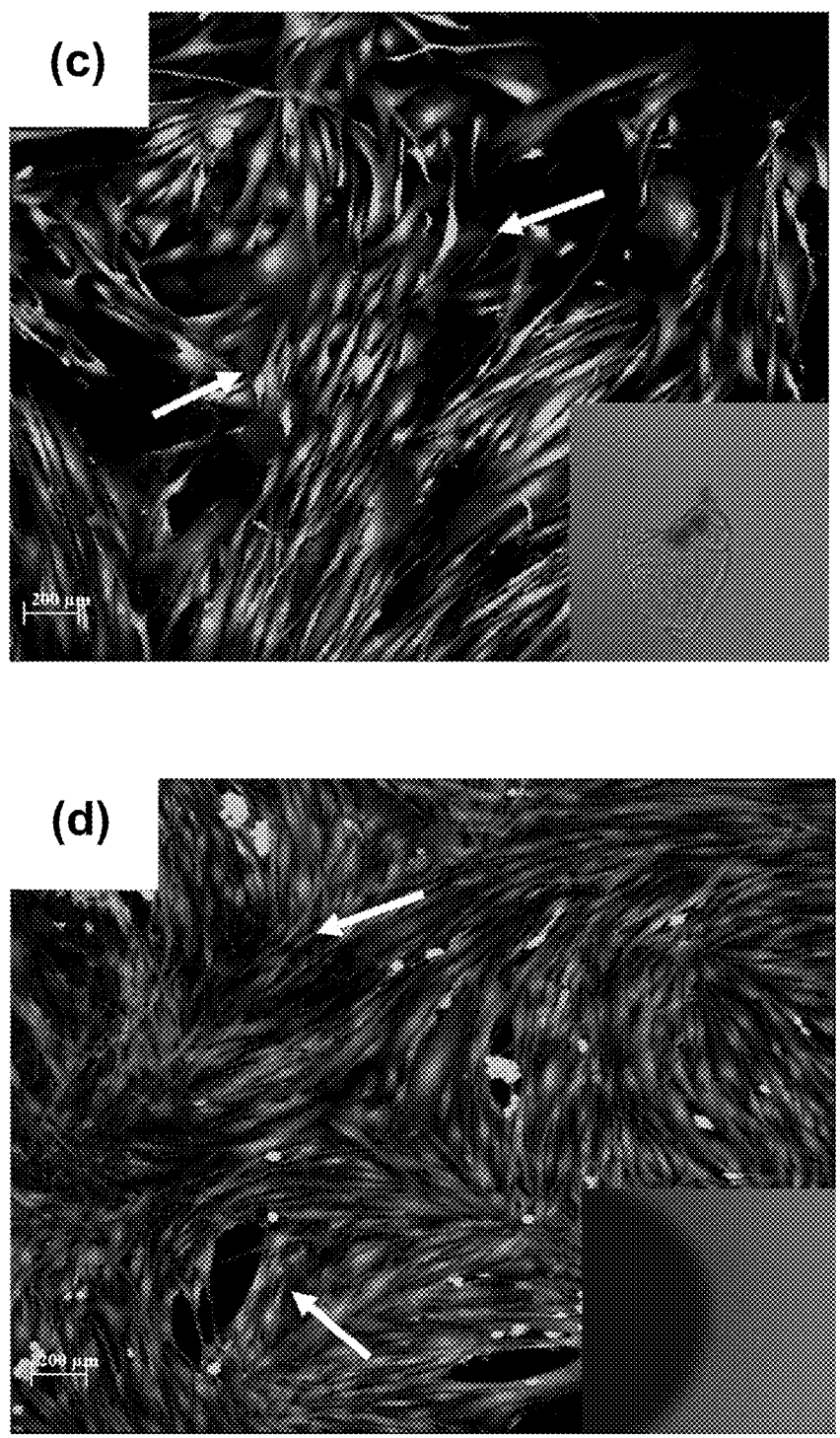

To use a biomaterial as a hemostatic agent for stopping bleeding, it is useful to evaluate its cellular toxicity. FIG. 16(a) illustrates potential effects of 1% Ga-MBG, CX and ACS$^+$ on HDF viability as assessed by MTT assays. The results revealed that all these samples were non-toxic to HDF cells and potentially useful for haemostatic applications. With respect to the negative control (TCPS), direct exposure of the tested samples to HDF cells increased slightly the HDF cell viability after day 1. However, the viability of 1% Ga-MBG, CX and ACS$^+$-treated cells considerably increased at the further time point (3 days) as compared to the TCPS, especially in the presence of 1% Ga-MBG, which demonstrates the high biocompatibility of the tested materials. These results demonstrated good HDF cell behaviour in direct contact with these materials without signs of cytotoxicity. This result was also investigated by a Live/Dead assay using confocal microscopy. The fluorescence images (FIG. 16(b-d)) showed that, by extending the culture period to 3 days, a high number of cells exposed to the investigated materials appeared green, indicating a significant increase in viability of HDF cells. While 1% Ga-MBG showed a relatively higher proportion of living cells, the ACS$^+$ group exhibited the greatest number of dead cells.

III. Discussion

The development of advanced hemostatic materials is an emerging field of materials chemistry that exploits the tuneable surface properties of materials to modulate their coagulation response. The use of MBG materials as advanced hemostatic agents is a recent development that allows blood clot initiation to occur quickly on the material surface.

Figure 11:
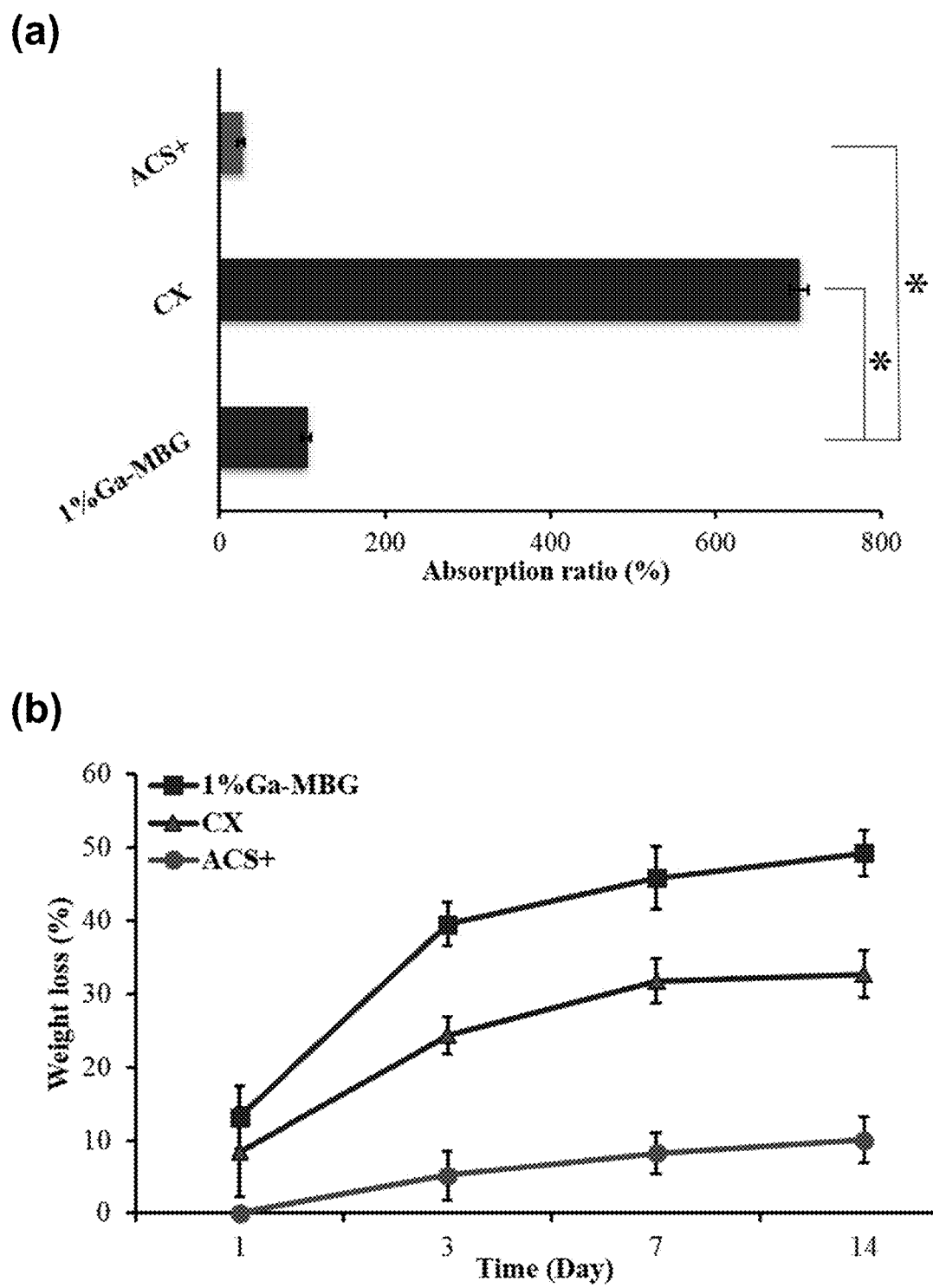
FIG. 11 shows the effect of 1% Ga-MBG, CX and ACS⁺ on (a) the water absorbance in terms of absorption ratio in percent; and (b) weight loss in percent as a function of time in days. * Indicates a significant difference, $p<0.05$.

The influence of 1% Ga-MBG properties on the promotion of the very early stages of hemostasis (coagulation, thrombin generation, platelet activation and thrombus formation) assessed and compared with CX and ACS$^+$. Evaluation of the APTT and PT assays indicated that, while the extrinsic pathway appears to be unaffected by the tested samples, the intrinsic pathway was significantly accelerated by 1% Ga-MBG and ACS$^+$ with respect to CX and the negative control. While not wishing to be limited by theory, there are several factors which cumulatively contribute to the ability of 1% Ga-MBG and ACS$^+$ to do this. For example, both 1% Ga-MBG and ACS$^+$ act as factor concentrators and/or pro-coagulants. Due to possessing a porous structure and a high specific surface area, while not wishing to be limited by theory, both inorganic materials rapidly absorb and sequester fluid phase components from the blood matrix and to concentrate cells, platelets and coagulation factors in the hemorrhaging blood, thus promoting hemostasis (that is the effect promoted by factor concentrators). However, the shortening of APTT was more pronounced in the presence of 1% Ga-MBG than in the presence of ACS$^+$. While 1% Ga-MBG with mesoporous interconnected structure provided higher specific surface area (597 m$^2$/g) and larger pore volume (0.7 cm$^3$ g$^{-1}$), being crucial to the fastest contact-activated, ACS$^+$ possess a microporous structure that is too small for plasma proteins to enter. These results were in good agreement with the PBS absorption results, where the 1% Ga-MBG sample presented greater capacity for water absorption compared with ACS$^+$ (FIG. 11).

In comparison to both 1% Ga-MBG and ACS$^+$, CX showed no effect on the activation of the intrinsic pathway, indicating an inverse relationship between water absorption and APTT results of the same material. So, despite its higher absorption rate, CX significantly prolonged the APTT. This result supports that the action mechanism of CX is independent of the classical coagulation cascade as previously reported[46,47]. The presence of calcium ions (Ca$^{2+}$) in 1% Ga-MBG and ACS$^+$'s framework is another factor favourable for the activation of the intrinsic blood coagulation cascade. These materials interact with the body's natural clotting ability and speed up the intrinsic pathway by supplying Ca$^{2+}$ that reside in their open porous internal space, thus accelerating the generation of required thrombin for fibrin polymerization and clot stabilization (that is the effect promoted by pro-coagulants). The higher surface area and mesoporous structure of 1% Ga-MBG allows the material to have higher capability to release sufficient amounts of Ca$^{+2}$ than ACS$^+$, inducing an accelerated coagulation response.

The effect of the materials analysed on the induction of the earliest stages of hemostasis (i.e. thrombin generation, platelet aggregation and thrombus formation) was also investigated. A different trend was found in the case of thrombin generation, platelet aggregation and thrombus formation in 1% Ga-MBG, CX and ACS$^+$. 1% Ga-MBG was found to be superior over CX and ACS$^+$ at thrombin generation and thrombus formation. While not wishing to be limited by theory, the increased thrombin generation and resultant fibrin formation in 1% Ga-MBG with respect to CX and ACS$^+$ can be attributed to the synergy of both its higher Ca$^{2+}$ release rate and negative surface charge alongside the structural features. As previously discussed, 1% Ga-MBG, due to possessing higher specific surface area and pore volume compared with ACS$^+$, while not wishing to be limited by theory, may have more capability to present Ca$^{2+}$ to blood, which not only is a required cofactor in the activation of the intrinsic pathway, but would also accelerate the production of sufficient amounts of thrombin, a pivotal enzyme of the coagulation cascade, to support early fibrin generation. Thrombin acts as a serine protease that converts circulating soluble fibrinogen into insoluble strands of fibrin, leading to formation of a stable thrombus[48].

The negative surface charge of 1% Ga-MBG also is another parameter contributing to its significant ability to enhance thrombin and thrombus formation better than CX and ACS$^+$. Negatively-charged surfaces are found to initiate the intrinsic pathway, a network of feedback-dependent reactions that, when activated, leads to a stable thrombus[49]. It is known that the adsorption of coagulation factor FXII on negatively charged surfaces leads to subtle conformational changes in the enzyme, which in turn provoke auto-activation. While not wishing to be limited by theory, the negative surface charge density influences the intensity of FXII activation by the presence of positively charged amino acids in its heavy chain, triggering its activation and leading to a strong amplification of contact activation proteins and subsequent activation of the intrinsic pathway[49,50]. This activation has been shown to play a significant role in thrombin formation and subsequent fibrin clot formation. The present results are in agreement with that 1% Ga-MBG with negative surface charge and strong contact activation causes substantially higher thrombin and thrombus formation than CX and $ACS^+$.

As previously described hereinabove, the textural properties of 1% Ga-MBG are involved in its increased thrombotic effect with respect to CX and $ACS^+$, allowing the material to rapidly absorb high amounts of water from the blood, and to concentrate cellular and blood plasma components, thus promoting thrombus formation. However, while $ACS^+$ was also expected to induce a more pronounced effect on early stages of hemostasis compared with CX due to carrying a negative charge, it produced much less thrombin and thrombus. While not wishing to be limited by theory, this observation can be attributed to the smaller pore volume of the zeolite in $ACS^+$ (0.12 $cm^3$ $g^{-1}$) compared to 1% Ga-MBG (0.7 $cm^3$ $g^{-1}$), which decreases the accessibility of the interior zeolite surface area for contact activation and is not beneficial to accommodate coagulation proteins such as $FXII^{51}$. It is therefore likely, while not wishing to be limited by theory, to be an underlying cause for thrombin and thrombus formation on the surface of CX. Most plasma proteins such as fibrinogen are negatively charged in blood, so that the negatively charged surfaces can inhibit their adsorption[52]. Thus while not wishing to be limited by theory, stronger fibrinogen adsorption can occur on positively charged surfaces, which in turn could be correlated with maximum platelet adhesion[49]. It is also evident that platelets play a major role in thrombin generation, leading to fibrin clot formation[53]. Therefore, while not wishing to be limited by theory, higher thrombin formation in the presence of CX compared to $ACS^+$ can be ascribed to a supporting effect of platelet adhesion on thrombin formation. The higher thrombus formation of CX with respect to $ACS^+$ can also, while not wishing to be limited by theory, be related to the positive charge of CX that cross-links with negatively charged RBCs and subsequently undergo chemical and mechanical linkages to form a sticky pseudo clot, blocking blood flow (that is the effect promoted by mucoadhesive hemostatic materials). However, the present results suggest, while not wishing to be limited by theory, that higher amounts of thrombus would be formed at a distance of CX powder.

In the case of platelet adhesion, although 1% Ga-MBG and CX revealed similar trends and were found to be superior over $ACS^+$, the platelets on 1% Ga-MBG exhibited typical signs of activation such as spread morphology and protruding filipodia, whereas a lower spreading rate of platelets was observed on CX. Contrary to what happens with CX, where only its positive charge may lead to fibrinogen adsorption via electrostatic attraction subsequently promoting the adhesion and activation of platelets, the synergy of both the excellent intrinsic textural properties (high specific surface area) and high release rate of $Ca^{2+}$ can affect the platelet adhesion and activation on the surface of 1% Ga-MBG. These parameters make 1% Ga-MBG a useful surface for contact activation of the intrinsic pathway, causing a submicron scale interaction with platelets and fibrinogen as well as a higher production of the proteolytic enzyme thrombin, causing clumping and activation of platelets on the surface itself. These results were in agreement with those of the blood coagulation, thrombin and thrombus formation assays, where 1% Ga-MBG was found to be more effective compared with CX and $ACS^+$.

The toxicity of inorganic-based hemostats such as Woundstat (TraumaCure, Inc., Bethesda, Md., USA) can be associated with the possibilities of leaching toxins from the minerals or their ability to remove important nutrients resulting from their known ion exchange properties[54]; therefore, direct contact between the mineral and the cells seemed necessary for cytotoxicity effects. Here, it was observed that the viability of HDF cells was increased in the direct presence of the hemostatic materials without signs of cytotoxicity as compared with control. For example, as shown in FIG. 16(a), the MTT assay demonstrated that, after 3 days of culture time, higher viability was observed for HDF cells in the presence of 1% Ga-MBG than CX and $ACS^+$, as also shown by fluorescence imaging. While not wishing to be limited by theory, the high specific surface and porosity values of 1% Ga-MBG can lead to higher Si leaching, which, while not wishing to be limited by theory, plays a positive role in HDF cell proliferation.

In order, for example, to accelerate the healing process and promote safety without any infection, the hemostats should be biodegradable. In contrast to CX and $ACS^+$, 1% Ga-MBG was found to degrade rapidly in Tris-HCl solution over 14 days resulting from its quick dissolution.

Figure 17:
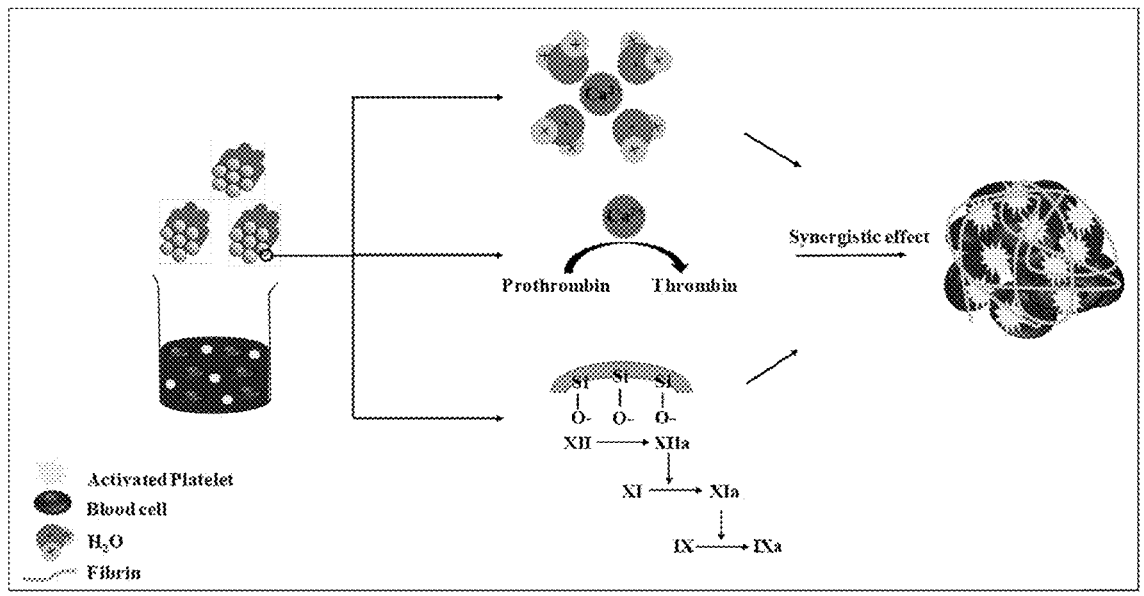
FIG. 17 shows a schematic illustration of blood clotting formation by 1% Ga-MBG through multiple modes of action.

In summary, 1% Ga-MBG was found to be more effective in the tests we performed, than two commercial hemostats, CX and $ACS^+$. 1% Ga-MBG allowed the greatest contact activation, platelet activation and thrombin generation followed by highest amount of thrombus formation. Neither platelet adhesion on CX surfaces without concurrent contact activation, nor contact activation on $ACS^+$ with lower number of the activated platelets leads to strong thrombus formation. While not wishing to be limited by theory, both contact activation and platelet adhesion are factors for biomaterials related coagulation activation, so that each single mechanism is not adequate to promote substantial thrombin formation. Therefore, 1% Ga-MBG may be useful for first aid treatment of wounds in critical situations, since it achieves a desirable hemostasis through the interplay of these activation processes. Based on the above analysis, while not wishing to be limited by theory, a combination hemostatic mechanism model of 1% Ga-MBG, shown in FIG. 17 is proposed.

IV. Conclusion

In the present example, the hemostatic efficacy as well as biocompatibility of 1% Ga-MBG was compared to CX and $ACS^+$. 1% Ga-MBG appeared to be an effective agent for achieving a desirable haemostasis with regard to CX and $ACS^+$, since it can accelerate the contact activation pathway of coagulation cascade and immobilize erythrocytes to promote blood clotting. The cytotoxicity evaluation results demonstrated that, when in direct contact with cells for different times, 1% Ga-MBG allowed HDF cells proliferation better than CX and $ACS^+$ with no signs of cell damage.

Prophetic Example 3

An object of this example is to develop a hemostat based on a mesoporous bioactive glass (MBG) which can be delivered to the wound site, for example, in particulate form or impregnated into a support such as a cellulose gauze. The construct may, for example, facilitate hemostasis, prevent inflammation of surrounding tissue, and/or minimize bacterial infection.

I. Overview

Glass compositions are identified that have potential for both accelerating thrombus formation and imparting antibacterial activity by using D-optimal methodology, a statistical approach that minimizes covariance amongst experimental variables and generates a compositional matrix containing varied levels of bioactive ions such as $Ga^{3+}$, $Ta^{5+}$, $Sr^{2+}$ and $Zn^{2+}$. MBGs are then synthesized from these precursor glasses. The MBGs are impregnated into a knitted cellulose gauze and characterized by conventional techniques. The use of these MBGs in clinical applications, both in particulate form (n=5) and when impregnated into the gauze (n=5), is evaluated through a suite of physical and biological techniques; the most promising compositions (n=3) are then evaluated in a mouse model. The gauze may, for example, provide a matrix for blood cell aggregation and the ionic species may both reduce tissue inflammation through neutralization of the acidic nature of cellulose and inhibit bacterial proliferation through an antimicrobial delivery system which has been shown to be more effective than antibiotics. These materials may be used for hemostasis in the clinic, postpartum, and in emergency situations and may, for example, minimise subsequent complications caused by bacterial infection.

II. Materials & Methods (a) Glass Formulation, Characterisation & MBG Processing Formulation:

The glass compositions with potential for accelerating thrombus formation and imparting anti-bacterial activity are identified by D-optimal methodology, a statistical approach that minimizes covariance amongst experimental variables and generates a compositional matrix containing varied levels of bioactive ions. Traditional composition-property studies consider glasses with only a few components that may be systematically varied to reveal trends. The formulation of multi-component glasses with specific properties is approached differently because there are too many components and non-linear composition-property relationships arise from component interactions[55]. D-optimal mixture design[56] generates a compositional matrix containing varied levels of: Ag (0-10 mol %), Ga (0-10), Na (0-10), Ca (0-20), Sr (0-20), Zn (0-20), Ti (0-5), Mo (0-1), and Si (50-60). This design is useful for multi-component glasses because, for example, it reduces a complex system to a tractable set of experiments and it incorporates constraints based on prior knowledge. Experimental variables may therefore be set based on a priori information.

Synthesis & Characterization:

Using the compositional matrix generated, 10 glasses are synthesized in platinum crucibles and amorphicity verified by X-ray diffraction. To study degradability, Fourier transform infrared (FTIR) and X-ray photoelectron spectroscopy (XPS) are used to identify the bonding configuration in the glasses and the presence of Si—O—NBO groups. Glass transition temperature ($T_g$) is determined by thermogravimetric analysis (TGA).

MBG Synthesis:

MBGs are produced from precursor glasses by the evaporation-induced self-assembly (EISA) process. Known masses of tetraethyl orthosilicate, triethyl phosphate, and the nitrate of a therapeutic ion such as Ga are dissolved in ethanol and stirred at room temperature for 1 day.

(b) Gauze Fabrication & Coating

Fabrication of Gauze:

Regenerated cellulose filaments are knitted (Wild man Jacquard, Pa., USA) to obtain a single layer of fabric. Oxidation induces degradability to the fabric[57,58]; achieved by immersing it in $NO_2/CCl_4$ oxidant solution, then freeze drying; the COOH content is determined by acido-basic titrimetric methods[57]. Samples are characterised by field emission scanning electron microscopy (FESEM).

MBG Impregnation:

The knitted gauze is dip-coated in a slurry of the bioglass. The surface area of the nanoporous layer is dependent on the number of coatings on the substrate. Microstructure and morphology of the samples is observed by FESEM and transmission electron microscopy (TEM). Elemental analysis is performed by energy dispersive spectroscopy (EDX) attached to the FESEM. The optimal arrangement of the samples (specific surface area>400 $m^2/g$, pore volume>0.5 $cm^3/g$, and pore size distribution<10 nm) is determined by Brunauer-Emmett-Teller (BET) and Barret-Joyner-Halenda (BJH) analyses. Pore size is assessed by mercury porosimetry to determine whether it is useful for blood absorption.

(c) In-Vitro & In-Vivo Evaluation

Ion release from the MBGs and the MBG-gauze constructs and their resultant anti-bacterial effects as a function of glass content and composition is evaluated. The hemostatic potential of both the MBGs and the MBG-gauze constructs is also evaluated. The gauze may, for example, provide a matrix for blood cell aggregation and the ionic species may, for example, both reduce tissue inflammation, through neutralization of the acidic nature of the cellulose component, and inhibit bacterial proliferation through an antimicrobial delivery system shown to be more effective than antibiotics.

(d) In Vitro Studies

Blood Absorption:

Determined in whole blood by recording the maximum amount of fluid absorption per unit weight of material.

Degradation Test:

Determined by immersing the samples for different durations (1, 3 & 7 days) in PBS (pH, 7.4; 37° C.), measuring the number and type of ions released with atomic absorption spectroscopy (AAS) and relating this to anti-bacterial activity.

Blood Coagulation Assay:

In vitro coagulation assays are performed to determine activated partial thromboplastin time (APTT) and prothrombin time (PT). Using an in vitro whole blood clotting assay, the pro-coagulation effect of MBGs and MBG/gauzes is evaluated in whole blood clot formation and clot retraction.

Platelet Activity Assay:

The activation of platelets after contact with the samples is studied with flow cytometry. The expression of platelet activation marker P-selectin and αIIbβ3 integrin activation is related to MBG composition.

Thrombus Formation:

The surface of rectangular perfusion chambers are coated with MBGs or MBGs with collagen. Mouse blood is perfused through the chambers under arterial and venous shear rates. After thrombus formation measurement, the interaction of blood cells with the materials (platelet thrombus formation) and fibrin structure (fiber lengths, diameters and branching densities) is observed by SEM and the relationship between clot morphology and its stability is investigated.

Thromboelastography (TEG) Analysis:

This tests the efficiency and kinetics of coagulation in the blood and evaluates the induced clotting effects of MBG materials. Parameters R (min, time from when blood is placed into the Thromboelastograph® cuvette until initial fibrin formation occurs), a (degree, the angle formed from R to the inflection point of the thromboelastographic signal) and MA (mm, the largest amplitude of the thromboelastographic signal) are obtained from the thromboelastographic curve indicating the onset of coagulation, rate of coagulation and maximum clot strength, respectively.

Anti-Bacterial Evaluation:

A direct contact method is used to evaluate anti-bacterial efficacy of the MBGs in particulate form and when impregnated into gauze[59] against *S. aureus* (Gram positive, common in skin infection), *E. coli* (Gram negative, common gastrointestinal flora), *S. pyogenes* (encountered in traumatic wound infections), and *P. aeruginosa* (common in sepsis, a multi-antibiotic resistance bacteria that can be eradicated by $Ga^{3+}$).

Cytotoxicity Assay:

Investigated by MTT tetrazolium assays using fibroblast cells (L929) according to the International Standards Organization standard (ISO/EN): 10993-5.

(e) In Vivo Studies

Hemostasis Assay:

Hemostatic efficacy of the two best performing materials is evaluated in a mouse model and the time to achieve complete hemostasis is recorded. At study end, each groin is opened and the liquid and clotted inguinal blood suctioned and measured. To determine any exotherm, temperatures in the femoral artery trauma are measured by two mercury thermometers placed at different sites of the interface between the material and the incised muscles; the higher of the two readings is recorded.

Intravital Microscopy Assay:

Small MBG particles are synthesised (diameter<2 μm) from the two chosen MBGs and their prothrombotic effect evaluated using mesentery arterial and laser injury cremaster arteriole thrombosis intravital microscopy models[60,51]. The initiation of platelet adhesion, thrombus growth and vessel occlusion time is recorded.

While the present disclosure has been described with reference to what are presently considered to be the preferred examples, it is to be understood that the application is not limited to the examples described herein. To the contrary, the present disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

[1] (a) Kauvar, D. S.; Lefering, R.; Wade, C. E., Impact of hemorrhage on trauma outcome: an overview of epidemiology, clinical presentations, and therapeutic considerations. *Journal of Trauma and Acute Care Surgery* 2006, 60 (6), S3-S11; (b) Sauaia, A.; Moore, F. A.; Moore, E. E.; Moser, K. S.; Brennan, R.; Read, R. A.; Pons, P. T., Epidemiology of trauma deaths: a reassessment. *The Journal of trauma* 1995, 38 (2), 185-193.

[2] B. J. Eastridge, R. L. Mabry, P. Seguin, J. Cantrell, T. Tops, P. Uribe, O. Mallett, T. Zubko, L. Oetjen-Gerdes and T. E. Rasmussen, *J. Trauma Acute Care Surg.*, 2012, 73, S431-S437.

[3] S. Pourshahrestani, E. Zeimaran, I. Djordjevic, N. A. Kadri and M. R. Towler, *Mater. Sci. Eng., C,* 2016, 58, 1255-1268.

[4] (a) Alam, H. B.; Burris, D.; DaCorta, J. A.; Rhee, P., Hemorrhage control in the battlefield: role of new hemostatic agents. *Military medicine* 2005, 170 (1), 63-69; (b) Wedmore, I.; McManus, J. G.; Pusateri, A. E.; Holcomb, J. B., The chitosan-based hemostatic dressing: Experience in current combat operations. *US Army Medical Department Journal* 2005, 58-62.

[5] F. L. Wright, H. T. Hua, G. Velmahos, D. Thoman, D. Demitriades and P. M. Rhee, *J. Trauma Acute Care Surg.,* 2004, 56, 205-208.

[6] V. Shanmugam and M. Robinson, *Colorectal Dis.,* 2009, 11, 221-222.

[7] P. Rhee, C. Brown, M. Martin, A. Salim, D. Plurad, D. Green, L. Chambers, D. Demetriades, G. Velmahos and H. Alam, *J. Trauma Acute Care Surg.,* 2008, 64, 1093-1099.

[8] Y. Ran, E. Hadad, S. Daher, O. Ganor, J. Kohn, Y. Yegorov, C. Bartal, N. Ash and G. Hirschhorn, *Prehosp. Disaster Med.,* 2010, 25, 584-588.

[9] M. E. Chávez-Delgado, C. V. Kishi-Sutto, X. N. A. de la-Riva, M. Rosales-Cortes and P. Gamboa-Sánchez, *J. Surg. Res.,* 2014, 192, 678-685.

[10] (a) Kheirabadi, B., Evaluation of topical hemostatic agents for combat wound treatment. *US Army Med Dep J* 2011, 2 (1), 25-37; (b) Cox, E. D.; Schreiber, M. A.; McManus, J.; Wade, C. E.; Holcomb, J. B., New hemostatic agents in the combat setting. *Transfusion* 2009, 49 (s5), 248S-255S; (c) Rhee, P.; Brown, C.; Martin, M.; Salim, A.; Plurad, D.; Green, D.; Chambers, L.; Demetriades, D.; Velmahos, G.; Alam, H., QuikClot use in trauma for hemorrhage control: case series of 103 documented uses. *Journal of Trauma and Acute Care Surgery* 2008, 64 (4), 1093-1099; (d) Acheson, E. M.; Kheirabadi, B. S.; Deguzman, R.; Dick Jr, E. J.; Holcomb, J. B., Comparison of hemorrhage control agents applied to lethal extremity arterial hemorrhages in swine. *Journal of Trauma and Acute Care Surgery* 2005, 59 (4), 865-875.

[11] D. S. Kauvar, R. Lefering and C. E. Wade, *J. Trauma Acute Care Surg.,* 2006, 60, S3-S11.

[12] J. K. Wright, J. Kalns, E. A. Wolf, F. Traweek, S. Schwarz, C. K. Loeffler, W. Snyder, L. D. Yantis Jr and J. Eggers, *J. Trauma Acute Care Surg.,* 2004, 57, 224-230.

[13] Kheirabadi, B. S.; Edens, J. W.; Terrazas, I. B.; Estep, J. S.; Klemcke, H. G.; Dubick, M. A.; Holcomb, J. B., Comparison of new hemostatic granules/powders with currently deployed hemostatic products in a lethal model of extremity arterial hemorrhage in swine. *J Trauma Acute Care* 2009, 66 (2), 316-328.

[14] Bennett, B. L.; Littlejohn, L. F.; Kheirabadi, B. S.; Butler, F. K.; Kotwal, R. S.; Dubick, M. A.; Bailey, J. A. *Management of External Hemorrhage in Tactical Combat Casualty Care: Chitosan-Based Hemostatic Gauze Dressings. TCCC Guidelines Change* 13-05; DTIC Document: 2014.

[15] B. Kheirabadi, *US Army Med. Dep. J.,* 2011, 2, 25-37.

[16] D. R. King, *J. Trauma Acute Care Surg.,* 2011, 71, 1775-1778.

[17] Floyd, C. T.; Rothwell, S. W.; Risdahl, J.; Martin, R.; Olson, C.; Rose, N., Salmon thrombin-fibrinogen dressing allows greater survival and preserves distal blood flow compared to standard kaolin gauze in coagulopathic swine with a standardized lethal femoral artery injury. *J Spec Oper Med* 2012, 12 (2), 16-26.

[18] Kheirabadi, B. S.; Mace, J. E.; Terrazas, I. B.; Fedyk, C. G.; Estep, J. S.; Dubick, M. A.; Blackbourne, L. H., Safety evaluation of new hemostatic agents, smectite granules, and kaolin-coated gauze in a vascular injury wound model in swine. *Journal of Trauma and Acute Care Surgery* 2010, 68 (2), 269-278.

[19] (a) Kheirabadi, B. S.; Scherer, M. R.; Estep, J. S.; Dubick, M. A.; Holcomb, J. B., Determination of efficacy of new hemostatic dressings in a model of extremity arterial hemorrhage in swine. *Journal of Trauma and Acute Care Surgery* 2009, 67 (3), 450-460; (b) Gustafson, S. B.; Fulkerson, P.; Bildfell, R.; Aguilera, L.; Hazzard, T. M., Chitosan dressing provides hemostasis in swine femoral arterial injury model. *Prehospital Emergency Care* 2007, 11 (2), 172-178.

[20] C. K. Murray, S. A. Roop, D. R. Hospenthal, D. P. Dooley, K. Wenner, J. Hammock, N. Taufen and E. Gourdine, *Bacteriology of war wounds at the time of injury*, DTIC Document, 2006.

[21] N. E. Aronson, J. W. Sanders and K. A. Moran, *Clin. Infect. Dis.*, 2006, 43, 1045-1051.

[22] X. Yan, C. Yu, X. Zhou, J. Tang and D. Zhao, *Angew. Chem., Int. Ed.*, 2004, 43, 5980-5984.

[23] L. L. Hench, *J. Am. Ceram. Soc.*, 1998, 81, 1705-1728.

[24] Y. Li, Y.-Z. Liu, T. Long, X.-B. Yu, T. T. Tang, K.-R. Dai, B. Tian, Y.-P. Guo and Z.-A. Zhu, *J. Mater. Sci.: Mater. Med.*, 2013, 24, 1951-1961.

[25] Y. Zhu, C. Wu, Y. Ramaswamy, E. Kockrick, P. Simon, S. Kaskel and H. Zreiqat, *Microporous Mesoporous Mater.*, 2008, 112, 494-503.

[26] S. Brunauer, P. H. Emmett and E. Teller, *J. Am. Chem. Soc.*, 1938, 60, 309-319.

[27] E. P. Barrett, L. G. Joyner and P. P. Halenda, *J. Am. Chem. Soc.*, 1951, 73, 373-380.

[28] W. Fan, D. Wu, T. Ma and B. Fan, Dent. Mater. J., 2015, 34, 54-60. [28(a)] C. Dai, Y. Yuan, C. Liu, J. Wei, H. Hong, X. Li and X. Pan, Biomaterials, 2009, 30, 5364-5375. [28(b)] C. Dai, C. Liu, J. Wei, H. Hong and Q. Zhao, Biomaterials, 2010, 31, 7620-7630

[29] Y. Imai and Y. Nose, *J. Biomed. Mater. Res.*, 1972, 6, 165-172.

[30] S.-Y. Ong, J. Wu, S. M. Moochhala, M.-H. Tan and J. Lu, *Biomaterials*, 2008, 29, 4323-4332.

[31] M. Ip, S. L. Lui, V. K. Poon, I. Lung and A. Burd, *J. Med. Microbiol.*, 2006, 55, 59-63.

[32] A. López-Noriega, D. Arcos, I. Izquierdo-Barba, Y. Sakamoto, O. Terasaki and M. Vallet-Regi, *Chem. Mater.*, 2006, 18, 3137-3144.

[33] D. Arcos, M. Vila, A. López-Noriega, F. Rossignol, E. Champion, F. Oliveira and M. Vallet-Regi, *Acta Biomater.*, 2011, 7, 2952-2959.

[34] C. Vaid, S. Murugavel, R. Kashayap and R. P. Tandon, *Micropor Mesopor Mat*, 2012, 159, 17-23.

[35] X. Yan, X. Huang, C. Yu, H. Deng, Y. Wang, Z. Zhang, S. Qiao, G. Lu and D. Zhao, *Biomaterials*, 2006, 27, 3396-3403.

[36] M. Franchini, G. Lusvardi, G. Malavasi and L. Menabue, *Mater. Sci. Eng., C*, 2012, 32, 1401-1406.

[37] M. N. Rahaman, D. E. Day, B. S. Bal, Q. Fu, S. B. Jung, L. F. Bonewald and A. P. Tomsia, *Acta Biomater.*, 2011, 7, 2355-2373.

[38] V. Grover, A. Kapoor, R. Malhotra and R. S. Uppal, *J. Indian Soc. Periodontol.*, 2013, 17, 104.

[39] Y. Zhao, X. Sun, G. Zhang, B. G. Trewyn, I. I. Slowing and V. S.-Y. Lin, *ACS Nano*, 2011, 5, 1366-1375.

[40] S. R. Coughlin, *Nature*, 2000, 407, 258-264. [40a] B. S. Kheirabadi, J. W. Edens, I. B. Terrazas, J. S. Estep, H. G. Klemcke, M. A. Dubick and J. B. Holcomb, J. Trauma Acute Care Surg., 2009, 66, 316-328.

[41] Brunauer, S.; Emmett, P. H.; Teller, E., Adsorption of gases in multimolecular layers. *Journal of the American chemical society* 1938, 60 (2), 309-319. [41a] Pourshahrestani, S.; Zeimaran, E.; Kadri, N. A.; Gargiulo, N.; Samuel, S.; Naveen, S. V.; Kamarul, T.; Towler, M. R., Gallium-containing mesoporous bioactive glass with potent hemostatic activity and antibacterial efficacy. *Journal of Materials Chemistry B* 2016, 4 (1), 71-86.

[42] Barrett, E. P.; Joyner, L. G.; Halenda, P. P., The determination of pore volume and area distributions in porous substances. I. Computations from nitrogen isotherms. *Journal of the American Chemical society* 1951, 73 (1), 373-380.

[43] Dai, C.; Yuan, Y.; Liu, C.; Wei, J.; Hong, H.; Li, X.; Pan, X., Degradable, antibacterial silver exchanged mesoporous silica spheres for hemorrhage control. *Biomaterials* 2009, 30 (29), 5364-5375.

[44] Ahuja, N.; Ostomel, T. A.; Rhee, P.; Stucky, G. D.; Conran, R.; Chen, Z.; Al-Mubarak, G. A.; Velmahos, G.; Alam, H. B., Testing of modified zeolite hemostatic dressings in a large animal model of lethal groin injury. *Journal of Trauma and Acute Care Surgery* 2006, 61 (6), 1312-1320.

[45] Schneider, P., Adsorption isotherms of microporous-mesoporous solids revisited. *Applied Catalysis A: General* 1995, 129 (2), 157-165.

[46] Kheirabadi, B., Evaluation of topical hemostatic agents for combat wound treatment. *US Army Med Dep J* 2011, 2 (1), 25-37.

[47] Rao, S. B.; Sharma, C. P., Use of chitosan as a biomaterial: studies on its safety and hemostatic potential. *Journal of biomedical materials research* 1997, 34 (1), 21-28.

[48] Coughlin, S. R., Thrombin signalling and protease-activated receptors. *Nature* 2000, 407 (6801), 258-264.

[49] Sperling, C.; Fischer, M.; Maitz, M. F.; Werner, C., Blood coagulation on biomaterials requires the combination of distinct activation processes. *Biomaterials* 2009, 30 (27), 4447-4456.

[50] Colman, R. W.; Schmaier, A. H., Contact system: a vascular biology modulator with anticoagulant, profibrinolytic, antiadhesive, and proinflammatory attributes. *Blood* 1997, 90 (10), 3819-3843.

[51] Baker, S. E.; Sawvel, A. M.; Fan, J.; Shi, Q.; Strandwitz, N.; Stucky, G. D., Blood clot initiation by mesocellular foams: dependence on nanopore size and enzyme immobilization. *Langmuir* 2008, 24 (24), 14254-14260.

[52] He, Q.; Gong, K.; Ao, Q.; Ma, T.; Yan, Y.; Gong, Y.; Zhang, X., Positive charge of chitosan retards blood coagulation on chitosan films. *Journal of biomaterials applications* 2013, 27 (8), 1032-1045.

[53] Monroe, D. M.; Hoffman, M.; Roberts, H. R., Platelets and thrombin generation. *Arteriosclerosis, thrombosis, and vascular biology* 2002, 22 (9), 1381-1389.

[54] Bowman, P. D.; Wang, X.; Meledeo, M. A.; Dubick, M. A.; Kheirabadi, B. S., Toxicity of aluminum silicates used in hemostatic dressings toward human umbilical veins endothelial cells, HeLa cells, and RAW267. 4 mouse macrophages. *Journal of Trauma and Acute Care Surgery* 2011, 71 (3), 727-732.

[55] Shelby J E. Introduction to glass science and technology: Royal Society of Chemistry; 2005.

[56] Montgomery DC. Design and analysis of experiments: Wiley New York; 1982.

[57] Novotna K, et al. Cellulose 2013; 20:2263-78.

[58] Lewis K, et al. European Surgery 2013; 45:213-20.

[59] Slutzky-Goldberg I, et al. Journal of endodontics 2008; 34:735-8.
[60] Ni H, et al. The Journal of clinical investigation 2000; 106:385-92.
[61] Wang Y, et al. The Journal of clinical investigation 2014; 124:4281-93.

The invention claimed is:

1. A method for inducing hemostasis in a subject in need thereof, the method comprising contacting blood with a hemostatically effective amount of a composition comprising a mesoporous bioactive glass (MBG), wherein the MBG comprises:
   (i) silicon dioxide in an amount from about 50.0 mol % to about 90 mol %;
   (ii) calcium oxide in an amount from about 10.0 mol % to about 20 mol %;
   (iii) phosphorous pentoxide in an amount from about 1.0 mol % to 10 mol %; and
   (iv) a metal ion which is tantalum and present in an amount from about 0.1 mol % to about 5.0 mol %.

2. The method of claim 1, wherein the MBG comprises silicon dioxide in an amount from about 77.0 mol % to about 79 mol %
calcium oxide in an amount of about 15.0 mol %;
phosphorous pentoxide in an amount of about 5.0 mol %;
a metal tantalum ion in an amount from about 1.0 mol % to about 5.0 mol %.

3. The method of claim 1, wherein the MBG comprises silicon dioxide in an amount of about 79.0 mol %;
calcium oxide in an amount of about 15.0 mol %;
phosphorous pentoxide in an amount of about 5.0 mol %;
the tantalum ion in an amount of about 5.0 mol %.

4. The method of claim 1, wherein the MBG comprises silicon dioxide in an amount of about 79.0 mol %;
calcium oxide in an amount of about 15.0 mol %;
phosphorous pentoxide in an amount of about 5.0 mol %;
a metal tantalum ion in an amount of about 1.0 mol %.

5. The method of claim 1, wherein the MBG has a surface area of at least 500 $m^2/g$.

6. The method of claim 1, wherein the tantalum ion is present as $Ta_2O_5$.

7. The method of claim 1, wherein the MBG has small angle X-ray diffraction peaks of 2θ at 1.1°.

8. The method of claim 1, wherein inducing hemostasis decreases the blood coagulation time.

9. The method of claim 1, wherein the MBG has a surface area of at least 500 $m^2/g$.

10. The method of claim 1, wherein the MBG further comprises a metal ion selected from germanium, zinc and strontium.

* * * * *

UNITED STATES PATENT AND TRADEMARK OFFICE
CERTIFICATE OF CORRECTION

PATENT NO. : 11,369,633 B2
APPLICATION NO. : 15/354289
DATED : June 28, 2022
INVENTOR(S) : Towler Page 1 of 1

It is certified that error appears in the above-identified patent and that said Letters Patent is hereby corrected as shown below:

In the Claims

1. Column 38, Line 1, "a metal tantalum ion in an amount from about 1.0 mol% to about 5.0 mol%." should read --a tantalum ion in an amount from about 1.0 mol% to about 5.0 mol%.--

2. Column 38, Line 12, "a metal tantalum ion in an amount of about 1.0 mol%." should read --a tantalum ion in an amount of about 1.0 mol%.--

Signed and Sealed this
Sixth Day of September, 2022

Katherine Kelly Vidal
*Director of the United States Patent and Trademark Office*